(12) United States Patent
Baxter et al.

(10) Patent No.: US 6,812,226 B2
(45) Date of Patent: Nov. 2, 2004

(54) P2X$_7$ RECEPTOR ANTAGONISTS FOR USE IN THE TREATMENT OF INFLAMMATORY, IMMUNE OR CARDIOVASCULAR DISEASE

(75) Inventors: Andrew Baxter, Loughborough (GB); Nicholas Kindon, Loughborough (GB); Garry Pairaudeau, Loughborough (GB); Bryan Roberts, Loughborough (GB); Stephen Thom, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/149,760

(22) PCT Filed: Dec. 12, 2000

(86) PCT No.: PCT/SE00/02504

§ 371 (c)(1),
(2), (4) Date: Jun. 13, 2002

(87) PCT Pub. No.: WO01/44213

PCT Pub. Date: Jun. 21, 2001

(65) Prior Publication Data

US 2003/0040513 A1 Feb. 27, 2003

(30) Foreign Application Priority Data

Dec. 17, 1999 (SE) .............................................. 9904652

(51) Int. Cl.$^7$ ...................... A61K 31/33; A61K 31/535; C07D 265/12; C07D 265/36; C07D 213/00
(52) U.S. Cl. ................. 514/183; 514/230.8; 514/228.8; 544/92; 544/105; 546/315; 546/316; 546/329
(58) Field of Search .............................. 514/183, 230.8, 514/228.8; 544/92, 105; 546/315, 316, 329

(56) References Cited

U.S. PATENT DOCUMENTS 5,756,497 A * 5/1998 Bell et al. ................. 514/230.5

FOREIGN PATENT DOCUMENTS

| WO | WO 96/13262 | 5/1996 |
| WO | WO 99/29686 | 6/1999 |

OTHER PUBLICATIONS

Cecil Textbook of Medicine, 20$^{th}$ edition, vol. 2, 1992–1996(1996).*
PubMed Abstract 12621313, also cited as J. Cereb. Blood Flow Metab.,23/3,381–4(2003).*
PubMed Abstract12910626, also cited as J. Soc. Biol.,197/2,113–22(2003).*
PubMed Abstract 14511112,also cited as J. Neurochem.,87/2,344–52(2003).*

PubMed Abstract 14561158, also cited as Curr. Drug Targets Inflamm. Allergy,2/3,2322–41(2003).*
Ferrari et al., "Purinergic Modulation of Interleukin–1β Release from Microglial Cells Stimulated with Bacterial Endotoxin", J. Exp. Med., 185 (3),.1997, pp. 579–582.
Ferrari et al., "Extracellular ATP Triggers IL–1β Release by Activating the Purinergic P2Z Receptor of Human Macrophages", Journal of Immunology, 1997, 159(3), pp. 1451–1458.
Yu et al., "Inhibition of IL–1 Release from Hunan Monocytes and Suppression of Streptococcal Cell Wall and Adjuvant–induced Arthritis in Rats by an Extract of *Tripterygium wilfordii* Hook", General Pharmacology, 1994, 25(6), pp. 1115–1122.
Otterness et al., "Possible Role of IL–1 in Arthritis: Effects of Prostaglandins in the Regulation of IL–1 Synthesis and Actions", Joint Destruction in Arthritis and Osteoarthritis, Agents and Actions Supplements, 1993, 39, pp. 109–120.
Henderson et al., "Inhibition of Interleukin–1–Induced Synovitis and Articular Cartilage Proteoglycan Loss in the Rabbit Knee by Recombinant Human Interleukin–1 Receptor Antagonist", Cytokine, 3(3), 1991, pp. 246–249.
Kodata et al., "Significance of IL–1β and IL–1 receptor antagonist (IL–1Ra) in bronchoalveolar lavage fluid (BALF) in patients with diffuse panbronchiolitis (DPB)", Clin Exp Immunol, 1996, 103, pp. 461–466.
Sakito et al., "Interleukin 1β, Tumor Necrosis Factor Alpha, and Interleukin 8 in Bronchoalveolar Lavage Fluid of Patients with Diffuse Panbronchiolitis: A Potential Mechanism of Macrolide Therapy", Respiration, 63, pp. 42–48.

* cited by examiner

Primary Examiner—Richard L. Raymond
Assistant Examiner—Sudhaker B. Patel
(74) Attorney, Agent, or Firm—Morgan, Lewis & Bockius LLP

(57) ABSTRACT

The invention provides piperidine compounds of general formula (I) in which A, B, X, Y, Z, R, R$^1$ and R$^2$ are as defined in the specification, their use as medicaments, compositions containing them and processes for their for their preparation.

(I)

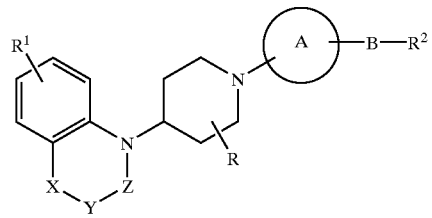

14 Claims, No Drawings

P2X7 RECEPTOR ANTAGONISTS FOR USE IN THE TREATMENT OF INFLAMMATORY, IMMUNE OR CARDIOVASCULAR DISEASE

The present invention relates to piperidine derivatives, a process for their preparation, pharmaceutical compositions containing them, a process for preparing the pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and L-selectin shedding (lymphocytes). $P2X_7$ receptors are also located on antigen-presenting cells (APC), keratinocytes, salivary acinar cells (parotid cells) and hepatocytes.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of formula (I):

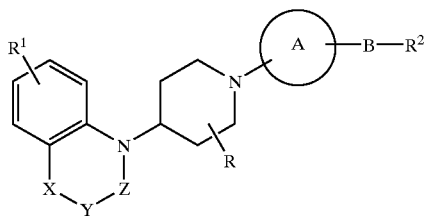

where

A is phenyl or a 5- or 6-membered heterocyclic ring containing one or two heteroatoms selected from O, N or S; and optionally substituted by $C_{1-6}$alkyl, halogen, nitro, amino, alkylamino, $CF_3$, $SO_2Me$, $NHSO_2Me$ or cyano;

B is C=O, NH or $SO_2$;

X is C=O, CH(Me), O or $(CH_2)p$ where p is 0 or 1;

Y is O, $CH_2$, NH or S;

Z is C=O or $SO_2$, provided that when Z is C=O, then Y is O, $CH_2$ or S;

R is hydrogen or $C_{1-6}$alkyl;

$R^1$ is hydrogen, halogen;

$R^2$ is phenyl optionally substituted by $CO_2H$, $CO_2$alkyl, $CONH_2$ or $R^2$ is OH, $NHR^3$, $NHCH(R^4)(CHR^5)_nR^6$, $NH-R^7-R^8$, $SO_2NH$alkyl, $NHCO$alkyl, $NHSO_2$alkyl, morpholine, $NR^9R^{10}$, piperazine substituted by phenyl, alkoxyphenyl, pyridyl or fluorophenyl;

n is 0, 1 or 2;

$R^3$ is hydrogen, a bi- or tricyclic saturated ring system optionally containing a nitrogen atom, piperidinyl, alkylpyrollidine, ethynylcyclohexyl, a 5-membered aromatic ring containing 2 or 3 heteroatoms, $C_{4-6}$ cycloalkyl optionally substituted by alkyl, cyano or hydroxy, or $C_{1-8}$alkyl optionally containing an oxygen atom in the alkyl chain and being optionally substituted by one or more substituents selected from ethynyl, cyano, fluoro, di-alkylamino, hydroxy, thioalkyl, $CO_2R^{11}$ or $CONH_2$;

$R^4$ is hydrogen or alkyl optionally substituted by hydroxy or alkoxy;

$R^5$ is hydrogen or hydroxy;

$R^6$ is $CO_2R^{11}$, $NHCO_2R^{12}$, $CONH_2$ or a 5 or 6-membered saturated ring containing an oxygen atom, a 5-membered heterocyclic ring containing one or two heteroatoms selected from O, N or S, or phenyl optionally substituted by one or more groups selected from alkyl, hydroxy, amino, alkoxy, or nitro;

$R^6$ is alkyl;

$R^7$ is a cyclopentane ring;

$R^8$ is phenyl;

$R^9$ and $R^{10}$ are independently hydrogen, benzyl, alkenyl, cycloalkyl, alkyl optionally substituted by hydroxy, alkoxy, cyano, dialkylamino, phenyl, pyridyl or $CO_2R^{11}$ or $R^9$ and $R^{10}$ together form a 5- to 7-membered saturated or partially saturated ring optionally containing a further heteroaton and optionally substituted by one or more groups selected from alkyl (optionally containing an oxygen atom in the chain and optionally substituted by hydroxy), COalkyl, $CO_2R^{11}$, $COR^{13}R^{14}$, CHO or piperidine, $R^{11}$ is hydrogen or alkyl;

$R^{12}$ is alkyl; and $R^{13}$ and $R^{14}$ are independently hydrogen or alkyl, and pharmaceutically acceptable salts and solvates thereof In the context of the present specification, unless otherwise indicated, an alkyl substituent or alkyl moiety in a substituent group may be linear or branched and may contain up to 6 carbon atoms, examples of which include methyl, ethyl, n-propyl, isopropyl, n-butyl, isobutyl, t-butyl, n-pentyl and n-hexyl.

Suitably A is phenyl or a 5- or 6-membered heterocyclic ring containing one or two heteroatoms selected from O, N or S; and optionally substituted by $C_{1-6}$alkyl, halogen, nitro, amino, alkylamino, $CF_3$, $SO_2Me$, $NHSO_2Me$ or cyano. Examples of suitable 5- or 6-membered heterocyclic rings include. Preferably A is optionally substituted phenyl, more preferably A is phenyl substituted by a nitro group.

Suitably B is C=O, NH or $SO_2$. Preferably B is C=O.

Suitably X is C=O, CH(Me), O or $(CH_2)p$ where p is 0 or 1, Y is O, $CH_2$, NH or S and Z is C=O or $SO_2$. Examples of groups formed by X, Y and Z include benzoxazinone and dihydroquinoline. Preferably X is $CH_2$, Y is O and Z is C=O such that X, Y and Z together form part of a benzoxazinone ring which can be optionally substituted by methyl.

Suitably R is hydrogen or $C_{1-6}$alkyl, preferably R is hydrogen.

Suitably $R^1$ is hydrogen or halogen, preferably $R^1$ is hydrogen.

Suitably $R^2$ is phenyl optionally substituted by $CO_2H$, $CO_2$alkyl, $CONH_2$ or $R^2$ is OH, $NHR^3$, $NHCH(R^4)(CHR^5)_nR^6$, $NH-R^7-R^8$, $SO_2NH$alkyl, $NHCO$alkyl, $NHSO_2$alkyl, morpholine, $NR^9R^{10}$, piperazine substituted by phenyl, alkoxyphenyl, pyridyl or fluorophenyl. Preferably $R^2$ is $NR^9R^{10}$ where one of $R^9$ or $R^{10}$ is hydrogen and the other is alkyl such as $CH(CH_3)_2$.

Particularly preferred compounds of the invention include those exemplified herein both in free base form as well as all pharmaceutically acceptable salts and/or solvates thereof According to the invention there is further provided a process for the preparation of a compound of formula (I) which comprises reaction of a compound of formula (II):

(II)

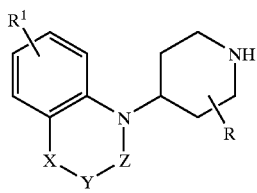

where R, R¹, X, Y and Z are as defined in formula (I) or a protected derivative thereof, with a compound of formula (III):

(III)

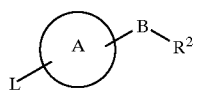

where B and R² are as defined in formula (I) or a protected derivative thereof, and L is a leaving group, and optionally thereafter in any order:

converting one or more functional groups into further functional groups removing any protecting groups forming a pharmaceutically acceptable salt or solvate.

Examples of suitable leaving groups L include halogen, OMs and OTs. Preferably L is halogen, in particular chloro.

The reaction of compounds of formula (II) and (III) is preferably carried out in the presence of an organic amine such as a trialkylamine, for example triethylamine. The reaction is preferably carried out in an inert solvent such as NMP, DMF or dioxan preferably at elevated temperature, for example at the reflux temperature of the reaction mixture.

Compounds of formulae (II) can be prepared as follows:

(a) by reacting a compound of formula (IV):

(IV)

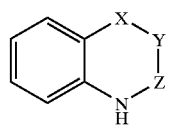

in which X, Y and Z are as defined in formula (II) or are protected derivatives thereof, with a compound of formula (V):

(V)

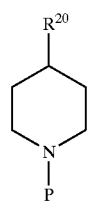

in which $R^{20}$ is a leaving group or an activated hydroxy group, or (b) by reacting a compound of formula (VI):

(VI)

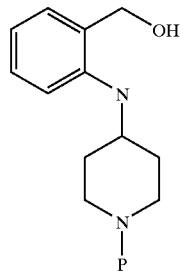

in which P a protecting group, with a compound of formula (VII):

(VII)

in which the groups L are leaving groups.

Compounds of formulae (IV) and (V) can be reacted under Mitsonobu conditions when $R^{20}$ in compound (V) is an activated hydroxy group. For the reaction of compounds (VI) and (VII), examples of suitable leaving L groups include halogen, in particular chloro, or imidazole. Alternatively triphosgene can be used. Suitable protecting groups for compounds (V) and (VI) include t-butoxy carbonyl (Boc).

Compounds of formula (III), (IV), (V) and (VII) are prepared using lterature procedures or are commercially available.

Functional groups can be converted into further functional groups using procedures known in the art. For example a carboxylic acid group can be converted into an ester or amide using standard chemistry.

Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Deprotection can be carried out using methods generally known in the art.

All novel intermediates form a further aspect of the invention.

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity and have utility as modulators of $P2X_7$ receptor activity. They are therefore indicated as pharmaceuticals for use in the treatment or prevention of rheumatoid arthritis, osteoarthritis, psoriasis, allergic dermatitis, asthma, hyperresponsiveness of the airway, chronic obstructive pulmonary disease (COPD), bronchitis, septic shock, glomerulonephritis, irritable bowel disease, Crohn's disease, ulcerative colitis, atherosclerosis, growth and metastases of malignant cells, myoblastic leukaemia, diabetes, neurodegenerative disease, Alzheimer's disease, meningitis, osteoporosis, burn injury, ischaemic heart disease, stroke, peripheral vascular disease and varicose veins.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will now be further illustrated by reference to the following examples.

EXAMPLE 1

2-({3-Nitro-4-[4-(2-oxo-2H-3,1-benzoxazin-1(4H)-yl)piperidin-1-yl]phenyl}carbonyl)benzoic acid

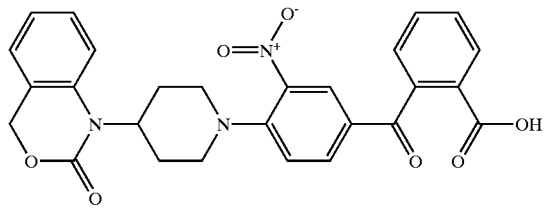

A solution of 1-piperidin-4-yl-1,4-dihydro-2H-3,1-benzoxazin-2-one hydrochloride (J.Med. Chem. 1998, 2157) (0.8 g), 2-(4-chloro-3-nitrobenzoyl)benzoic acid (0.9 g) and triethylamine (0.8 ml) in N,N-dimethylformamide (5 ml) was stirred at room temperature for 72 h. The mixture was partitioned between ethyl acetate and dilute hydrochloric acid, the organic layer was evaporated under reduced pressure. Purification was by chromatography eluting with 4% methanol/dichloromethane. The residue was triturated from methanol, yield 0.4 g as a solid.

MS: APCI(+ve) 502(M+1)

1H NMR: δ (CDCl3/DMSO-d6) 8.13–8.05(2H, m), 7.80 (1H, d), 7.70–7.57(2H, m), 7.43–7.33(2H, m), 7.23–7.09 (4H, m), 5.12(2H, s), 4.20–4.08(1H, m), 3.55(2H, d), 3.21 (2H, t), 2.90–2.80(2H, m), 1.97(2H, d)

MP: 243–4° C.

EXAMPLE 2

1-{1-[2-Nitro-4-(phenylcarbonyl)phenyl]piperidin-4-yl}-1,4-dihydro-2H-3,1-benzoxazin-2-one

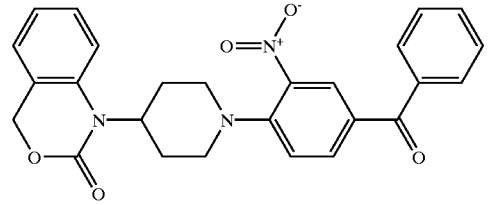

The title compound was prepared from 1-piperidin-4-yl-1,4-dihydro-2H-3,1-benzoxazin-2-one hydrochloride (0.3 g) and 4-chloro-3-nitrobenzophenone (0.29 g) using the method of example 1. Yield 0.25 g as a solid.

MS: APCI(+ve) 458(M+1)

1H NMR: δ (CDCl3/DMSO-d6) 8.28(1H, d), 7.98(1H, dd), 7.78–7.75(2H, m), 7.63–7.60(1H, m), 7.53–7.50(2H, m), 7.38(1H, t), 7.22–7.10(4H, m), 5.11(2H, s), 4.25–4.19 (1H, m), 3.61(2H, d), 3.23(2H, t), 2.93–2.84(2H, m), 1.98 (2H, d)

MP: 272–3° C.

EXAMPLE 3

Methyl 2-({3-nitro-4-[4-(2-oxo-2H-3,1-benzoxazin-1(4H)-yl)piperidin-1-yl]phenyl}carbonyl)benzoate

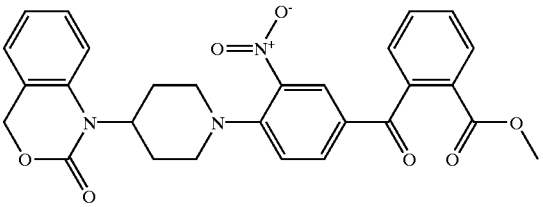

The product from example 1 was added to methanolic hydrogen chloride and the mixture stirred overnight. The solvent was removed under reduced pressure and the residue purified by chromatography. Yield 0.03 g.

MS: APCI(+ve) 516(M+1)

1H NMR: δ (CDCl$_3$) 8.10–8.07(2H, m), 7.91(1H, dd), 7.68–7.57(2H, m), 7.39–7.35(2H, m), 7.19–7.09(4H, m), 5.29(2H, s), 4.22–4.17(1H, m), 3.75(3H, s), 3.57(2H, d), 3.20(2H, t), 2.90–2.81(2H, m), 1.96(2H, d)

MP: 177–9° C.

EXAMPLE 4

2-({3-Nitro-4-[4-(2-oxo-2H-3,1-benzoxazin-1(4H)-yl)piperidin-1-yl]phenyl}carbonyl)benzamide

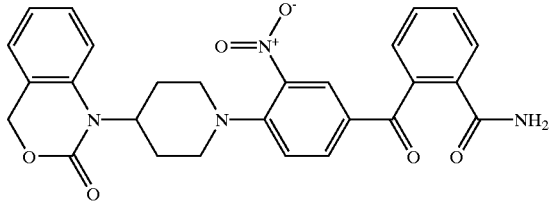

A solution of the product from example 1 (0.9 g) and carbonyldiimidazole (1.1 equiv.) in dichloromethane (4 ml) was stirred at room temperature for 1 h, poured onto aqueous ammonia and stirred for a further 1 h. The mixture was extracted with ethyl acetate, the organics washed with water, dried and evaporated under reduced pressure. Purification was by chromatography eluting with 2.5% methanol/dichloromethane. Yield 0.01 g as a solid.

MS: APCI(+ve) 501(M+1)

1H NMR: δ (CDCl$_3$) 8.08(1H, d), 7.64(1H, d), 7.58–7.34 (5H, m), 7.20–7.07(4H, m), 7.03(1H, s), 5.08(2H, s), 4.35 (1H, s), 4.21–4.13(1H, m), 3.42(2H, d), 3.04(2H, t), 2.86–2.74(2H, m), 1.90(2H, d)

MP: 180–2° C.

EXAMPLE 5

Methyl 2-({3-nitro-4-[4-(2-oxo-3,4-dihydroquinolin-1(2H)-yl)piperidin-1-yl]phenyl}carbonyl)benzoate

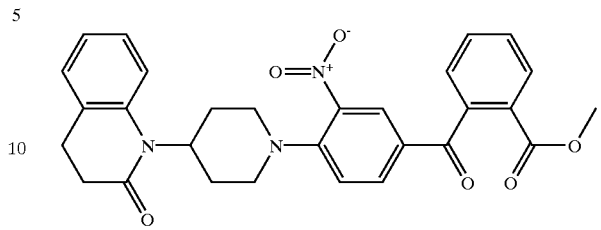

(i) 2-({3-Nitro-4-[4-(2-oxo-3,4-dihydroquinolin-1(2H)-yl)piperidin-1-yl]phenyl}carbonyl)benzoic acid

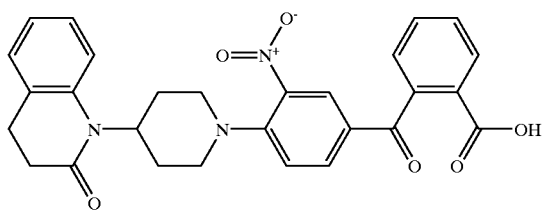

The product was prepared from 1-piperidin-4-yl-3,4-dihydroquinolin-2(1H)-one (Chem. Pharm. Bull. (1996), 44(4), 725–33) (0.45 g) and 2-(4-chloro-3-nitrobenzoyl) benzoic acid (0.6 g) using the method of example 1. Used crude.

(ii) Methyl 2-({3-nitro-4-[4-(2-oxo-3,4-dihydroquinolin-1(2H)-yl)piperidin-1-yl]phenyl}carbonyl)benzoate The title compound was prepared from the product from step (i) (0.2 g) which was added to methanolic hydrogen chloride and stirred at room temperature overnight. The solvent was removed under reduced pressure and the residue partitioned between ethyl acetate and aqueous sodium hydrogencarbonate solution. The organics were separated, dried and evaporated under reduced pressure. Purification was by chromatography to yield 0.18 g of a solid.

MS: APCI(+ve) 514(M+1)

1H NMR: δ (CDCl$_3$) 8.09–8.07(2H, m), 7.92(1H, dd), 7.68–7.56(2H, m), 7.37(1H, d), 7.26–7.13(4H, m), 7.03(1H, t), 4.50–4.46(1H, m), 3.74(3H, s), 3.53(2H, d), 3.18(2H, t), 2.86–2.75(4H, m), 2.61–2.57(2H, m), 1.84(2H, d)

MP: 12–3° C.

EXAMPLE 6

2-({3-Nitro-4-[4-(2-oxo-3,4-dihydroquinolin-1(2H)-yl)piperidin-1-yl]phenyl}carbonyl)benzoic acid

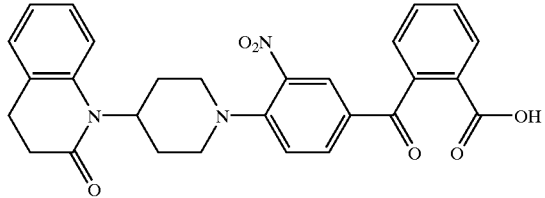

Lithium hydroxide hydrate (3 equiv.) was added to a mixture of the product from example 5 step (ii) (0.15 g) in methanol/water (5.5 ml, 10:1) and stirred overnight at room temperature. The solvent was removed under reduced pressure, the residue dissolved in water and neutralised with dilute hydrochloric acid. The mixture was extracted with ethyl acetate, dried and evaporated under reduced pressure. The residue was triturated with ether and the solid collected. Yield 0.06 g.

MS: APCI(+ve) 500(M+1)

1H NMR: δ (CDCl₃) 8.11(2H, m), 7.86(1H, dd), 7.71(1H, m), 7.59(1H, m), 7.38(1H, dd), 7.18(4H, m), 7.01(1H, m), 4.48(1H, m), 3.51(2H, m), 3.16(2H, m), 2.83(4H, m), 2.27 (2H, m), 1.84(2H, m)

MP: 201–203° C.

EXAMPLE 7

Methyl 2-({4-[4-(7-chloro-2-oxo-2H-3,1-benzoxazin-1(4H)-yl)piperidin-1-yl]-3-nitrophenyl}carbonyl)benzoate

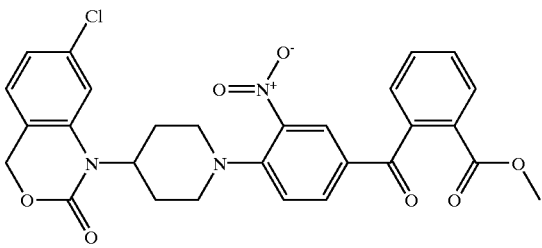

(i) 1,1-Dimethylethyl 4-{[5-chloro-2-(hydroxymethyl)phenyl]amino}piperidine-1-carboxylate

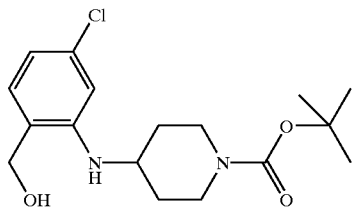

N-tert-Butoxycarbonyl-4-piperidone (5.8 g), 2-amino-5-chlorobenzyl alcohol (5.02 g) and acetic acid (4 ml) in toluene (200 ml) were heated under reflux using a Dean-Stark trap for 1.5 h. The solvent was evaporated under reduced pressure to ~100 ml, tetrahydrofuran (100 ml) added followed by sodium cyanoborohydride (6.3 g). Acetic acid (3 ml) was added dropwise to this mixture which was stirred at room temperature for 96 h. The solvents were removed under reduced pressure and the residue partitioned between ethyl acetate and aqueous sodium hydrogencarbonate solution. The organics were dried, evaporated under reduced pressure and the residue triturated with dichloromethane/isohexane. Yield 7.5 g.

MS: APCI(+ve) 500(M+1)

(ii) 7-Chloro-1-piperidin-4-yl-1,4-dihydro-2H-3,1-benzoxazin-2-one hydrochloride

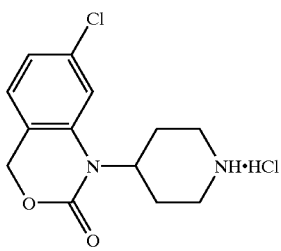

Triphosgene (1.6 g) was added to a stirred solution of the product from step (i) (5 g), N,N-diisopropylethylamine (5.2 ml) in tetrahydrofuran (50 ml) at 0° C. The mixture was stirred at room temperature for 16 h, the precipitate filtered and the filtrate evaporated under reduced pressure. Purification was by chromatography eluting with 20% ethyl acetate/toluene. The product was dissolved in dichloromethane then a solution of hydrogen chloride in 1,4-dioxane added. After 2 h the solvent was removed under reduced pressure to yield a solid. Used directly.

(iii) Methyl 2-({4-[4-(7-chloro-2-oxo-2H-3,1-benzoxazin-1(4H)-yl)piperidin-1-yl]-3-nitrophenyl}carbonyl)benzoate Methyl 2-[(4-chloro-3-nitrophenyl)carbonyl]benzoate (0.5 g), the product from step (ii) (0.47 g) and triethylamine (0.5 ml) in N,N-dimethylformamide (2.5 ml) were heated at 60° C. overnight. The mixture was evaporated under reduced pressure and the residue purified by chromatography eluting with 25% ethyl acetate/toluene. Yield 0.7 g of a solid.

MS: APCI(+ve) 550(M+1)

1H NMR: δ (DMSO-d6) 8.00–7.97(2H, m), 7.80–7.72 (2H, m), 7.70–7.65(1H, m), 7.46(1H, d), 7.40–7.30(4H, m), 5.12(2H, s), 4.20–4.10(1H, m), 3.64(3H, s), 3.49(2H, br d), 3.26(2H, br t), 2.70–2.60(2H, m), 1.97–1.91(2H, m)

MP: 90–2° C.

EXAMPLES 8–114

(i) 3-Nitro-4-[4-(2-oxo-2H-3,1-benzoxazin-1(4H)-yl)piperidin-1-yl]benzoic acid

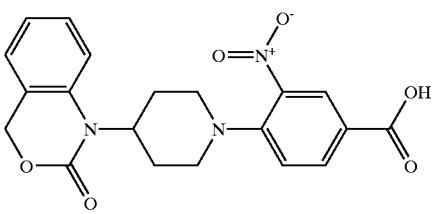

A solution of 1-piperidin-4-yl-1,4-dihydro-2H-3,1-benzoxazin-2-one hydrochloride (1.0 g), 1,1-dimethylethyl 4-chloro-3-nitrobenzoate (0.95 g) and triethylamine (0.8 g) in N,N-dimethylformamide (10 ml) was stirred at room temperature overnight. The mixture was partitioned between ethyl acetate and water. The organic layer was dried, and evaporated under reduced pressure. Purification was by chromatography eluting with 1:2 ethyl acetate-isohexane. The residue was dissolved in formic acid (5 ml) stirred overnight at room temperature, heated at 55° C. for 2 h, then evaporated under reduced pressure. The residue was triturated with ether, yield 0.85 g as a solid.

MS: APCI(+ve) 398(M+1)

(ii) Examples 8–114

Carbonyldiimidazole (0.2 g) was added to a solution of the product from step (i) (0.4 g) in N,N-dimethylformamide (25 ml) and stirred at room temperature for 2.5 h. The activated acid (0.1 ml) the appropriate amine (5 equivalents) and triethylamine (5 equivalents) in 1-methyl-2-pyrrolidinone (0.1 ml) were left at room temperature for 24 h. The reaction mixture was evaporated to dryness and the residue dissolved in dimethylsulphoxide (0.4 ml).

EXAMPLE 8

N-(1,1-Dimethylethyl)-3-nitro-4-[4-(2-oxo-2H-3,1-benzoxazin-1(4H)-yl)piperidin-1-yl]benzamide

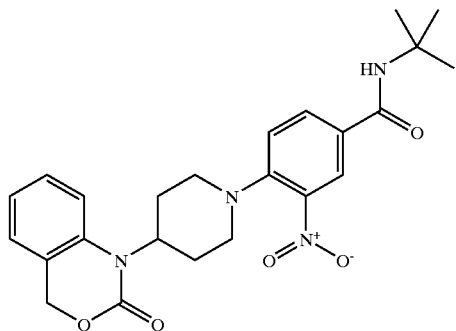

MS: APCI(+ve) 453(M+1)

EXAMPLE 9

N-[(1R)-2-Hydroxy-1-(phenylmethyl)ethyl]-3-nitro-4-[4-(2-oxo-2H-3,1-benzoxazin-1(4H)-yl)piperidin-1-yl]benzamide

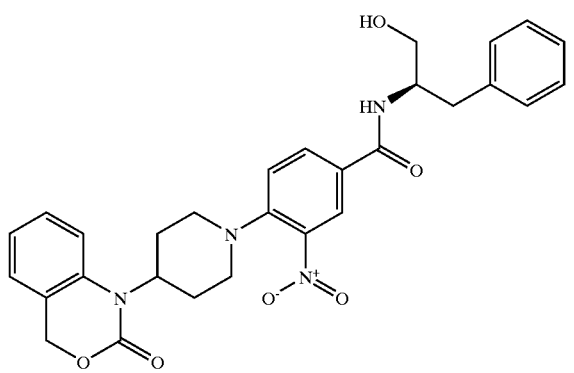

MS: APCI(+ve) 531(M+1)

EXAMPLE 10

Methyl 2-[({3-nitro-4-[4-(2-oxo-2H-3,1-benzoxazin-1(4H)-yl)piperidin-1-yl]phenyl}carbonyl)amino]propanoate

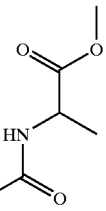

MS: APCI(+ve) 483(M+1)

EXAMPLE 11

3-Nitro-4-[4-(2-oxo-2H-3,1-benzoxazin-1(4H)-yl)piperidin-1-yl]-N-(tetrahydrofuran-2-ylmethyl)benzamide

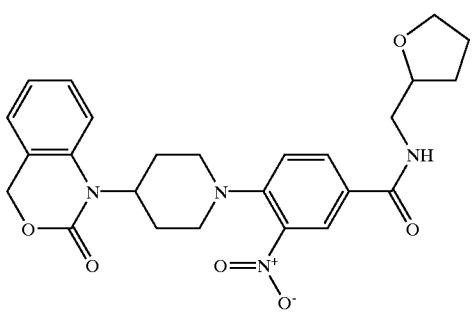

MS: APCI(+ve) 481(M+1)

EXAMPLE 12

N-[2-(4-Aminophenyl)ethyl]-3-nitro-4-[4-(2-oxo-2H-3,1-benzoxazin-1(4H)-yl)piperidin-1-yl]benzamide

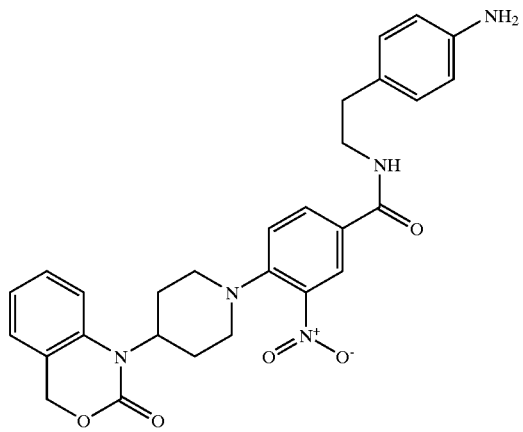

MS: APCI(+ve) 516(M+1)

EXAMPLE 13

3-Nitro-4-[4-(2-oxo-2H-3,1-benzoxazin-1(4H)-yl)piperidin-1-yl]-N-(2,2,2-trifluoroethyl)benzamide

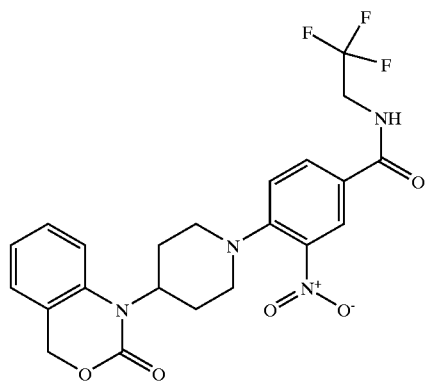

MS: APCI(+ve) 479(M+1)

EXAMPLE 14

Ethyl (2S)-3-methyl-2-[({3-nitro-4-[4-(2-oxo-2H-3,1-benzoxazin-1(4H)-yl)piperidin-1-yl]phenyl}carbonyl)amino]butanoate

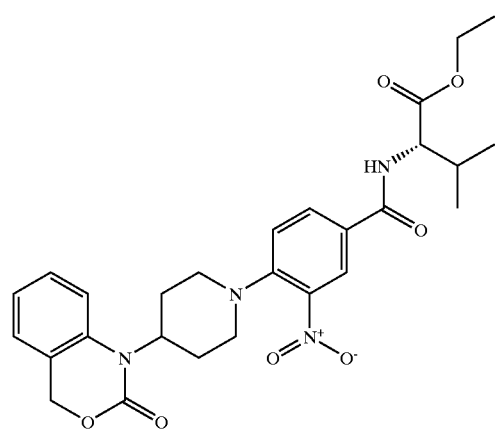

MS: APCI(+ve) 525(M+1)

EXAMPLE 15

Methyl 3-hydroxy-2-[({3-nitro-4-[4-(2-oxo-2H-3,1-benzoxazin-1(4H)-yl)piperidin-1-yl]phenyl}carbonyl)amino]propanoate

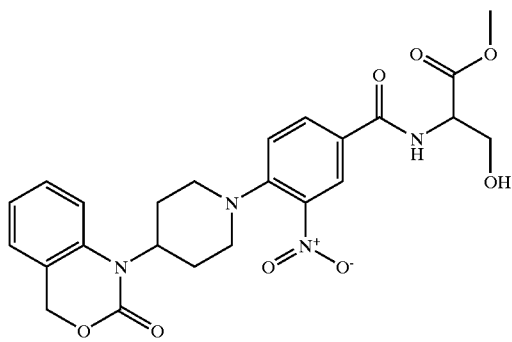

MS: APCI(+ve) 499(M+1)

EXAMPLE 16

N-[2-(3,4-Dihydroxyphenyl)ethyl]-3-nitro-4-[4-(2-oxo-2H-3,1-benzoxazin-1(4H)-yl)piperidin-1-yl]benzamide

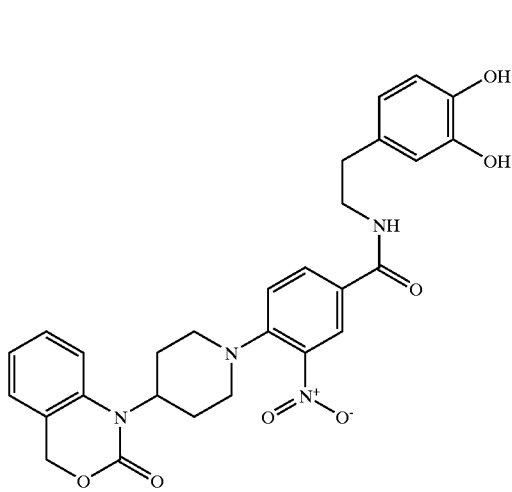

MS: APCI(+ve) 533(M+1)

EXAMPLE 17

3-Nitro-4-[4-(2-oxo-2H-3,1-benzoxazin-1(4H)-yl)piperidin-1-yl]-N-(2-phenylethyl)benzamide

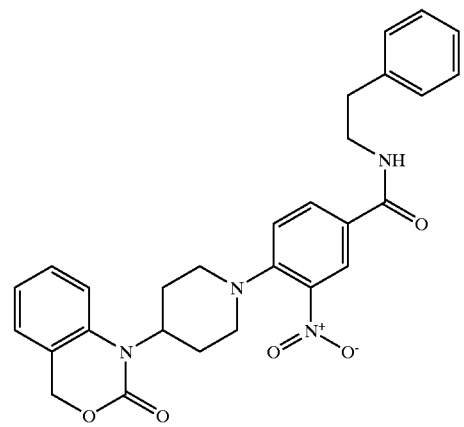

MS: APCI(+ve) 501(M+1)

EXAMPLE 18

N-[(4-Aminophenyl)methyl]-3-nitro-4-[4-(2-oxo-2H-3,1-benzoxazin-1(4H)-yl)piperidin-1-yl]benzamide

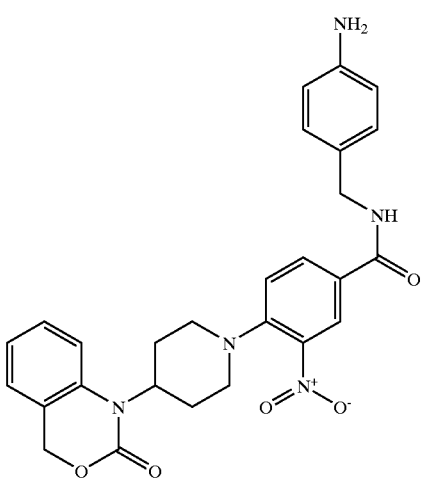

MS: APCI(+ve) 502(M+1)

EXAMPLE 19

3-Nitro-4-[4-(2-oxo-2H-3,1-benzoxazin-1(4H)-yl)piperidin-1-yl]-N-(2-thien-2-ylethyl)benzamide

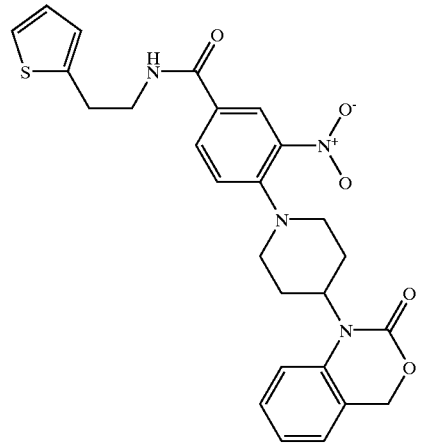

MS: APCI(+ve) 507(M+1)

EXAMPLE 20

N-[3-(Dimethylamino)-2,2-dimethylpropyl]-3-nitro-4-[4-(2-oxo-2H-3,1-benzoxazin-1(4H)-yl)piperidin-1-yl]benzamide

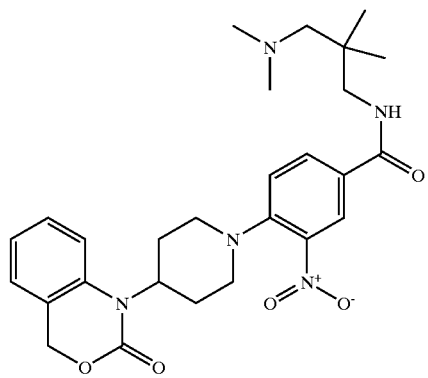

MS: APCI(+ve) 510(M+1)

EXAMPLE 21

N-{[2,4-Bis(methyloxy)phenyl]methyl}-3-nitro-4-[4-(2-oxo-2H-3,1-benzoxazin-1(4H)-yl)piperidin-1-yl]benzamide

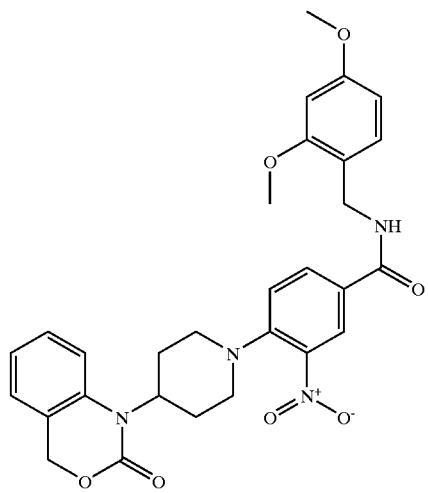

MS: APCI(+ve) 547(M+1)

EXAMPLE 22

N-Bicyclo[2.2.1]hept-2-yl-3-nitro-4-[4-(2-oxo-2H-3,1-benzoxazin-1(4H)-yl)piperidin-1-yl]benzamide

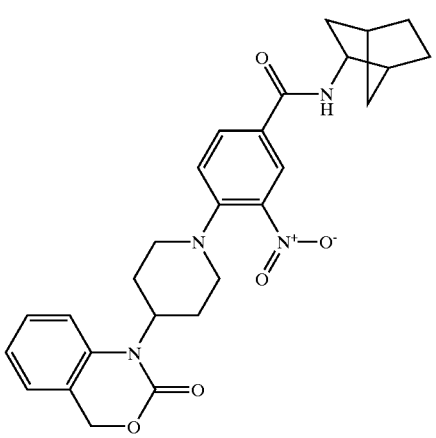

MS: APCI(+ve) 491(M+1)

EXAMPLE 23

N-(2-Fluoroethyl)-3-nitro-4-[4-(2-oxo-2H-3,1-benzoxazin-1(4H)-yl)piperidin-1-yl]benzamide

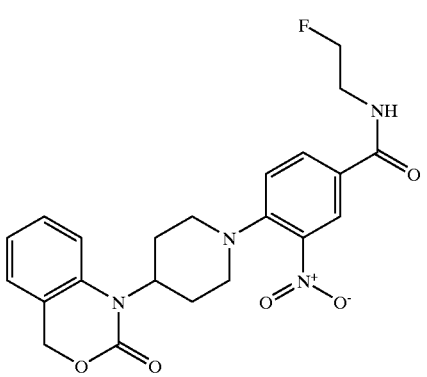

MS: APCI(+ve) 443 (M+1)

EXAMPLE 24

3-Nitro-N-[(3-nitrophenyl)methyl]-4-[4-(2-oxo-2H-3,1-benzoxazin-1(4H)-yl)piperidin-1-yl]benzamide

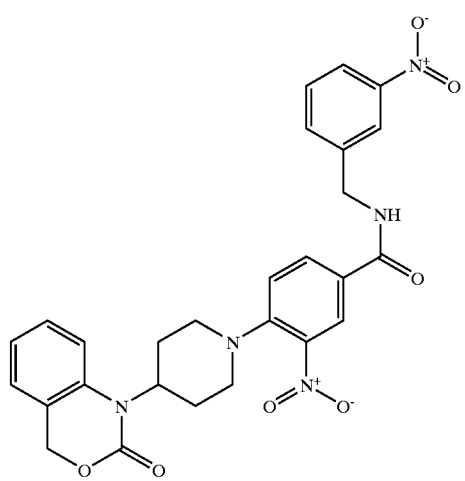

MS: APCI(+ve) 532(M+1)

EXAMPLE 25

N-[(1S,2R)-2-Hydroxy-1-methyl-2-phenylethyl]-3-nitro-4-[4-(2-oxo-2H-3,1-benzoxazin-1(4H)-yl)piperidin-1-yl]benzamide

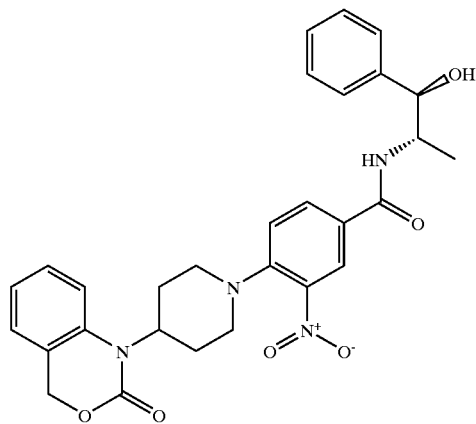

MS: APCI(+ve) 531(M+1)

EXAMPLE 26

3-Nitro-4-[4-(2-oxo-2H-3,1-benzoxazin-1(4H)-yl)piperidin-1-yl]-N-{[3,4,5-tris(methyloxy)phenyl]methyl}benzamide

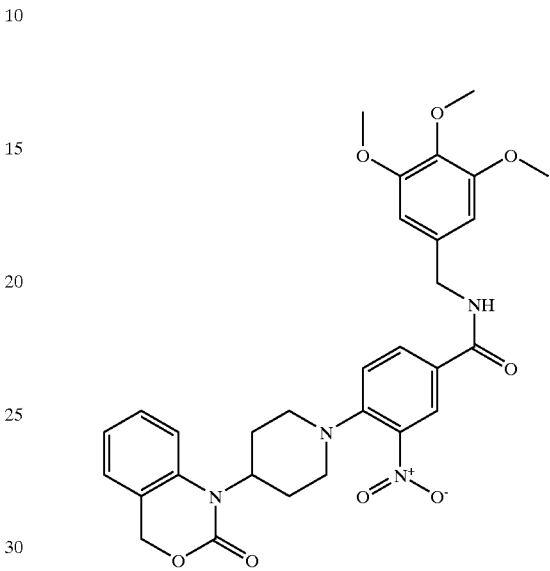

MS: APCI(+ve) 577(M+1)

EXAMPLE 27

3-Nitro-4-[4-(2-oxo-2H-3,1-benzoxazin-1(4H)-yl)piperidin-1-yl]-N-(2-phenylcyclopropyl)benzamide

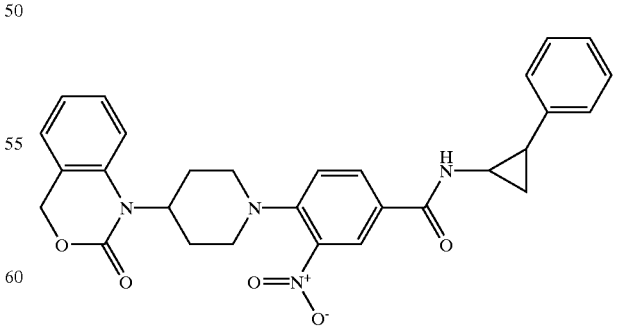

MS: APCI(+ve) 513(M+1)

EXAMPLE 28

N-[2-Hydroxy-1-(hydroxymethyl)-1-methylethyl]-3-nitro-4-[4-(2-oxo-2H-3,1-benzoxazin-1(4H)-yl)piperidin-1-yl]benzamide

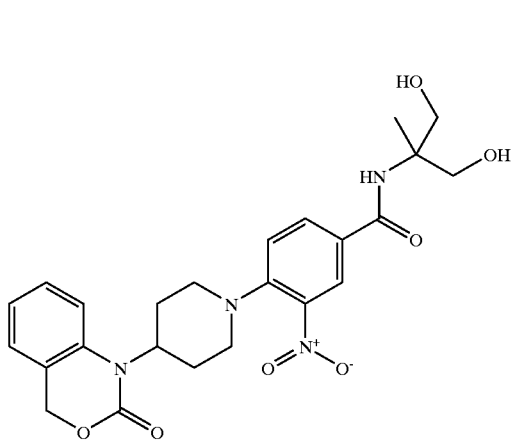

MS: APCI(+ve) 485(M+1)

EXAMPLE 29

N-(1-Azabicyclo[2.2.2]oct-3-yl)-3-nitro-4-[4-(2-oxo-2H-3,1-benzoxazin-1(4H)-yl)piperidin-1-yl]benzamide

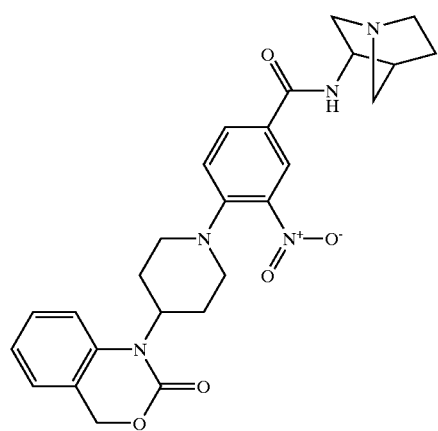

MS: APCI(+ve) 506(M+1)

EXAMPLE 30

3-Nitro-4-[4-(2-oxo-2H-3,1-benzoxazin-1(4H)-yl)piperidin-1-yl]-N-(2-piperidin-1-ylethyl)benzamide

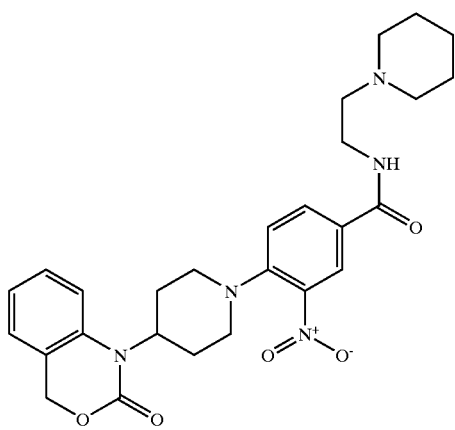

MS: APCI(+ve) 508(M+1)

EXAMPLE 31

N-(1,3-Dimethylbutyl)-3-nitro-4-[4-(2-oxo-2H-3,1-benzoxazin-1(4H)-yl)piperidin-1-yl]benzamide

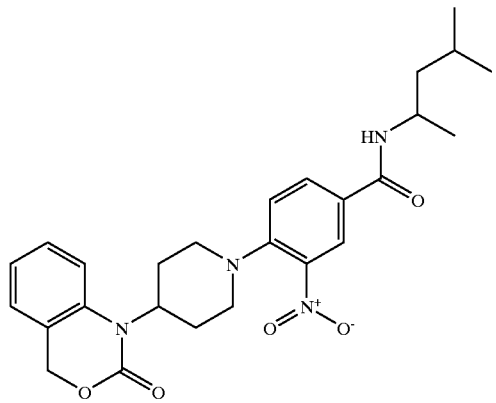

MS: APCI(+ve) 481(M+1)

EXAMPLE 32
N-(1-Methylbutyl)-3-nitro-4-[4-(2-oxo-2H-3,1-benzoxazin-1(4H)-yl)piperidin-1-yl]benzamide
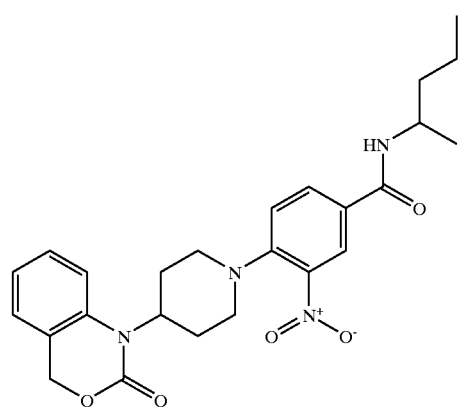
MS: APCI(+ve) 467(M+1)
EXAMPLE 33
N-(1-Methylhexyl)-3-nitro-4-[4-(2-oxo-2H-3,1-benzoxazin-1(4H)-yl)piperidin-1-yl]benzamide
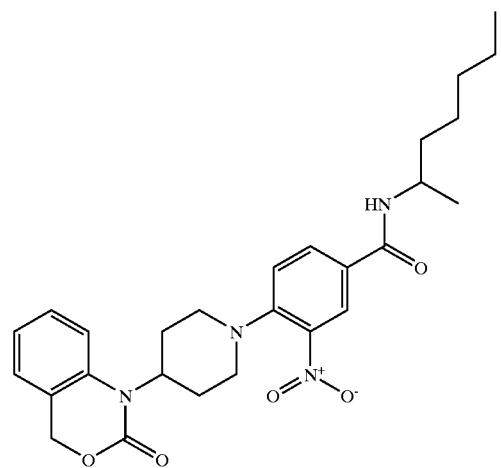
MS: APCI(+ve) 495(M+1)
EXAMPLE 34
N-(3-Methylbutyl)-3-nitro-4-[4-(2-oxo-2H-3,1-benzoxazin-1(4H)-yl)piperidin-1-yl]benzamide
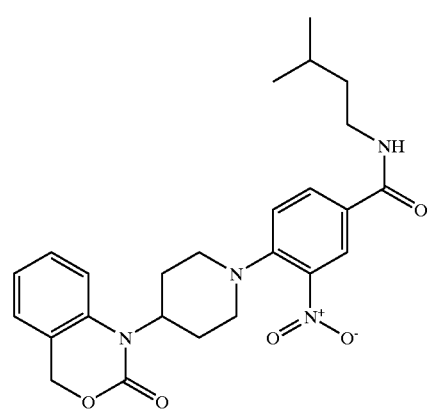
MS: APCI(+ve) 467(M+1)
EXAMPLE 35
N-[(2-Aminophenyl)methyl]-3-nitro-4-[4-(2-oxo-2H-3,1-benzoxazin-1(4H)-yl)piperidin-1-yl]benzamide
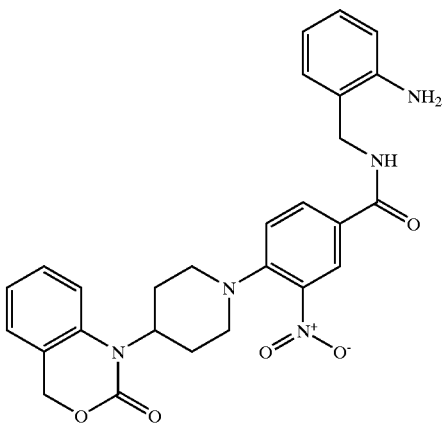
MS: APCI(+ve) 502(M+1)

EXAMPLE 36

N-[2-Hydroxy-1-(hydroxymethyl)ethyl]-3-nitro-4-[4-(2-oxo-2H-3,1-benzoxazin-1(4H)-yl)piperidin-1-yl]benzamide

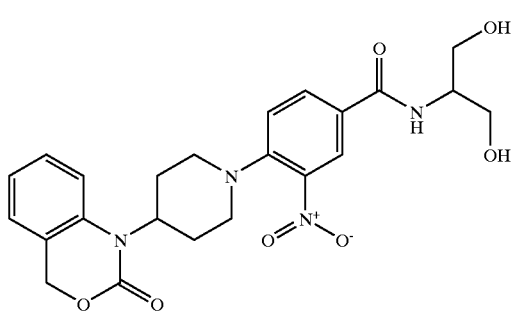

MS: APCI(+ve) 471(M+1)

EXAMPLE 37

N-[2-(Ethylthio)ethyl]-3-nitro-4-[4-(2-oxo-2H-3,1-benzoxazin-1(4H)-yl)piperidin-1-yl]benzamide

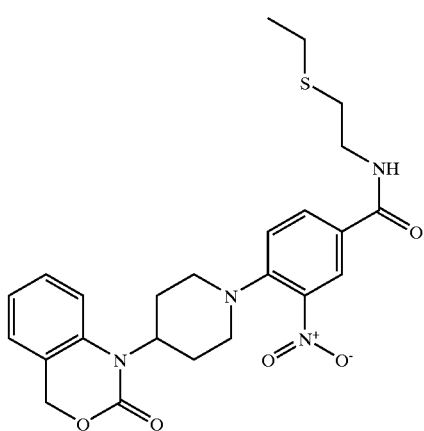

MS: APCI(+ve) 485(M+1)

EXAMPLE 38

N-[(1S)-1-(Hydroxymethyl)-2,2-dimethylpropyl]-3-nitro-4-[4-(2-oxo-2H-3,1-benzoxazin-1(4H)-yl)piperidin-1-yl]benzamide

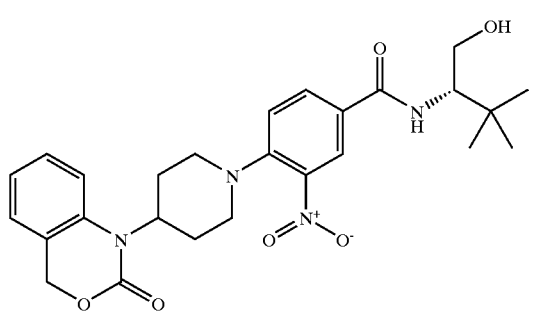

MS: APCI(+ve) 497(M+1)

EXAMPLE 39

N-(4-Methylcyclohexyl)-3-nitro-4-[4-(2-oxo-2H-3,1-benzoxazin-1(4H)-yl)piperidin-1-yl]benzamide

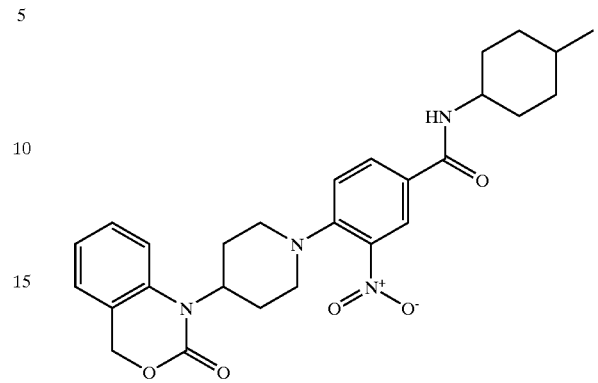

MS: APCI(+ve) 493(M+1)

EXAMPLE 40

N-{2-Hydroxy-1-[(methyloxy)methyl]-2-phenylethyl}-3-nitro-4-[4-(2-oxo-2H-3,1-benzoxazin-1(4H)-yl)piperidin-1-yl]benzamide

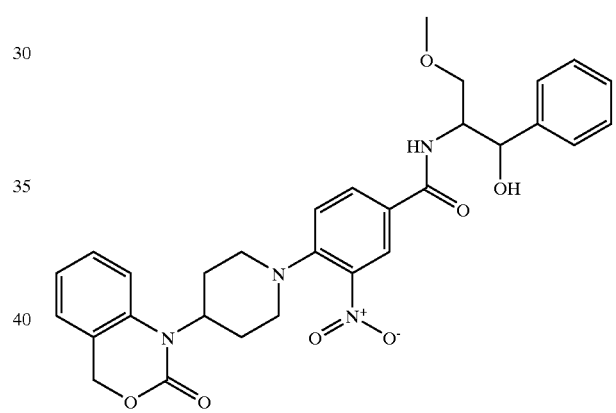

MS: APCI(+ve) 561(M+1)

EXAMPLE 41

N-Ethyl-3-nitro-4-[4-(2-oxo-2H-3,1-benzoxazin-1(4H)-yl)piperidin-1-yl]benzamide

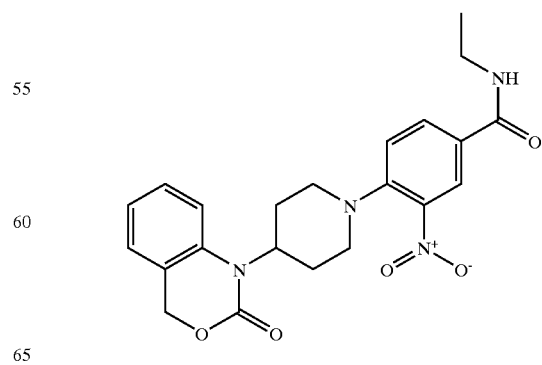

MS: APCI(+ve) 425(M+1)

EXAMPLE 42

N-Cyclopropyl-3-nitro-4-[4-(2-oxo-2H-3,1-benzoxazin-1(4H)-yl)piperidin-1-yl]benzamide

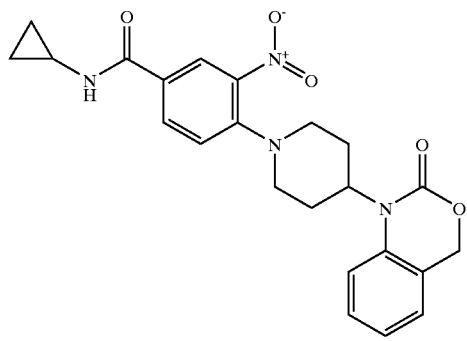

MS: APCI(+ve) 437(M+1)

EXAMPLE 43

3-Nitro-4-[4-(2-oxo-2H-3,1-benzoxazin-1(4H)-yl)piperidin-1-yl]-N-(phenylmethyl)benzamiide

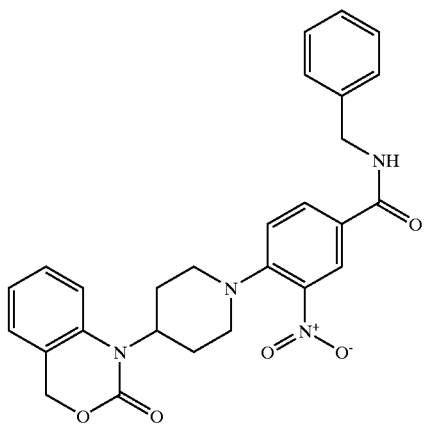

MS: APCI(+ve) 487(M+1)

EXAMPLE 44

N-(1-Methylpropyl)-3-nitro-4-[4-(2-oxo-2H-3,1-benzoxazin-1(4H)-yl)piperidin-1-yl]benzamide

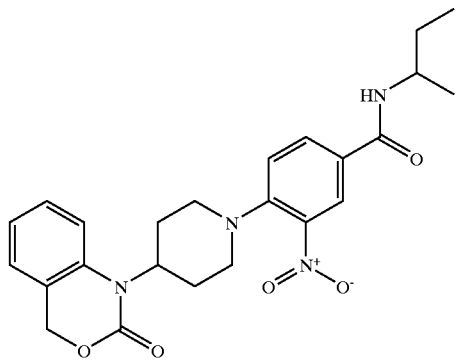

MS: APCI(+ve) 453(M+1)

EXAMPLE 45

1,1-Dimethylethyl 2-[({3-nitro-4-[4-(2-oxo-2H-3,1-benzoxazin-1(4H)-yl)piperidin-1-yl]phenyl}carbonyl)anino]ethylcarbamate

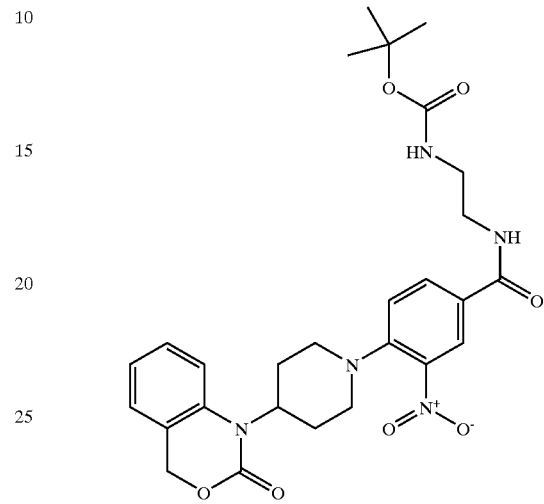

MS: APCI(+ve) 440(M+1-Boc)

EXAMPLE 46

N-[2-(3,4-Dihydroxyphenyl)ethyl]-3-nitro-4-[4-(2-oxo-2H-3,1-benzoxazin-1(4H)-yl)piperidin-1-yl]benzamide

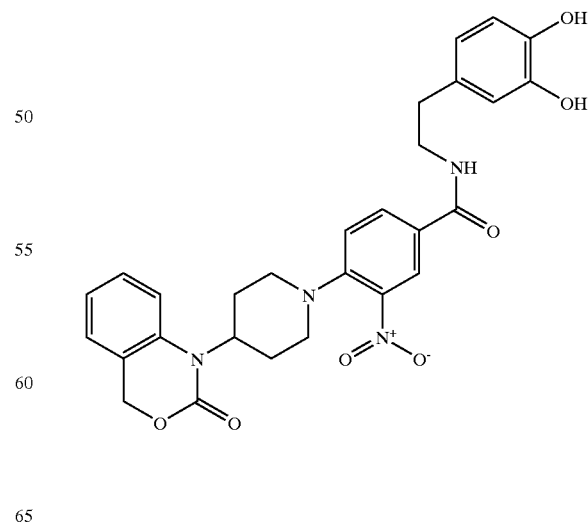

MS: APCI(+ve) 533(M+1)

EXAMPLE 47

N-{[4-(Methyloxy)phenyl]methyl}-3-nitro-4-[4-(2-oxo-2H-3,1-benzoxazin-1(4H)-yl)piperidin-1-yl]benzamide

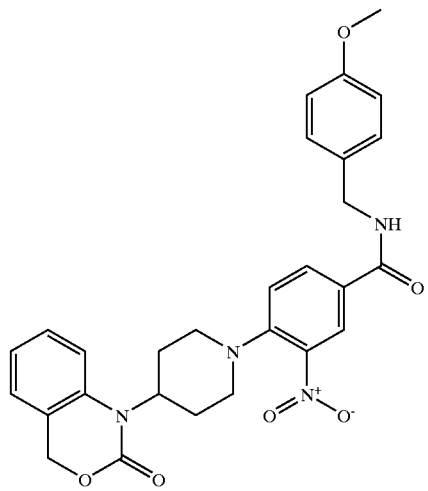

MS: APCI(+ve) 517(M+1)

EXAMPLE 48

N-[2-(1H-Imidazol-4-yl)ethyl]-3-nitro-4-[4-(2-oxo-2H-3,1-benzoxazin-1(4H)-yl)piperidin-1-yl]benzamide

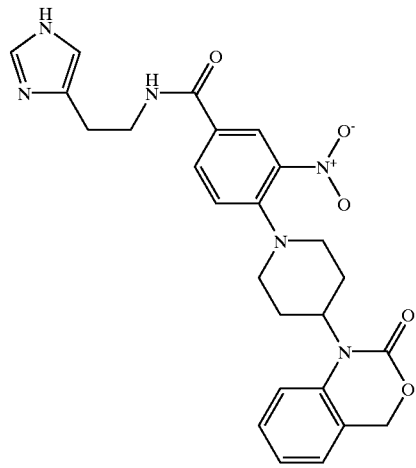

MS: APCI(+ve) 491(M+1)

EXAMPLE 49

N-[(1S)-1-(Hydroxymethyl)propyl]-3-nitro-4-[4-(2-oxo-2H-3,1-benzoxazin-1(4H)-yl)piperidin-1-yl]benzamide

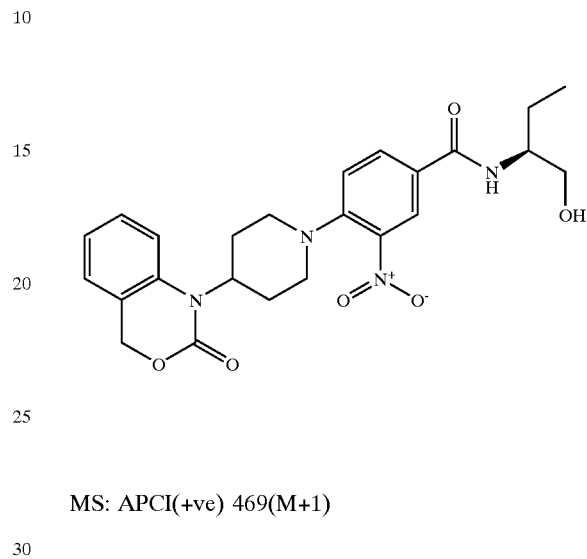

MS: APCI(+ve) 469(M+1)

EXAMPLE 50

3-Nitro-4-[4-(2-oxo-2H-3,1-benzoxazin-1(4H)-yl)piperidin-1-yl]-N-[1-(phenylmethyl)piperidin-4-yl]benzamide

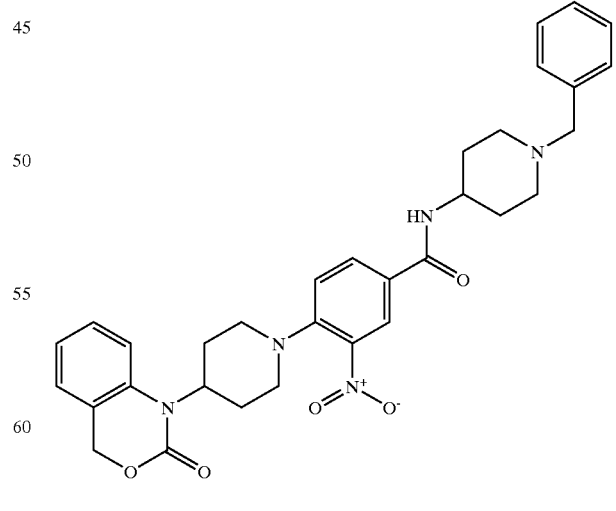

MS: APCI(+ve) 570(M+1)

EXAMPLE 51

N-[(1R)-1-(Hydroxymethyl)propyl]-3-nitro-4-[4-(2-oxo-2H-3,1-benzoxazin-1(4H)-yl)piperidin-1-yl]benzamide

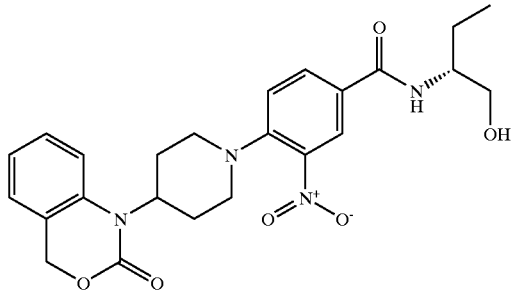

MS: APCI(+ve) 469(M+1)

EXAMPLE 52

N-(4-Hydroxybutyl)-3-nitro-4-[4-(2-oxo-2H-3,1-benzoxazin-1(4H)-yl)piperidin-1-yl]benzamide

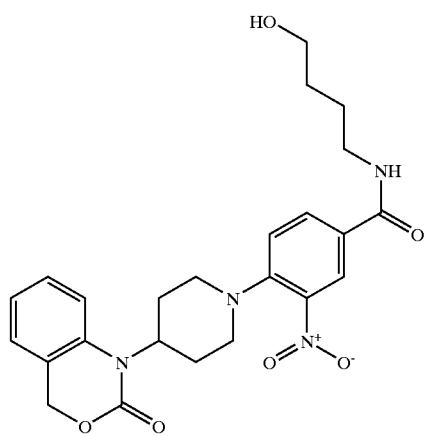

MS: APCI(+ve) 469(M+1)

EXAMPLE 53

3-Nitro-4-[4-(2-oxo-2H-3,1-benzoxazin-1(4H)-yl)piperidin-1-yl]-N-tricyclo[3.3.1.1~3,7~]dec-1-ylbenzamide

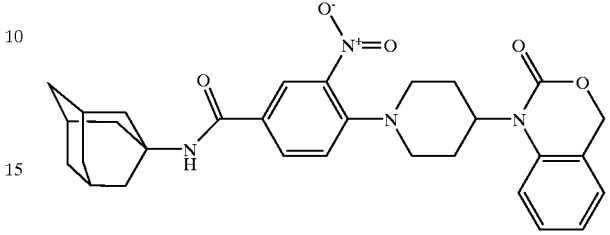

MS: APCI(+ve) 531(M+1)

EXAMPLE 54

N-[(1S,2S)-2-Hydroxycyclohexyl]-3-nitro-4-[4-(2-oxo-2H-3,1-benzoxazin-1(4H)-yl)piperidin-1-yl]benzamide

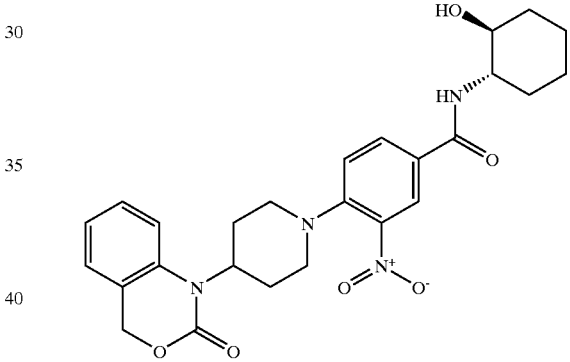

MS: APCI(+ve) 495(M+1)

EXAMPLE 55

N-(2-Hydroxy-1-methylethyl)-3-nitro-4-[4-(2-oxo-2H-3,1-benzoxazin-1(4H)-yl)piperidin-1-yl]benzamide

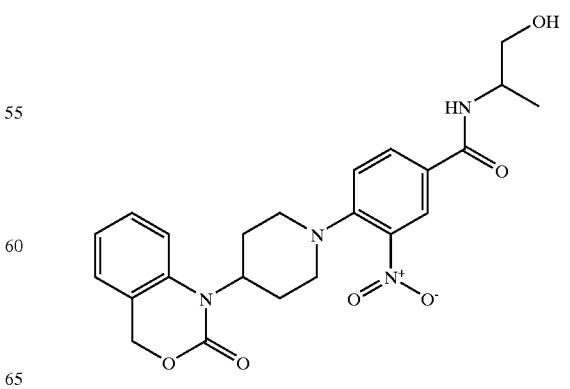

MS: APCI(+ve) 455(M+1)

EXAMPLE 56

N-{2-[(2-Hydroxyethyl)oxy]ethyl}-3-nitro-4-[4-(2-oxo-2H-3,1-benzoxazin-1(4H)-yl)piperidin-1-yl]benzamide

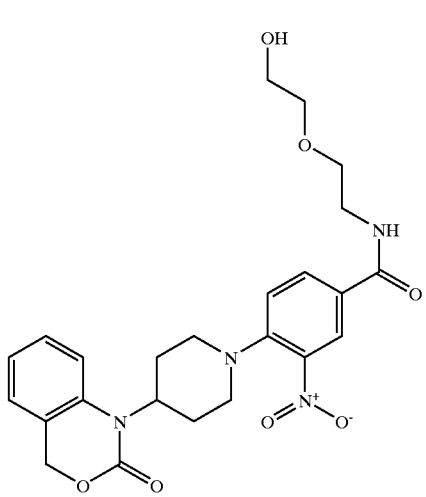

MS: APCI(+ve) 485(M+1)

EXAMPLE 57

N-[1-(Hydroxymethyl)butyl]-3-nitro-4-[4-(2-oxo-2H-3,1-benzoxazin-1(4H)-yl)piperidin-1-yl]benzamide

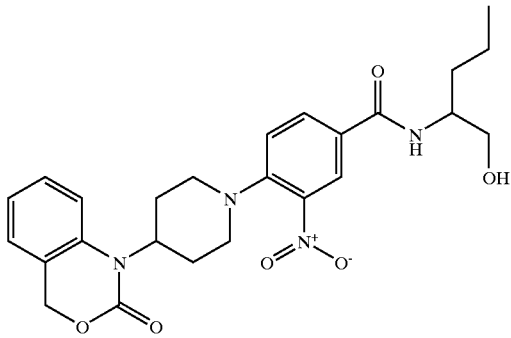

MS: APCI(+ve) 483(M+1)

EXAMPLE 58

N-(2-Amino-2-oxoethyl)-3-nitro-4-[4-(2-oxo-2H-3,1-benzoxazin-1(4H)-yl)piperidin-1-yl]benzamide

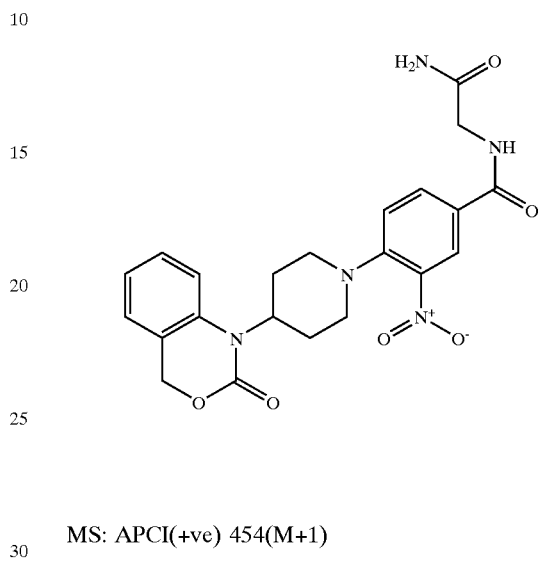

MS: APCI(+ve) 454(M+1)

EXAMPLE 59

N-[1-(4-Fluorophenyl)ethyl]-3-nitro-4-[4-(2-oxo-2H-3,1-benzoxazin-1(4H)-yl)piperidin-1-yl]benzamide

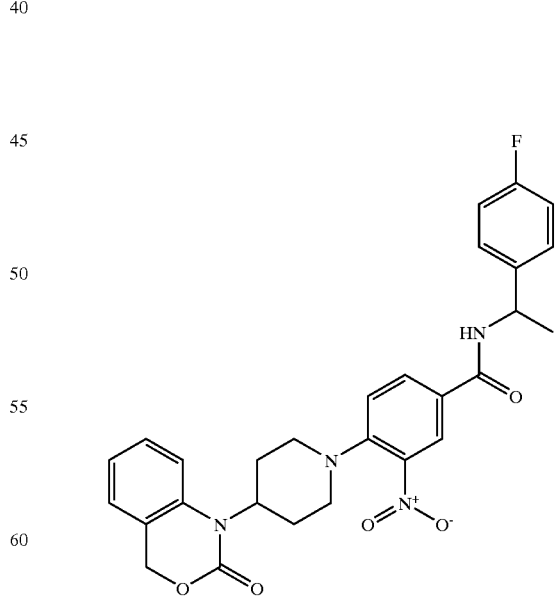

MS: APCI(+ve) 519(M+1)

EXAMPLE 60

3-Nitro-4-[4-(2-oxo-2H-3,1-benzoxazin-1(4H)-yl)piperidin-1-yl]-N-(3-phenylpropyl)benzamide

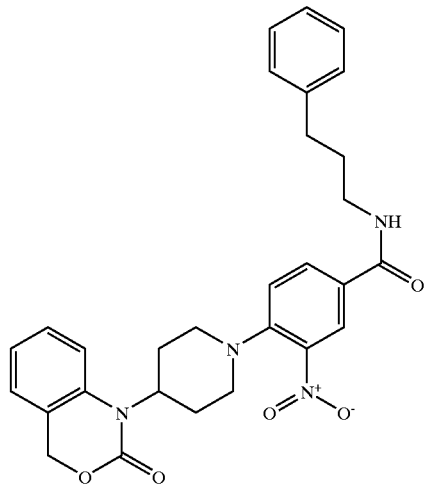

MS: APCI(+ve) 515(M+1)

EXAMPLE 61

N-[(1S,2R)-2-Hydroxycyclohexyl]-3-nitro-4-[4-(2-oxo-2H-3,1-benzoxazin-1(4H)-yl)piperidin-1-yl]benzamide

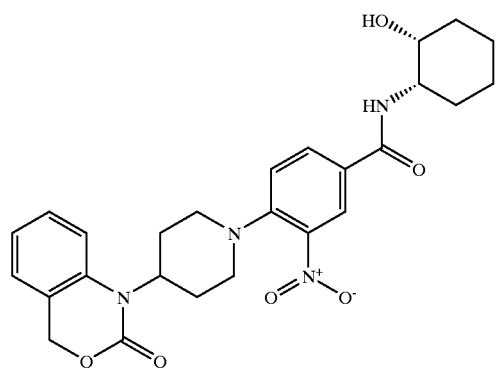

MS: APCI(+ve) 495(M+1)

EXAMPLE 62

Ethyl 3-hydroxy-2-[({3-nitro-4-[4-(2-oxo-2H-3,1-benzoxazin-1(4H)-yl)piperidin-1-yl]phenyl}carbonyl)amino]propanoate

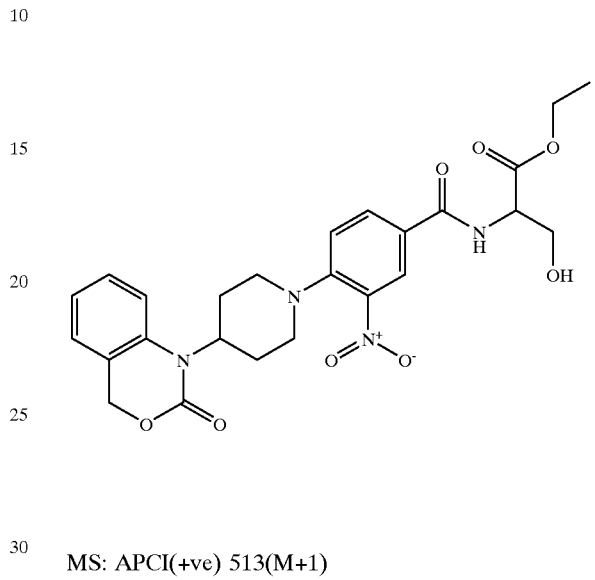

MS: APCI(+ve) 513(M+1)

EXAMPLE 63

N-[(1R,2S)-2-Hydroxy-1-methyl-2-phenylethyl]-3-nitro-4-[4-(2-oxo-2H-3,1-benzoxazin-1(4H)-yl)piperidin-1-yl]benzamide

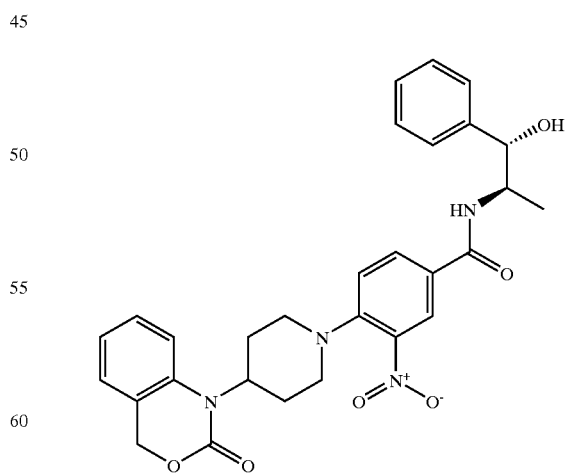

MS: APCI(+ve) 531(M+1)

EXAMPLE 64

1-{1-[4-(Morpholin-4-ylcarbonyl)-2-nitrophenyl]piperidin-4-yl}-1,4-dihydro-2H-3,1-benzoxazin-2-one

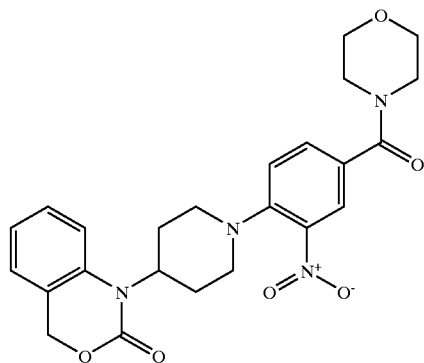

MS: APCI(+ve) 467(M+1)

EXAMPLE 65

N,N-Dimethyl-3-nitro-4-[4-(2-oxo-2H-3,1-benzoxazin-1(4H)-yl)piperidin-1-yl]benzamide

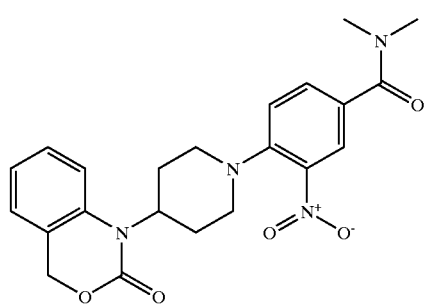

MS: APCI(+ve) 425(M+1)

EXAMPLE 66

N,N-Bis(2-hydroxyethyl)-3-nitro-4-[4-(2-oxo-2H-3,1-benzoxazin-1(4H)-yl)piperidin-1-yl]benzamide

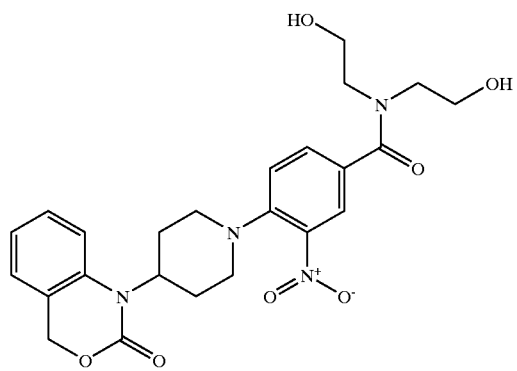

MS: APCI(+ve) 485 (M+1)

EXAMPLE 67

N-(2-Hydroxyethyl)-N-methyl-3-nitro-4-[4-(2-oxo-2H-3,1-benzoxazin-1(4H)-yl)piperidin-1-yl]benzamide

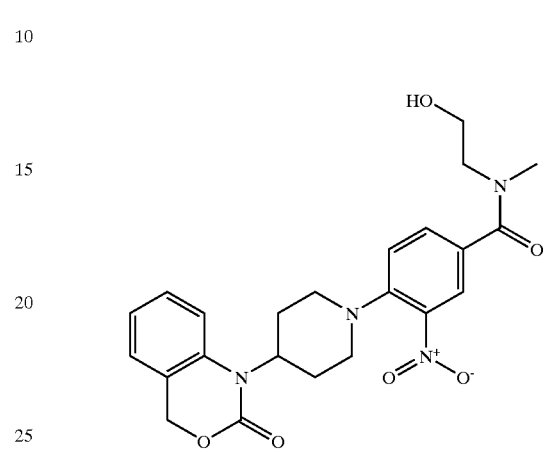

MS: APCI(+ve) 455(M+1)

EXAMPLE 68

N-(2-Hydroxyethyl)-3-nitro-4-[4-(2-oxo-2H-3,1-benzoxazin-1(4H)-yl)piperidin-1-yl]-N-(phenylmethyl)benzamide

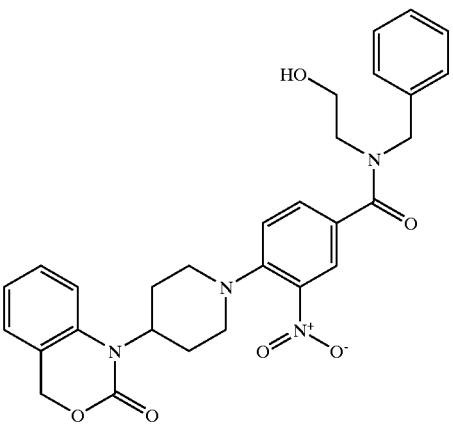

MS: APCI(+ve) 531 (M+1)

EXAMPLE 69

1-(1-{2-Nitro-4-[(4-phenylpiperazin-1-yl)carbonyl]phenyl}piperidin-4-yl)-1,4-dihydro-2H-3,1-benzoxazin-2-one

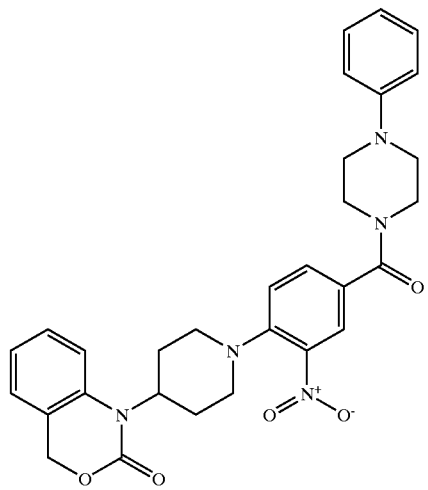

MS: APCI(+ve) 542(M+1)

EXAMPLE 70

N-[(1S,2R)-2-hydroxy-1-methyl-2-phenylethyl]-N-methyl-3-nitro-4-[4-(2-oxo-2H-3,1-benzoxazin-1(4H)-yl)piperidin-1-yl]benzamide

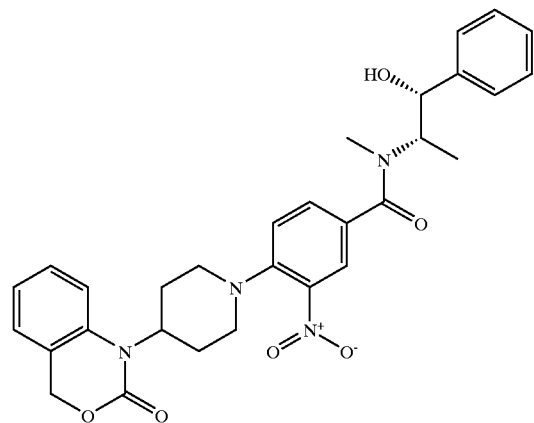

MS: APCI(+ve) 545(M+1)

EXAMPLE 71

N-Ethyl-N-(2-hydroxyethyl)-3-nitro-4-[4-(2-oxo-2H-3,1-benzoxazin-1(4H)-yl)piperidin-1-yl]benzamide

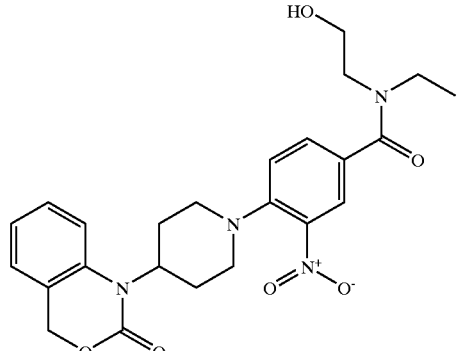

MS: APCI(+ve) 469(M+1)

EXAMPLE 72

1-[1-(4-{[4-(4-Fluorophenyl)piperazin-1-yl]carbonyl}-2-nitrophenyl)piperidin-4-yl]-1,4-dihydro-2H-3,1-benzoxazin-2-one

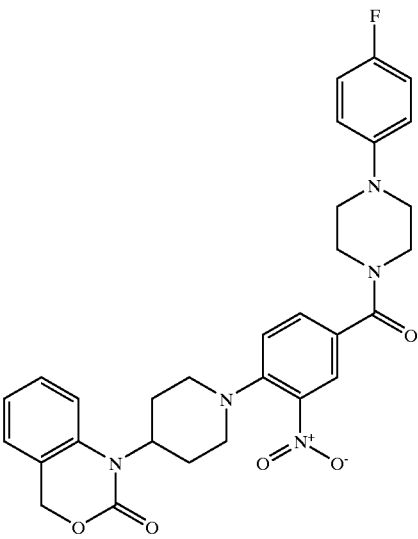

MS: APCI(+ve) 560(M+1)

EXAMPLE 73

1-{1-[4-(Azepan-1-ylcarbonyl)-2-nitrophenyl]piperidin-4-yl}-1,4-dihydro-2H-3,1-benzoxazin-2-one

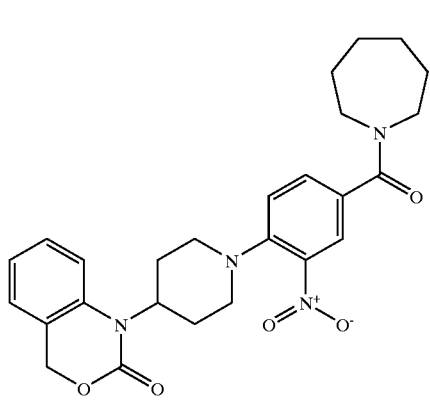

MS: APCI(+ve) 479(M+1)

EXAMPLE 74

N,N-Diethyl-3-nitro-4-[4-(2-oxo-2H-3,1-benzoxazin-1(4H)-yl)piperidin-1-yl]benzamide

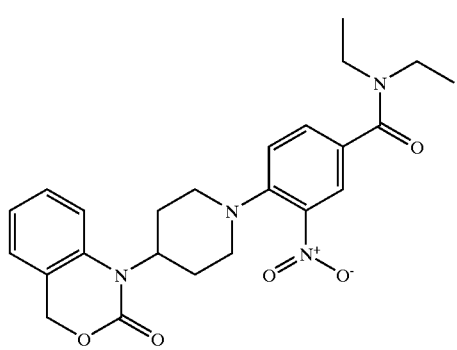

MS: APCI(+ve) 453(M+1)

EXAMPLE 75

N-[2-(Dimethylamino)ethyl]-3-nitro-4-[4-(2-oxo-2H-3,1-benzoxazin-1(4H)-yl)piperidin-1-yl]-N-(phenylmethyl)benzamide

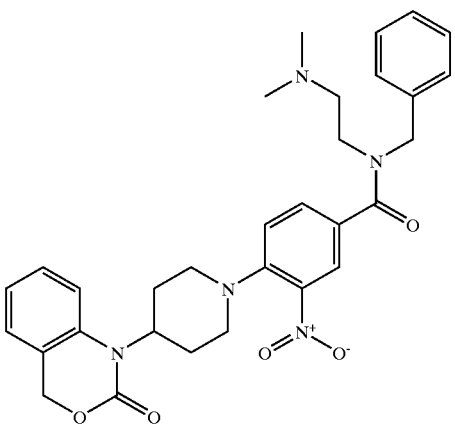

MS: APCI(+ve) 558(M+1)

EXAMPLE 76

N-Ethyl-3-nitro-4-[4-(2-oxo-2H-3,1-benzoxazin-1(4H)-yl)piperidin-1-yl]-N-(phenylmethyl)benzamide

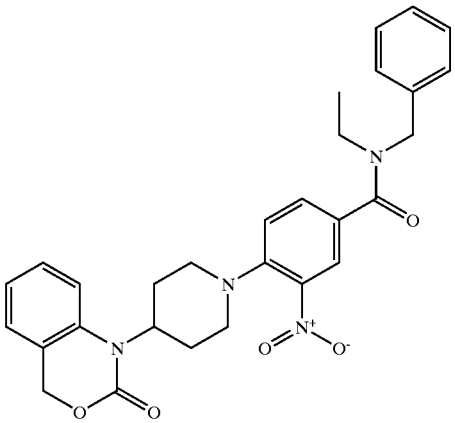

MS: APCI(+ve) 515(M+1)

EXAMPLE 77

N-Butyl-3-nitro-4-[4-(2-oxo-2H-3,1-benzoxazin-1(4H)-yl)piperidin-1-yl]-N-(phenylmethyl)benzamide

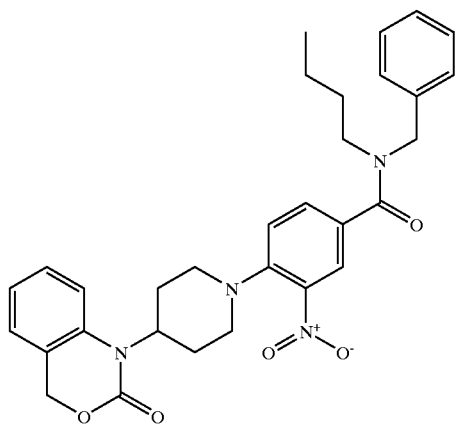

MS: APCI(+ve) 543(M+1)

EXAMPLE 78

1-{1-[2-Nitro-4-(piperidin-1-ylcarbonyl)phenyl]piperidin-4-yl}-1,4-dihydro-2H-3,1-benzoxazin-2-one

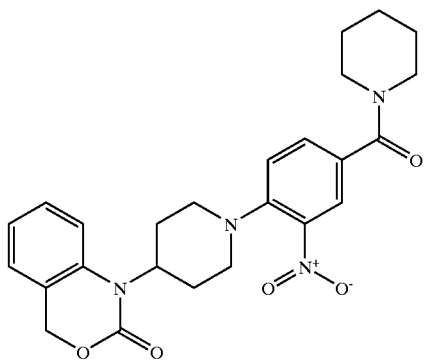

MS: APCI(+ve) 465(M+1)

EXAMPLE 79

Ethyl [({3-nitro-4-[4-(2-oxo-2H-3,1-benzoxazin-1(4H)-yl)piperidin-1-yl]phenyl}carbonyl)(phenylmethyl)amino]acetate

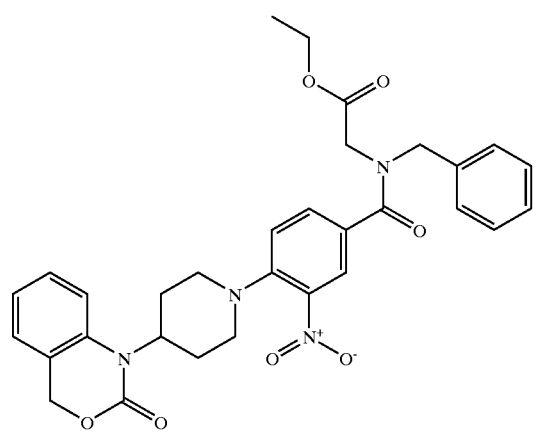

MS: APCI(+ve) 573(M+1)

EXAMPLE 80

N-(2-Hydroxyethyl)-N-(1-methylethyl)-3-nitro-4-[4-(2-oxo-2H-3,1-benzoxazin-1(4H)-yl)piperidin-1-yl]benzamide

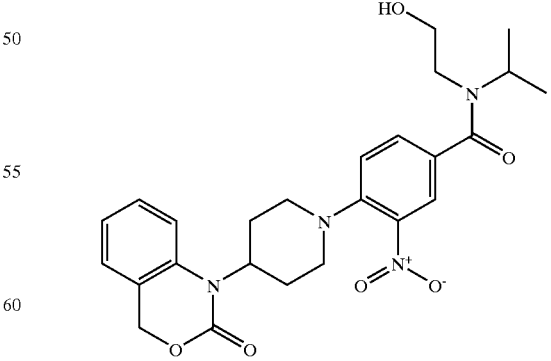

MS: APCI(+ve) 483(M+1)

EXAMPLE 81

1-(1-{2-Nitro-4-[(4-pyridin-2-ylpiperazin-1-yl)carbonyl]phenyl}piperidin-4-yl)-1,4-dihydro-2H-3,1-benzoxazin-2-one

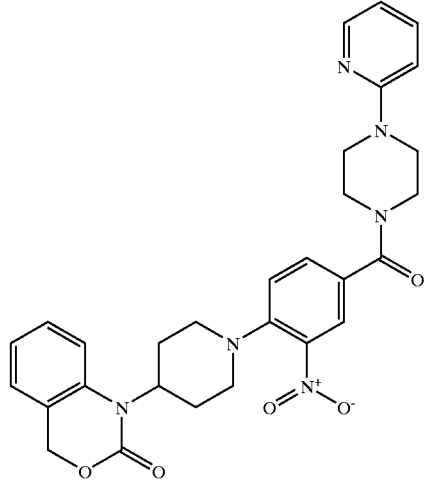

MS: APCI(+ve) 543(M+1)

EXAMPLE 82

1-{1-[2-Nitro-4-(pyrrolidin-1-ylcarbonyl)phenyl]piperidin-4-yl}-1,4-dihydro-2H-3,1-benzoxazin-2-one

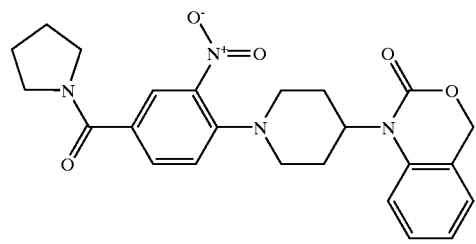

MS: APCI(+ve) 451(M+1)

EXAMPLE 83

N-(2-Hydroxyethyl)-3-nitro-4-[4-(2-oxo-2H-3,1-benzoxazin-1(4H)-yl)piperidin-1-yl]-N-pentylbenzamide

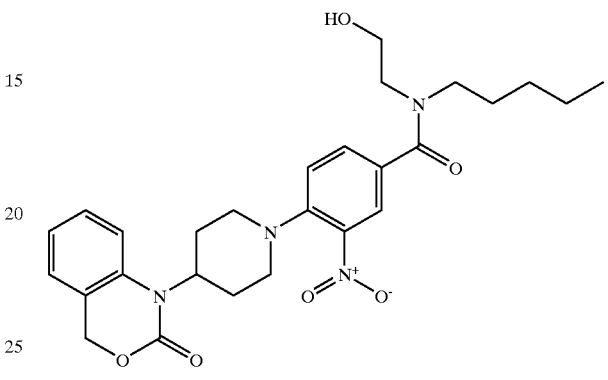

MS: APCI(+ve) 511(M+1)

EXAMPLE 84

N-[2-(Diethylamino)ethyl]-N-ethyl-3-nitro-4-[4-(2-oxo-2H-3,1-benzoxazin-1(4H)-yl)piperidin-1-yl]benzamide

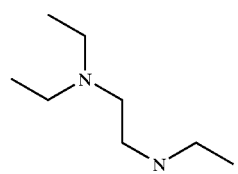

MS: APCI(+ve) 524(M+1)

EXAMPLE 85

N-Ethyl-N-methyl-3-nitro-4-[4-(2-oxo-2H-3,1-benzoxazin-1(4n)-yl)piperidin-1-yl]benzamide

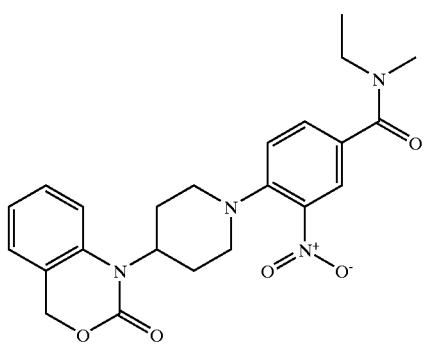

MS: APCI(+ve) 439(M+1)

EXAMPLE 86

(2S)-1-({3-Nitro-4-[4-(2-oxo-2H-3,1-benzoxazin-1(4H)-yl)piperidin-1-yl]phenyl}carbonyl)pyrrolidine-2-carboxamide

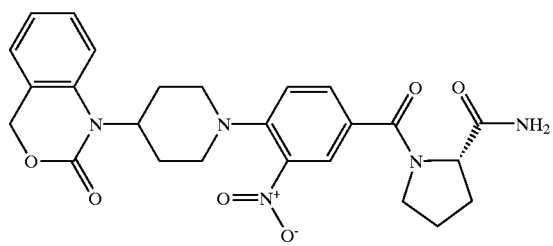

MS: APCI(+ve) 494(M+1)

EXAMPLE 87

N-(2-Cyanoethyl)-3-nitro-4-[4-(2-oxo-2H-3,1-benzoxazin-1(4H)-yl)piperidin-1-yl]-(phenylmethyl)benzamide

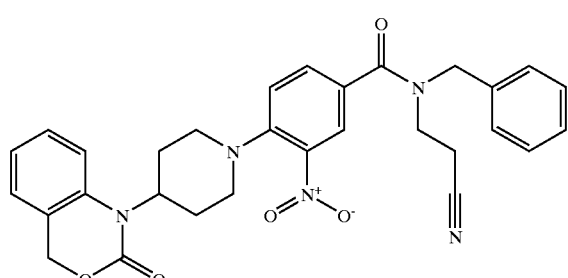

MS: APCI(+ve) 540(M+1)

EXAMPLE 88

1-(1-{4-[(3,5-Dimethylpiperidin-1-yl)carbonyl]-2-nitrophenyl}piperidin-4-yl)-1,4-dihydro-2H-3,1-benzoxazin-2-one

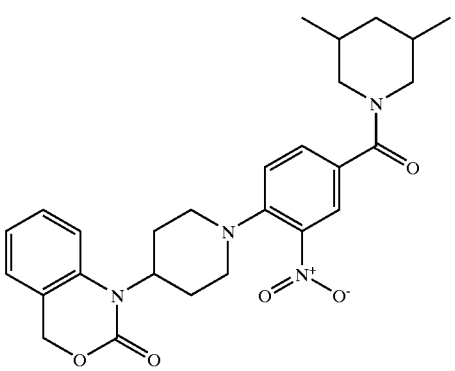

MS: APCI(+ve) 493(M+1)

EXAMPLE 89

1-[1-(4-{[(2R,6S)-2,6-Dimethylmorpholin4-yl]carbonyl}-2-nitrophenyl)piperidin-4-yl]-1,4-dihydro-2H-3,1-benzoxazin-2-one

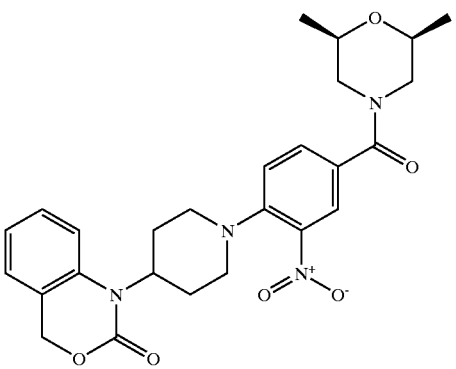

MS: APCI(+ve) 495(M+1)

EXAMPLE 90
1-{1-[4-({4-[2-(Methyloxy)phenyl]piperazin-1-yl}carbonyl)-2-nitrophenyl]piperidin-4-yl}-1,4-dihydro-2H-3,1-benzoxazin-2-one
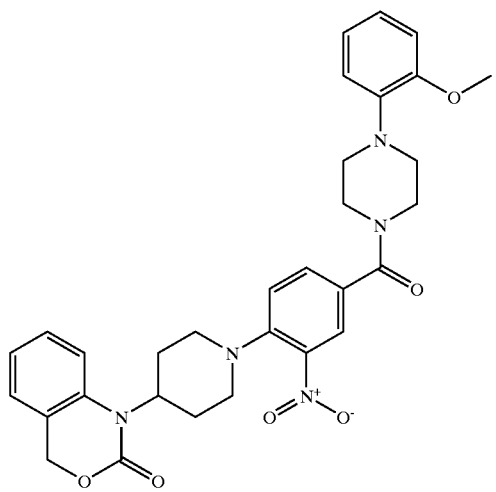
MS: APCI(+ve) 572(M+1)
EXAMPLE 91
1-{1-[2-Nitro-4-(thiomorpholin4-ylcarbonyl)phenyl]piperidin-4-yl}-1,4-dihydro-2H-3,1-benzoxazin-2-one
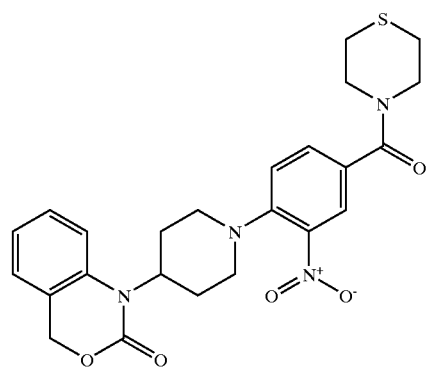
MS: APCI(+ve) 483(M+1)
EXAMPLE 92
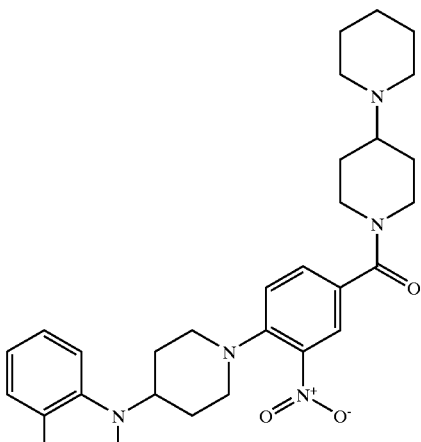
MS: APCI(+ve) 548(M+1)
EXAMPLE 93
1-(1-{4-[(4-{2-[(2-Hydroxyethyl)oxy]ethyl}piperazin-1-yl)carbonyl]-2-nitrophenyl}piperidin-4-yl)-1,4-dihydro-2H-3,1-benzoxazin-2-one
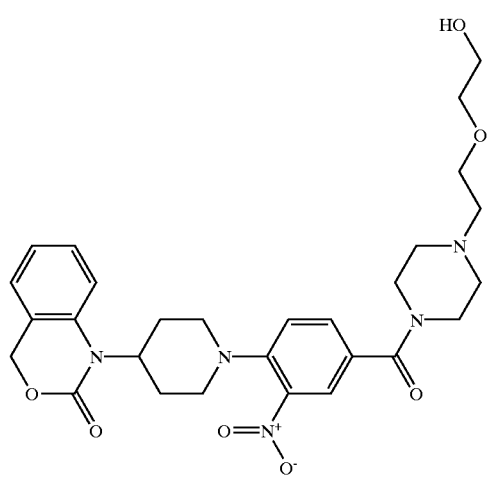
MS: APCI(+ve) 554(M+1)

EXAMPLE 94

N-Ethyl-3-nitro-4-[4-(2-oxo-2H-3,1-benzoxazin-1(4H)-yl)piperidin-1-yl]-N-(pyridin-4-ylmethyl)benzamide

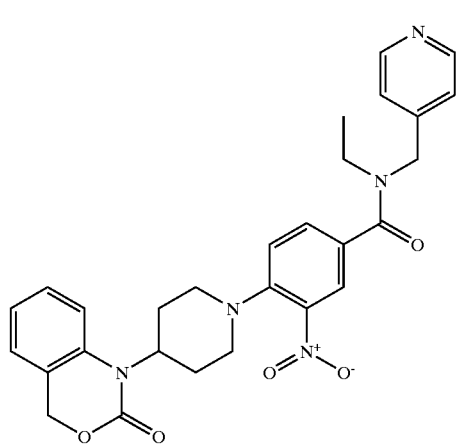

MS: APCI(+ve) 516(M+1)

EXAMPLE 95

N-Methyl-3-nitro-4-[4-(2-oxo-2H-3,1-benzoxazin-1(4H)-yl)piperidin-1-yl]-N-prop-2-ynylbenzamide

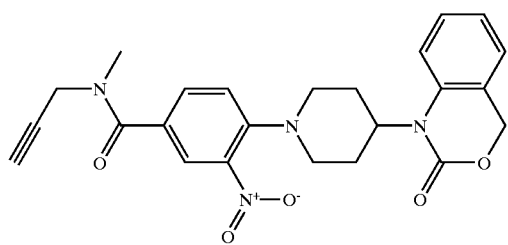

MS: APCI(+ve) 449(M+1)

EXAMPLE 96

1-(1-{4-[(4-Acetylpiperazin-1-yl)carbonyl]-2-nitrophenyl}piperidin-4-yl)-1,4-dihydro-2H-3,1-benzoxazin-2-one

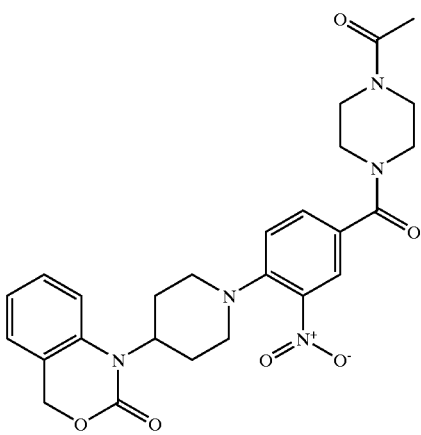

MS: APCI(+ve) 508(M+1)

EXAMPLE 97

1-[1-(4-{[2-(Hydroxymethyl)piperidin-1-yl]carbonyl}-2-nitrophenyl)piperidin-4-yl]-1,4-dihydro-2H-3,1-benzoxazin-2-one

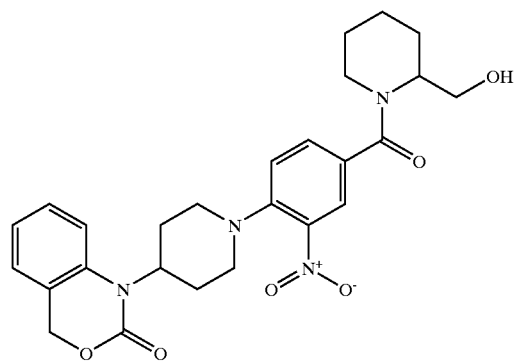

MS: APCI(+ve) 495(M+1)

EXAMPLE 98

4-({3-Nitro-4-[4-(2-oxo-2H-3,1-benzoxazin-1(4H)-yl)piperidin-1-yl]phenyl}carbonyl)piperazine-1-carbaldehyde

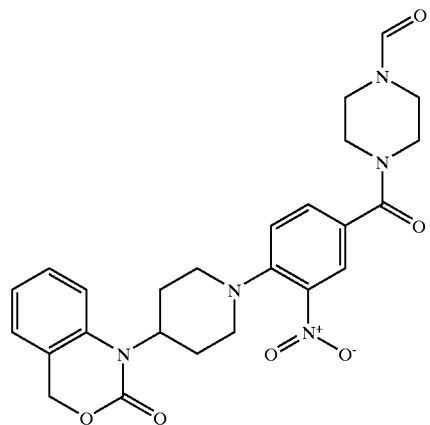

MS: APCI(+ve) 494(M+1)

EXAMPLE 99

N-Methyl-3-nitro-4-[4-(2-oxo-2H-3,1-benzoxazin-1(4H)-yl)piperidin-1-yl]-N-(phenylmethyl)benzamide

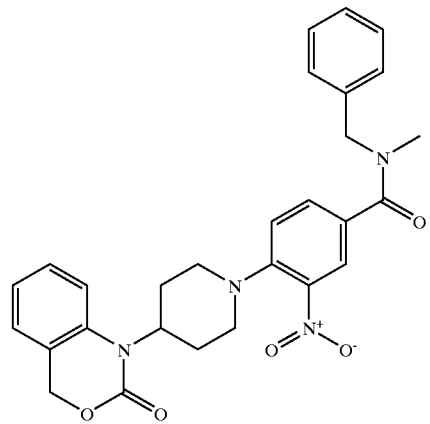

MS: APCI(+ve) 501(M+1)

EXAMPLE 100

Ethyl 4-({3-nitro-4-[4-(2-oxo-2H-3,1-benzoxazin-1(4H)-yl)piperidin-1-yl]phenyl}carbonyl)piperazine-1-carboxylate

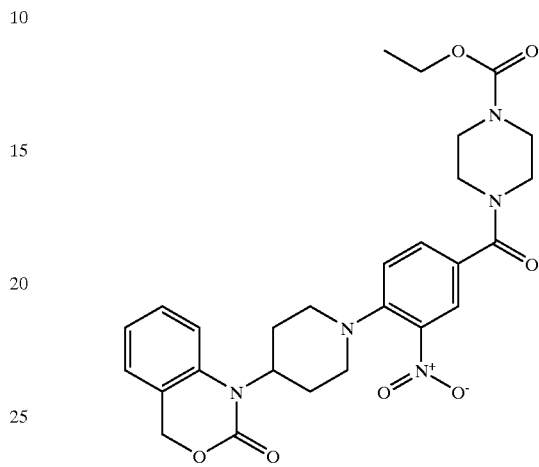

MS: APCI(+ve) 538(M+1)

EXAMPLE 101

Ethyl 1-({3-nitro-4-[4-(2-oxo-2H-3,1-benzoxazin-1(4H)-yl)piperidin-1-yl]phenyl}carbonyl)piperidine-4-carboxylate

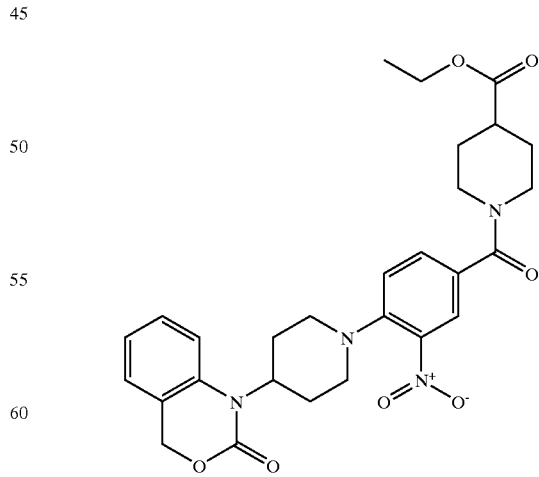

MS: APCI(+ve) 537(M+1)

EXAMPLE 102

1-({3-Nitro-4-[4-(2-oxo-2H-3,1-benzoxazin-1(4H)-yl)piperidin-1-yl]phenyl}carbonyl)piperidine-3-carboxamide

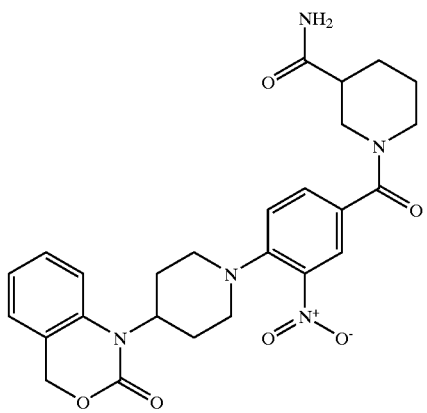

MS: APCI(+ve) 508(M+1)

EXAMPLE 103

1-(1-{4-[(4-Methylpiperazin-1-yl)carbonyl]-2-nitrophenyl}piperidin-4-yl)-1,4-dihydro-2H-3,1-benzoxazin-2-one

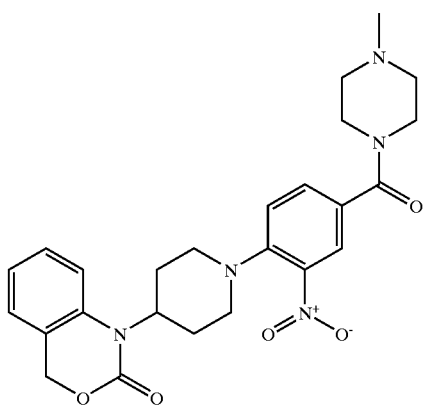

MS: APCI(+ve) 480(M+1)

EXAMPLE 104

1-{1-[4-(2,5-Dihydro-1H-pyrrol-1-ylcarbonyl)-2-nitrophenyl]piperidin-4-yl}-1,4-dihydro-2H-3,1-benzoxazin-2-one

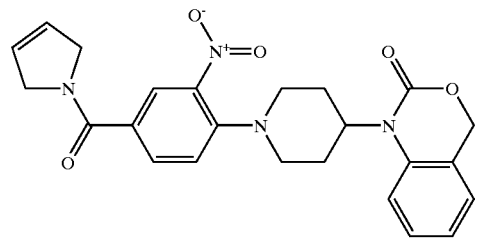

MS: APCI(+ve) 449(M+1)

EXAMPLE 105

N-Ethyl-N-(2-methylprop-2-enyl)-3-nitro-4-[4-(2-oxo-2H-3,1-benzoxazin-1(4H)-yl)piperidin-1-yl]benzamide

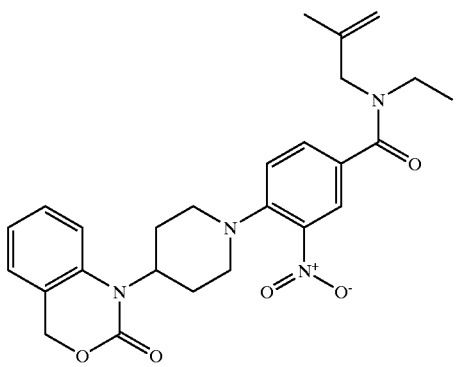

MS: APCI(+ve) 479(M+1)

EXAMPLE 106

N,N-Bis(cyanomethyl)-3-nitro-4-[4-(2-oxo-2H-3,1-benzoxazin-1(4H)-yl)piperidin-1-yl]benzamide

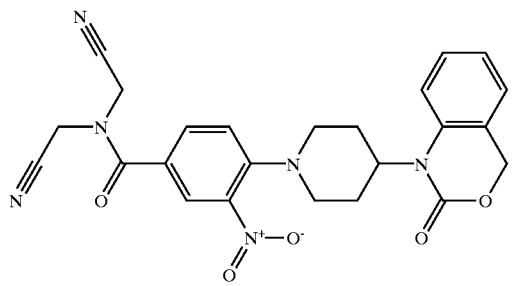

MS: APCI(+ve) 475(M+1)

EXAMPLE 107

N-Butyl-N-(cyanomethyl)-3-nitro-4-[4-(2-oxo-2H-3,1-benzoxazin-1(4H)-yl)piperidin-1-yl]benzamide

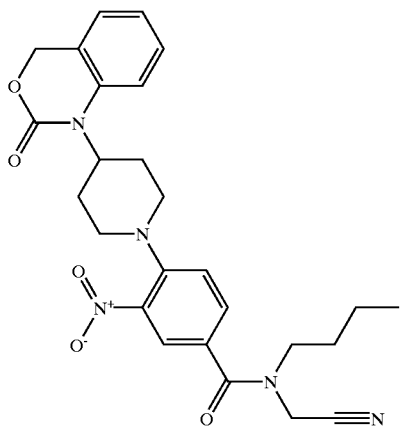

MS: APCI(+ve) 492(M+1)

EXAMPLE 108

N,N-Bis(2-hydroxypropyl)-3-nitro-4-[4-(2-oxo-2H-3,1-benzoxazin-1(4H)-yl)piperidin-1-yl]benzamide

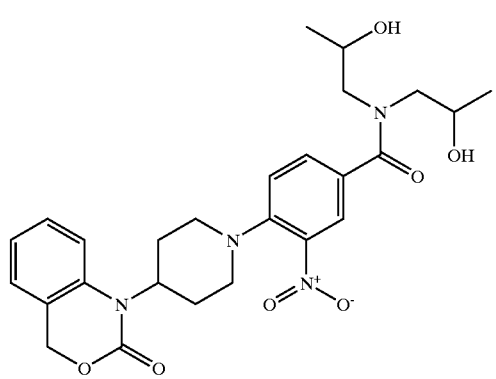

MS: APCI(+ve) 513(M+1)

EXAMPLE 109

1-(1-{4-[(4-Hydroxypiperidin-1-yl)carbonyl]-2-nitrophenyl}piperidin-4yl)-1,4-dihydro-2H-3,1-benzoxazin-2-one

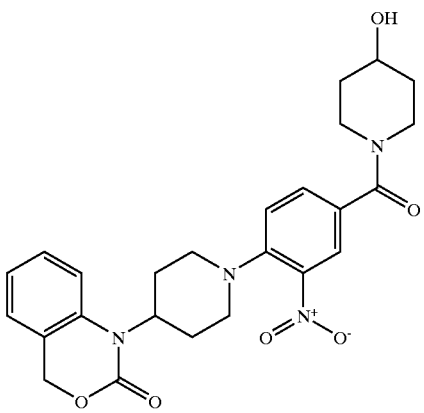

MS: APCI(+ve) 481(M+1)

EXAMPLE 110

1-(1-{4-[(2,5-Dimethyl-2,5-dihydro-1H-pyrrol-1-yl)carbonyl]-2-nitrophenyl}piperidin-4-yl)-1,4-dihydro-2H-3,1-benzoxazin-2-one

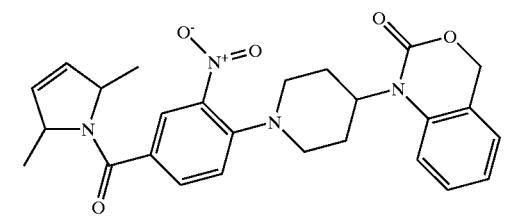

MS: APCI(+ve) 477(M+1)

EXAMPLE 111

N-Methyl-3-nitro-4-[4-(2-oxo-2H-3,1-benzoxazin-1(4H)-yl)piperidin-1-yl]-N-propylbenzamide

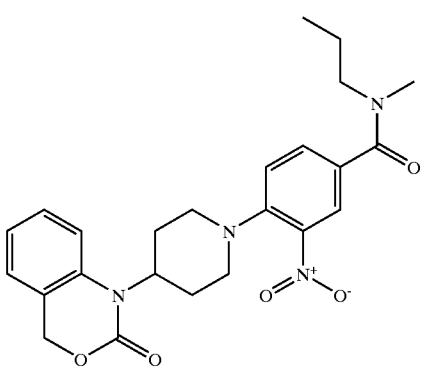

MS: APCI(+ve) 453(M+1)

EXAMPLE 112

N-(2-Amino-2-oxoethyl)-N-methyl-3-nitro-4-[4-(2-oxo-2H-3,1-benzoxazin-1(4H)-yl)piperidin-1-yl]benzamide

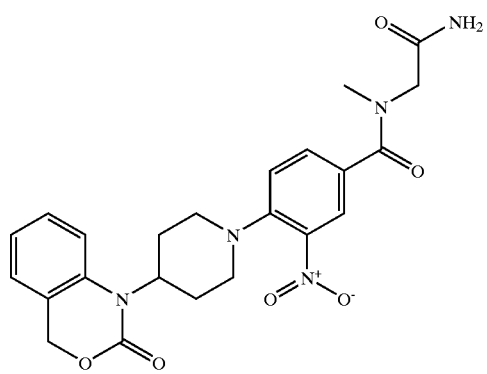

MS: APCI(+ve) 468(M+1)

EXAMPLE 113

N,N-Diethyl-1-({3-nitro-4-[4-(2-oxo-2H-3,1-benzoxazin-1(4H)-yl)piperidin-1-yl]phenyl}carbonyl)piperidine-3-carboxamide

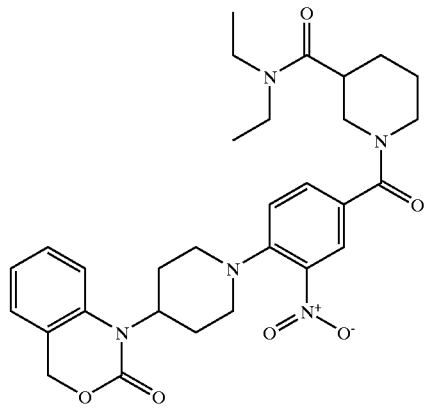

MS: APCI(+ve) 564(M+1)

EXAMPLE 114

N-Cyclohexyl-N-methyl-3-nitro-4-[4-(2-oxo-2H-3,1-benzoxazin-1(4H)-yl)piperidin-1-yl]benzamide

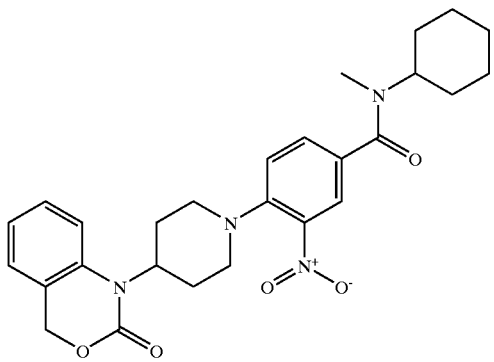

MS: APCI(+ve) 493(M+1)

EXAMPLE 115

N-(1-Methylethyl)-6-[4-(2-oxo-2H-3,1-benzoxazin-1(4H)-yl)piperidin-1-yl]pyridazine-3-carboxamide

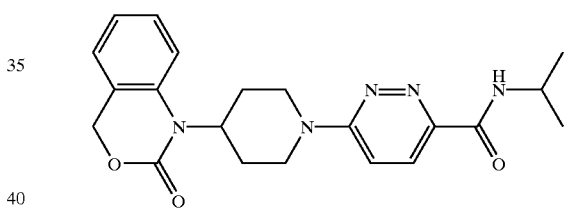

(i) 6-Chloro-N-(1-methylethyl)pyridazine-3caroxamide

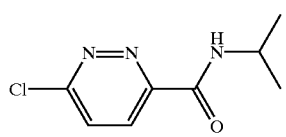

A solution of 6-chloro-3-pyridazinecarboxylic acid (0.25 g) and carbonyldiimidazole (0.282 g) in N,N-dimethylformamide (10 ml) was stirred at room temperature for 1 h. Isopropylamine (0.162 ml) was added, the mixture stirred for 3 h then partitioned between ethyl acetate and water. The organic layer was washed with water, dried, and evaporated under reduced pressure. Yield 0.284 g.

1H NMR: δ (DMSO-d6) 9.02(1H, d), 8.22(1H, d), 8.09 (1H, d), 4.22–4.13(1H, m), 1.21(6H, d)

(ii) N-(1-Methylethyl)-6-[4-(2-oxo-2H-3,1-benzoxazin-1(4H)-yl)piperidin-1-yl]pyridazine-3-carboxamide 1-Piperidin-4-yl-1,4-dihydro-2H-3,1-benzoxazin-2-one hydrochloride (0.38 g), the product from step (i) (0.28 g) and N,N-diisopropylethylamine (0.73 ml) in I-methyl-2-pyrrolidinone (6 ml) was heated at 100° C. for 8 h. The mixture was partitioned between ethyl acetate and water, the organic layer washed with water, dried, and evaporated under reduced pressure. Purification was by chromatography eluting with 80% ethyl acetate/isohexane to yield 0.225 g of a solid.

MS: APCI(+ve) 396(M+1)

1H NMR: δ (DMSO-d6) 8.51(1H, d), 7.84(1H, d), 7.45–7.35(3H, m), 7.30(1H, d), 7.13(1H, t), 5.14(2H, s), 4.64(2H, br d), 4.31–4.26(1H, m), 4.18–4.09(1H, m), 3.20 (2H, t), 2.50–2.44(2H, m), 1.91(2H, br d), 1.19(6H, d)

MP: 120° C.

EXAMPLE 116

N-[2-(Methyloxy)ethyl]-3-nitro-4-[4-(2-oxo-2H-3,1-benzoxazin-1(4H)-yl)piperidin-1-yl]benzamide

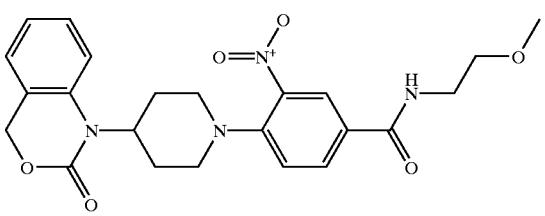

The title compound was prepared from the product of example 8 step (i) and 2-methoxyethylamine (0.5 ml) using the method of example 115 step (i). Yield 0.065 g.

MS: APCI(+ve) 455(M+1)

1H NMR: δ (CDCl₃) 8.22(1H, dd), 7.92(1H, dd), 7.37 (1H, t), 7.20–7.09(4H, m), 6.46(1H,br s), 5.10(2H, s), 4.25–4.17(1H, m), 3.68–3.47(6H, m), 3.40(3H, s), 3.15(2H, t), 2.93–2.79(2H, m), 1.95(2H, d)

MP: 192–3° C.

EXAMPLE 117

N-(1-Methylethyl)-6-[4-(2-oxo-2H-3,1-benzoxazin-1 (4H)-yl)piperidin-1-yl]pyridine-3-carboxamide

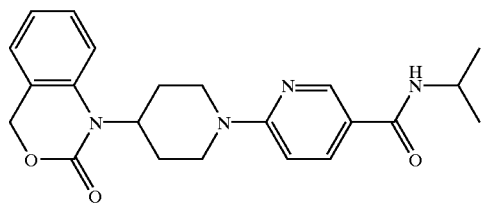

(i) 6-Chloro-N-(1-methylethyl)pyridine-3-carboxamide

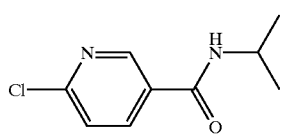

The product was prepared from 6-chloro-nicotinic acid (1.0 g), carbonyldiimidazole (0.8 g) and isopropylamine (0.6 ml) using the method of example 115 step (i). Yield 0.75 g.

MS: APCI(+ve) 199(M+1)

(ii) N-(1-Methylethyl)-6-[4-(2-oxo-2H-3,1-benzoxazin-1 (4H)-yl)piperidin-1-yl]pyridine-3-carboxamide The title compound was prepared from the product of step (i) (0.4 g) and 1-piperidin-4-yl-1,4-dihydro-2H-3,1-benzoxazin-2-one hydrochloride (0.5 g) using the method of example 115 step (ii). Yield 0.22 g.

1H NMR: δ (DMSO-d6) 8.59(1H, d), 7.97–7.94(2H, m), 7.41–7.28(3H, m), 7.12(1H, t), 6.90(1H, d), 5.13(2H, s), 4.56(2H, br d), 4.25–4.18(1H, m), 4.12–4.00(1H, m), 3.06 (2H, t), 2.50–2.38(2H, m), 1.85(2H, br d), 1.15(6H, d)

MP: >230° C.

EXAMPLE 118

5-Chloro-N-(1-methylethyl)-6-[4-(2-oxo-2H-3,1-benzoxazin-1(4H)-yl)piperidin-1-yl]pyridine-3-carboxamide

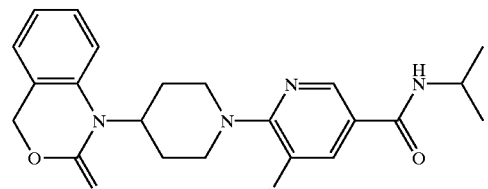

(i) 5,6-Dichloro-N-(1-methylethyl)pyridine-3-carboxamide

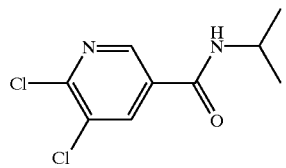

The product was prepared from 5,6-dichloro-nicotinic acid (0.86 g), carbonyldiimidazole (0.8 g) and isopropylamine (0.52 ml) using the method of example 115 step (i). Yield 0.69 g.

MS: APCI(+ve) 199(M+1)

(ii) 5-Chloro-N-(1-methylethyl)-6-[4-(2-oxo-2H-3,1-benzoxazin-1(4H)-yl)piperidin-1-yl]pyridine-3-carboxamide The title compound was prepared from the product of step (i) (0.3 g) and 1-piperidin-4-yl-1,4-dihydro-2H-3,1-benzoxazin-2-one hydrochloride (0.35 g) using the method of example 115 step (ii). Yield 0.187 g.

MS: APCI(+ve) 429(M+1)

1H NMR: δ (DMSO-d6) 8.64(1H, d), 8.25(1H, d), 8.18 (1H, d), 7.40(1H, t), 7.33–7.30(2H, m), 7.12(1H, t), 5.15 (2H, s), 4.18–4.02(4H, m), 3.06(2H, t), 2.71–2.60(2H, br d), 1.16(6H, d)

MP: 216° C.

EXAMPLE 119

N-(1-Methylethyl)-3-nitro-4-[4-(2-oxo-2H-3,1-benzoxazin-1(4H)-yl)piperidin-1-yl] benzenesulfonamide

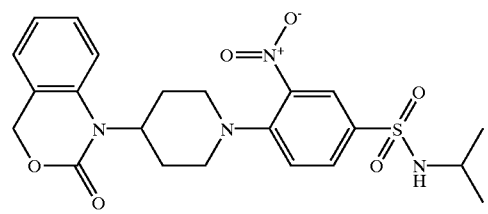

(i) 4-Chloro-N-(1-methylethyl)-3-nitrobenzenesulfonamide

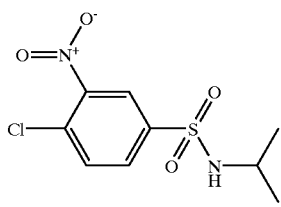

4-Chloro-3-nitrobenzenesulfonyl chloride (2 g) and isopropylamine (2.1 ml) in dichloromethane (30 ml) was stirred at room temperature for 2 h. The mixture was washed with water, 2M hydrochloric acid, water, dried and evaporated under reduced pressure. Yield 2.2 g.

1H NMR: δ (DMSO-d6) 8.45(1H, d), 8.09–7.98(3H, m), 3.39–3.31(1H, septet), 0.99(6H, d)

(ii) N-(1-Methylethyl)-3-nitro-4-[4-(2-oxo-2H-3,1-benzoxazin-1(4H)-yl)piperidin-1-yl]benzenesulfonamide The title compound was prepared from the product of step (i) (0.14 g) and 1-piperidin-4-yl-1,4-dihydro-2H-3,1-benzoxazin-2-one hydrochloride (0.1 g) using the method of example 115 step (ii). Yield 0.037 g.

MS: APCI(+ve) 475(M+1)

1H NMR: δ (DMSO-d6) 8.17(1H, d), 7.86(1H, dd), 7.63(1H, d), 7.48(1H, d), 7.40(1H, t), 7.34–7.30(2H, m), 7.13(1H, t), 5.15(2H, s), 4.19–4.13(1H, m), 3.46(2H, d), 3.32–3.20(3H, m), 2.67–2.59(2H, m), 1.88(2H, d), 0.98(6H, d)

MP: 168° C.

EXAMPLE 120

1-[1-(4-Amino-2-chlorophenyl)piperidin-4-yl]-1,4-dihydro-2H-3,1-benzoxazin-2-one

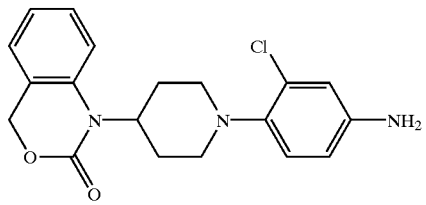

(i) 1-[1-(2-Chloro-4-nitrophenyl)piperidin-4-yl]-1,4-dihydro-2H-3,1-benzoxazin-2-one

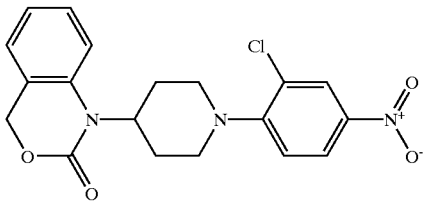

The product was prepared from 1-piperidin-4yl-1,4-dihydro-2H-3,1-benzoxazin-2-one hydrochloride (1.5 g) and 3-chloro-4-fluoronitrobenzene (1.23 g) using the method of example 115 step (ii). Yield 1.37 g.

MS: APCI(+ve) 388(M+1)

(ii) 1-[1-(4-Amino-2-chlorophenyl)piperidin-4-yl]-1,4-dihydro-2H-3,1-benzoxazin-2-one Iron powder (1.5 g) was added to a solution of the product from step (i) (1.37 g) in acetic acid (50 ml) and tetrahydrofuran (20 ml). After stirring at room temperature for 5 h, the mixture was filtered through celite, the solvent removed under reduced pressure and the residue partitioned between ethyl acetate and aqueous sodium hydrogencarbonate solution. The organic layer was washed with water, dried and evaporated under reduced pressure. Purification was by chromatography eluting with 50% ethyl acetate/isohexane. Yield 1.05 g.

MS: APCI(+ve) 358(M+1)

1H NMR: δ (DMSO-d6) 7.40(1H, t), 7.29(2H, m), 7.12(1H, t), 6.92(1H, d), 6.64(1H, d), 6.49(1H, dd), 5.14(2H, s), 5.03(2H, s), 3.98–3.92(1H, m), 3.14(2H, d), 2.7–2.62(4H, m), 1.83(2H, br d)

MP: 158° C.

EXAMPLE 121

3-Cyano-N-(1-methylethyl)-4-[4-(2-oxo-2H-3,1-benzoxazin-1(4H)-yl)piperidin-1-yl]benzamide

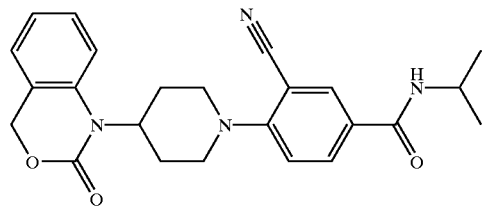

(i) Methyl 4-chloro-3-cyanobenzoate

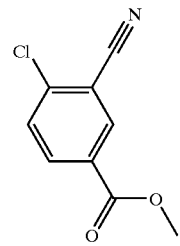

A solution of sodium nitrite (1.28 g) in water (8 ml) was added over 10 min to a mixture of methyl 3-amino-4-chlorobenzoate (4.0 g) in water (40 ml) and concentrated hydrochloric acid (5 ml) at 0° C. After 30 min the mixture was neutralised with aqueous sodium hydroxide solution to pH~7 then added portionwise to a solution of copper cyanide (prepared from sodium cyanide (2.87 g) and copper(I) chloride (2.23 g) in water (40 ml)) at 0° C. The mixture was stirred at room temperature for 2 h then partitioned between ethyl acetate and water. The organics were washed with water, dried and evaporated under reduced pressure. The residue was triturated with 20% ethyl acetate/isohexane to yield a solid (1.55 g).

1H NMR: δ (CDCl₃) 8.34(1H, d), 8.21–8.17(1H, m), 7.62(1H, dd), 3.96(3H, s)

(ii) 4-Chloro-3-cyanobenzoic acid

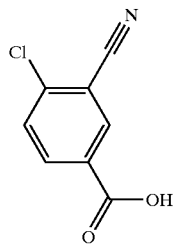

A solution of the product from step (i) (1.5 g) and lithium hydroxide hydrate (0.84 g) in a mixture of (1:1)water and tetrahydrofuran (40 ml) was stirred at room temperature for 2 h. The tetrahydrofuran was removed under reduced pressure and the residue partitioned between diethyl ether and water. The aqueous layer was acidified with 2M hydrochloric acid then extracted with ethyl acetate. The organic layer was dried and evaporated under reduced pressure. Yield 1.3 g.

1H NMR: δ (CDCl$_3$) 8.42(1H, d), 8.28–8.24(1H, m), 7.67(1H, dd)

(iii) 4-Chloro-3-cyano-N-(1-methylethyl)benzamide

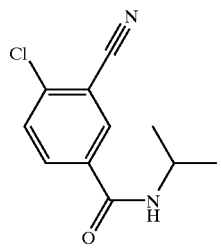

The above compound was prepared from the product of step (ii) (0.6 g), carbonyldiimidazole (0.59 g) and isopropylamine (0.51 ml) using the method of example 115 step (i). Yield 0.68 g.

1H NMR: δ (CDCl$_3$) 8.06(1H, d), 7.96–7.92(1H, m), 7.59(1H, d), 5.96(1H, br s), 4.28(1H, septet), 1.29(6H, d)

(iv) 3-Cyano-N-(1-methylethyl)-4-[4-(2-oxo-2H-3,1-benzoxazin-1(4H)-yl)piperidin-1-yl]benzamide The title compound was prepared from the product of step (iii) (0.29 g) and 1-piperidin-4-yl-1,4-dihydro-2H-3,1-benzoxazin-2-one hydrochloride (0.3 g) using the method of example 115 step (ii). Yield 0.073 g.

MS: APCI(+ve) 419(M+1)

1H NMR: δ (DMSO-d6) 8.21(1H, d), 8.18(1H, d), 8.03 (1H, dd), 7.40(1H, t), 7.34–7.30(2H, m), 7.22(1H, d), 7.13 (1H, t), 5.16(2H, s), 4.16–4.04(2H, m), 3.81(2H, br d), 3.14(2H, t), 2.75–2.65(2H, m), 1.93(2H, br d), 1.16(6H, d)

MP: 200° C.

EXAMPLE 122

N-{3-Chloro-4-[4-(2-oxo-2H-3,1-benzoxazin-1(4H)-yl)piperidin-1-yl]phenyl}-2-methylpropanamide

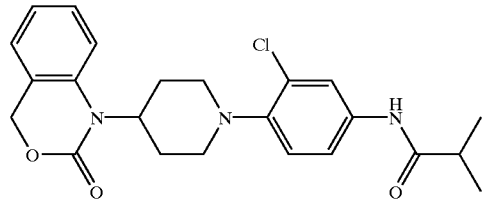

Isobutyryl chloride (0.017 ml) was added to a stirred solution of the product from example 120 step (ii) (0.05 g) and triethylamine (0.07 ml) in dichloromethane (1 ml) at room temperature. After 2 h the mixture was partitioned between ethyl acetate and water, the organics separated, washed with water, dried, and evaporated under reduced pressure. Trituration with ether gave a solid, yield 0.048 g.

MS: APCI(+ve) 428(M+1)

1H NMR: δ (DMSO-d6) 9.86(1H, s), 7.79(1H, d), 7.46 (1H, dd), 7.42–7.38(1H, m), 7.31–7.29(2H, m), 7.14–7.10 (2H, m), 5.15(2H, s), 4.04–3.98(1H, m), 3.33–2.84(2H, m), 2.82(2H, t), 2.75–2.65(2H, m), 2.59–2.50(1H, m), 1.87(2H, br d), 1.09(6H, d)

MP: 228° C.

EXAMPLE 123

N-{3-Chloro-4-[4-(2-oxo-2H-3,1-benzoxazin-1(4H)-yl)piperidin-1-yl]phenyl}propane-2-sulfonamide

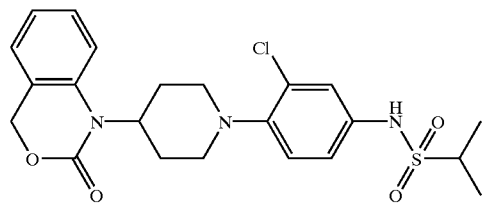

Isopropylsulphonyl chloride (0.03 ml) was added to a stirred solution of the product from example 120 step (ii) (0.05 g), pyridine (0.1 ml) in acetonitrile (0.9 ml) at room temperature. The mixture was stirred overnight, partitioned between ethyl acetate and water, the organics separated, washed with water, dried, and evaporated under reduced pressure. Purification was by chromatography eluting with 40% ethyl acetate/isohexane. Yield 0.015 g.

MS: APCI(+ve) 464(M+1)

1H NMR: δ (DMSO-d6) 9.76(1H, s), 7.40(1H, t), 7.31–7.27(3H, m), 7.19–7.10(3H, m), 5.15(2H, s), 4.04–3.98(1H, m), 3.30(2H, br d), 3.25–3.18(1H, m), 2.82 (2H, t), 2.74–2.65(2H, m), 1.87(2H, br d), 1.24(6H, d)

MP: 175° C.

EXAMPLE 124

N-{3-Chloro-4-[4-(2-oxo-2H-3,1-benzoxazin-1(4H)-yl)piperidin-1-yl]phenyl}-1-cyanocyclopropanecarboxamide

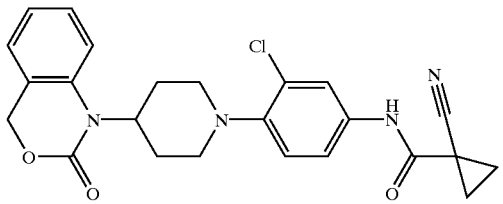

The title compound was prepared from the product of example 120 step (ii) (0.05 g), carbonyldiimidazole (0.025 g) and 1-cyano-1-cyclopropane carboxylic acid (0.019 g) using the method of example 115 step (i). Yield 0.003 g.

MS: APCI(+ve) 451 (M+1)

1H NMR: δ (DMSO-d6) 10.02(1H, s), 7.70(1H, d), 7.52–7.48(1H, m), 7.40(1H, t), 7.30(2H, t), 7.17–7.10(2H, m), 5.15(2H, s), 4.05–3.99(1H, m), 3.32(2H, d), 2.83(2H, t), 2.74–2.67(2H, m), 1.88(2H, d), 1.67(4H, s)

EXAMPLE 125

(2S)-N-{3-Chloro-4-[4-(2-oxo-2H-3,1-benzoxazin-1(4H)-yl)piperidin-1-yl]phenyl}-1-methylpyrrolidine-2-carboxamide

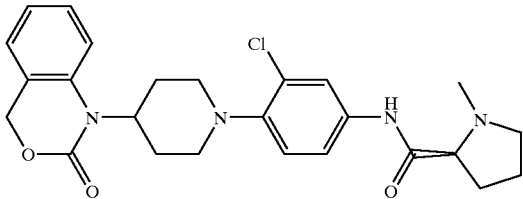

A mixture of the product from example 120 step (ii) (0.1 g), N-methyl-L-proline (0.044 g), N,N-diisopropylethylamine (0.17 ml), 1-hydroxybenzotriazole (0.043 g), 2-(1H-benzotriazole-1-yl)-1,1,3,3-tetramethyluronium tetrafluoroborate (0.103 g) in N,N-dimethylformamide (3 ml) were stirred at room temperature overnight then partitioned between ethyl acetate and water. The organic layer was washed with water, dried and evaporated under reduced pressure. Purification was by chromatography eluting with 4% methanol/dichloromethane. Yield 0.038 g.

MS: APCI(+ve) 469(M+1)

1H NMR: δ (DMSO-d6) 9.73(1H, s), 7.88(1H, d), 7.59 (1H, dd), 7.38(1H, t), 7.30(2H, d), 7.14–7.10(2H, m), 5.15 (2H, s), 4.04–3.98(1H, m), 3.30(2H, d), 3.12–3.08(1H, m), 2.90–2.67(5H, m), 2.35–2.29(1H, m), 2.33(3H, s), 2.18–2.09(1H, m) 1.87(2H, br d), 1.82–1.75(3H, m)

MP: 155° C.

EXAMPLE 126

5-Chloro-N-(1-methylethyl)-6-[4-(4-methyl-2-oxo-2H-3,1-benzoxazin-1(4H)-yl)piperidin-1-yl]pyridine-3-carboxamide

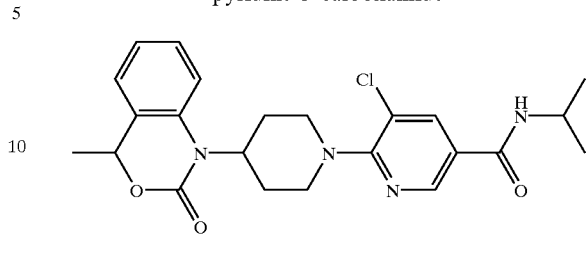

(i) 1,1-Dimethylethyl 4-(4-methyl-2-oxo-2H-3,1-benzoxazin-1(4H)-yi)piperidine-1-carboxylate

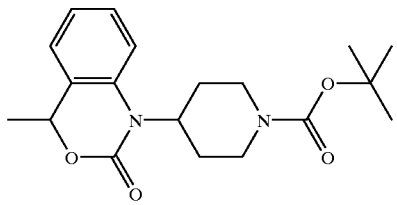

Acetic acid (1 ml) was added dropwise to a solution of N-tert-butoxycarbonyl-4-piperidone (9.4 g), 1-(2-aminophenyl)-ethanol (4.3 g) and sodium cyanoborohydride (10 g) in dichloromethane and the mixture stirred at room temperature overnight. The mixture was partitioned between ethyl acetate and water, the organics separated and washed with aqueous sodium hydrogencarbonate solution, water, dried, and evaporated under reduced pressure. The crude product was dissolved in tetrahydrofuran (100 ml) and N,N-diisopropylethylamine (23 ml), cooled to 0° C., then triphosgene (4.3 g) added. The mixture was warmed to room temperature and stirred overnight. The mixture was partitioned between ethyl acetate and water, the organics washed with water, dried and evaporated under reduced pressure. Purification was by chromatography eluting with 20% ethyl acetate/isohexane. Yield 1.4 g.

MS: APCI(+ve) 247(M+1-Boc)

(ii) 4-Methyl-1-piperidin-4-yl-1,4-dihydro-2H-3,1-benzoxazin-2-one hydrochloride

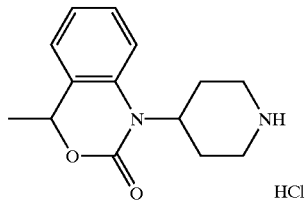

4M Hydrogen chloride in 1,4-dioxane (20 ml) was added to a solution of the product from step (i) (1.4 g) in 1,4-dioxane (20 ml) and the mixture stirred at room temperature overnight. The solvent was removed under reduced pressure and the residue triturated with ether. Yield 1.0 g.

MS: APCI(+ve) 247(M+1)

(iii) 5-Chloro-N-(1-methylethyl)-6-[4-(4-methyl-2-oxo-2H-3,1-benzoxazin-1(4H)-yl)piperidin-1-yl]pyridine-3-carboxamide The title compound was prepared from the product of step (ii) (0.36 g) and the product from example 117 step (i) (0.466 g) using the method of example 115 step (ii). Yield 0.112 g MS: APCI(+ve) 443(M+1)

1H NMR: δ (DMSO-d6) 8.64(1H, d), 8.25(1H, d), 8.18 (1H, d), 7.42–7.38(1H, m), 7.34–7.27(2H, m), 7.16–7.12 (1H, m), 5.36(1H, q), 4.18–4.05(4H, m), 3.09–3.02(2H, m), 2.72–2.61(2H, m), 1.89(2H, br d), 1.57(3H,d), 1.16(6H, d)

EXAMPLES 127

±-5-Chloro-N-(1-methylethyl)-6-[(cis)-3-methyl-4-(2-oxo-2H-3,1-benzoxazin-1(4H)-yl)piperidin-1-yl]pyridine-3-carboxamide hydrochloride

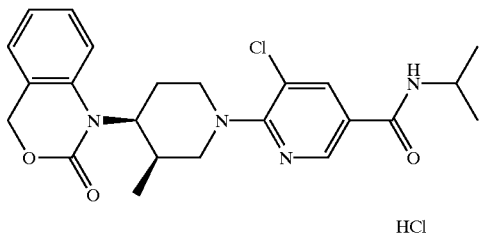

HCl

EXAMPLE 128

±-5-Chloro-N-(1-methylethyl)-6-[(trans)-3-methyl-4-(2-oxo-2H-3,1-benzoxazin-1(4H)-yl)piperidin-1-yl]pyridine-3-carboxamide hydrochloride

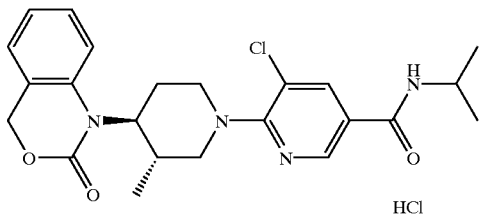

HCl (i) 1,1-Dimethylethyl 4-{[2-(hydroxymethyl)phenyl]amino}-3-methylpiperidine-1-carboxylate

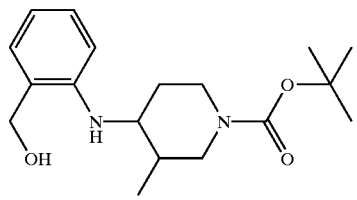

The product was prepared from N-tert-butoxycarbonyl-3-methyl-4-piperidone (4.3 g) and 2-amino-benzyl alcohol (2.59 g) using the method of example 7 step (i). Yield 6.3 g as a mixture of diastereoisomers.

MS: APCI(+ve) 320(M+1)

(ii) ±-1,1-Dimethylethyl (cis)-3-methyl-4-(2-oxo-2H-3,1-benzoxazin-1(4H)-yl)piperidine-1-carboxylate ±-1,1-Dimethylethyl (trans)-3-methyl-4-(2-oxo-2H-3,1-benzoxazin-1(4H)-yl)piperidine-1-carboxylate

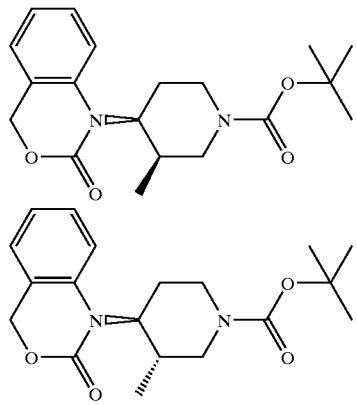

The above compounds were prepared from the product of step (i) (6.3 g) using the method of example 7 step (ii). Cis and trans diastereoisomers were separated (relative stereochemistry).

±-1,1-Dimethylethyl (cis)-3-methyl-4-(2-oxo-2H-3,1-benzoxazin-1(4H)-yl)piperidine-1-carboxylate, yield 0.24 g
MS: APCI(+ve) 247(M+1)

±-1,1-Dimethylethyl (trans)-3-methyl-4-(2-oxo-2H-3,1-benzoxazin-1(4H)-yl)piperidine-1-carboxylate, yield 0.68 g
MS: APCI(+ve) 247(M+1)

(iii) ±-5-Chloro-N-(1-methylethyl)-6-1(cis)-3-methyl-4-(2-oxo-2–3,1-benzoxazin-1(4H)-yl)piperidin-1-yl]pyridine-3-carboxaniide hydrochloride ±-1,1-Dimethylethyl (cis)-3-methyl-4-(2-oxo-2H-3,1-benzoxazin-1(4H)-yl)piperidine-1-carboxylate (0.24 g) was dissolved in 4M hydrogen chloride in 1,4-dioxane (5 ml) stirred at room temperature for 4 h, then evaporated under reduced pressure. The product was dissolved in 1-methyl 2-pyrrolidinone (10 ml), N,N-diisopropylethylamine (0.5 ml) and the product from example 117 step (i) (0.23 g) added. The mixture was heated at 100° C. for 12 h, partitioned between ethyl acetate and water, the organics separated, dried and evaporated under reduced pressure. Purification was by chromatography eluting with 30–40% ethyl acetate/isohexane. The hydrochloride salt was made from ethereal hydrogen chloride. Yield 0.07 g.

MS: APCI(+ve) 443(M+1)

1H NMR: δ (DMSO-d6) 8.64(1H, d), 8.27(1H, d), 8.19 (1H, d), 7.41–7.30(3H, m), 7.12(1H, t), 6.12(2H, br s), 5.22–5.14(2H, m), 4.12–3.99(3H, m), 3.77(1H, br s), 3.13 (1H, br t), 2.86(1H, br s), 2.75–2.50(2H, m), 1.94(1H, br d), 1.16(6H, d), 0.87(3H, d)

MP: 215° C.

±-5-chloro-N-(1-methylethyl)-6-[(trans)-3-methyl-4-(2-oxo-2H-3,1-benzoxazin-1(4H)-yl)piperidin-1-yl]pyridine-3-carboxamide hydrochloride The titled compound was prepared from ±-1,1-dimethylethyl (trans)-3-methyl-4-(2-oxo-2H-3,1-benzoxazin-1(4H)-yl)piperidine-1-carboxylate (0.68 g) using the same method as step (iii). Yield 0.219 g.

MS: APCI(+ve) 443(M+1)

1H NMR: δ (DMSO-d6) 8.63(1H, s), 8.25(1H, d), 8.17 (1H, s), 7.40–7.29(2H, m), 7.28(1H, d), 7.12(1H, t), 6.04 (2H, br s), 5.21–5.13(2H, m), 4.29–4.24(1H, m), 4.12–3.91 (3H, m), 3.30(1H, dd), 3.18–3.02(2H, m), 2.56–2.54(1H, m), 1.87(1H, br d), 1.16(6H, d), 1.09(3H, d)

MP: 195° C.

EXAMPLES 129–144

(i) 2-[4-(2-Oxo-2H-3,1-benzoxazin-1(4H)-yl)piperidin-1-yl]-4-(trifluoromethyl)pyrimidine-5-carboxylic acid

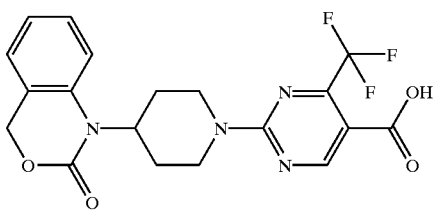

The title compound was prepared from 1-piperidin-4-yl-1,4-dihydro-2H-3,1-benzoxazin-2-one hydrochloride (0.70 g) and 2-chloro-4-(trifluoromethyl)pyrimidine-5-carboxylic acid (1.8 g) using the method of example 115 step (ii). Yield 1.1 g.

MS: APCI(+ve) 423(M+1)

(ii) Examples 129–144

Oxalyl chloride (0.1 ul) was added to a solution of the product from step (i) (0.27 g) in dichloromethane (10 ml) and stirred at room temperature for 3 h. The solvent was removed under reduced pressure and the residue dissolved in 1-methyl-2-pyrrolidinone. An aliquot of the solution of the acid chloride (0.1 ml), the appropriate amine (2 equivalents) and triethylamine (5 equivalents) in 1-methyl-2-pyrrolidinone (0.03 ml) were left at room temperature for 24 h. The reaction mixture was evaporated to dryness and the residue dissolved in dimethylsulphoxide (0.4 ml).

EXAMPLE 129

2-[4-(2-Oxo-2H-3,1-benzoxazin-1(4H)-yl)piperidin-1-yl]-N-(1,3,4-thiadiazol-2-yl)-4-(trifluoromethyl)pyrimidine-5-carboxamide

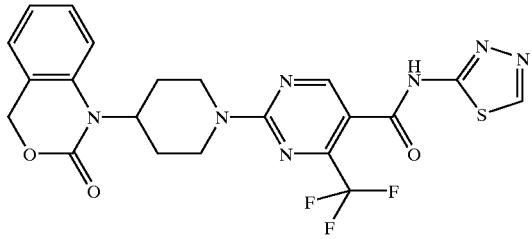

MS: APCI(+ve) 505(M+1)

EXAMPLE 130

2-[4-(2-Oxo-2H-3,1-benzoxazin-1(4H)-yl)piperidin-1-yl]-N-(1H-1,2,4-triazol-3-yl)-4-(trifluoromethyl)pyrimidine-5-carboxamide

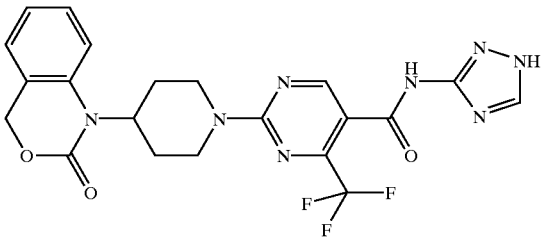

MS: APCI(+ve) 488(M+1)

EXAMPLE 131

2-[4-(2-Oxo-2H-3,1-benzoxazin-1(4H)-yl)piperidin-1-yl]-N-(1H-pyrazol-3-yl)-4-(trifluoromethyl)pyrimidine-5-carboxamide

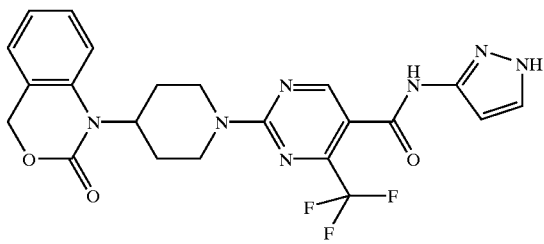

MS: APCI(+ve) 487(M+1)

EXAMPLE 132

N-(4-Hydroxycyclohexyl)-2-[4-(2-oxo-2H-3,1-benzoxazin-1(4H)-yl)piperidin-1-yl]-4-(trifluoromethyl)pyrimidine-5-carboxamide

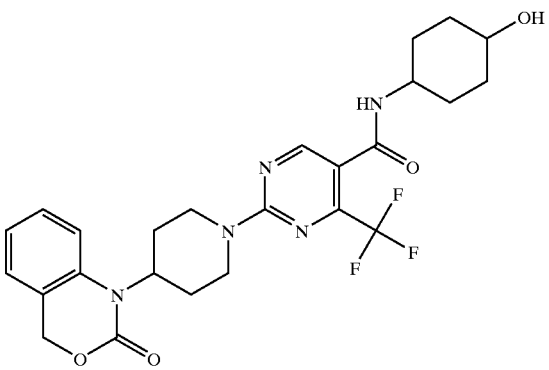

MS: APCI(+ve) 519(M+1)

EXAMPLE 133

N-[1-(Hydroxymethyl)propyl]-2-[4-(2-oxo-2H-3,1-benzoxazin-1(4H)-yl)piperidin-1-yl]-4-(trifluoromethyl)pyrimidine-5-carboxamide

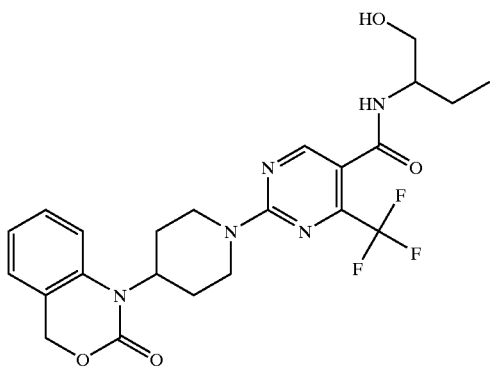

MS: APCI(+ve) 493(M+1)

EXAMPLE 134

N-(3-Hydroxy-2,2-dimethylpropyl)-2-[4-(2-oxo-2H-3,1-benzoxazin-1(4H)-yl)piperidin-1-yl]-4-(trifluoromethyl)pyrimidine-5-carboxamide

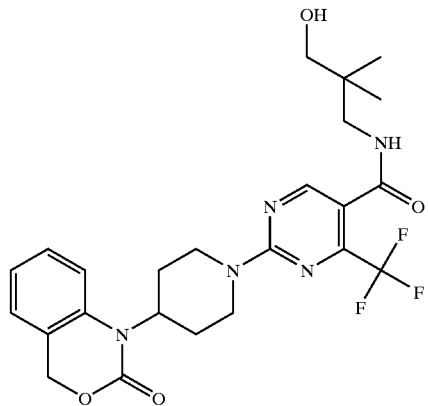

MS: APCI(+ve) 507 (M+1)

EXAMPLE 135

2-[4-(2-Oxo-2H-3,1-benzoxazin-1(4H)-yl)piperidin-1-yl]-N-(tetrahydrofuran-2-ylmethyl)-4-(trifluoromethyl)pyrimidine-5-carboxamide

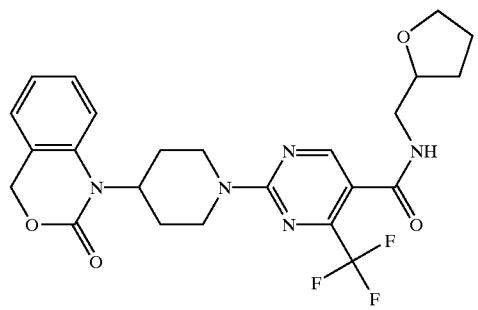

MS: APCI(+ve) 505(M+1)

EXAMPLE 136

N-Cyclobutyl-2-[4-(2-oxo-2H-3,1-benzoxazin-1(4H)-yl)piperidin-1-yl]-4-(trifluoromethyl)pyrimidine-5-carboxamide

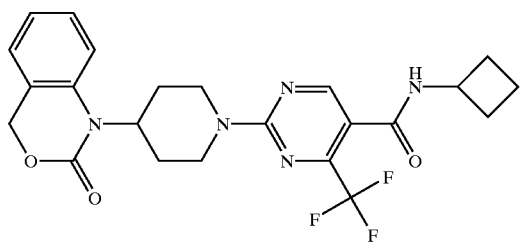

MS: APCI(+ve) 475(M+1)

EXAMPLE 137

N-Cyclopentyl-2-[4-(2-oxo-2H-3,1-benzoxazin-1(4H)-yl)piperidin-1-yl]-4-(trifluoromethyl)pyrimidine-5-carboxamide

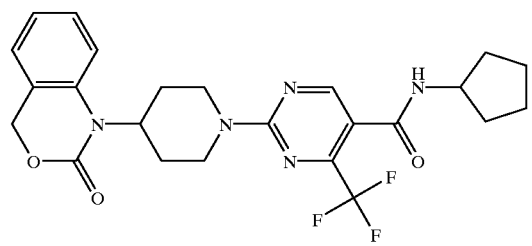

MS: APCI(+ve) 489(M+1)

EXAMPLE 138

N-[2-(1H-Imidazol-4-yl)ethyl]-2-[4-(2-oxo-2H-3,1-benzoxazin-1(4H)-yl)piperidin-1-yl]-4-(trifluoromethyl)pyrimidine-5-carboxamide

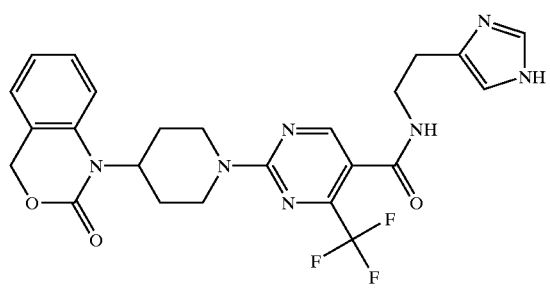

MS: APCI(+ve) 515(M+1)

EXAMPLE 139

N-(1-Ethynylcyclohexyl)-2-[4-(2-oxo-2H-3,1-benzoxazin-1(4H)-yl)piperidin-1-yl]-4-(trifluoromethyl)pyrimdine-5-carboxamide

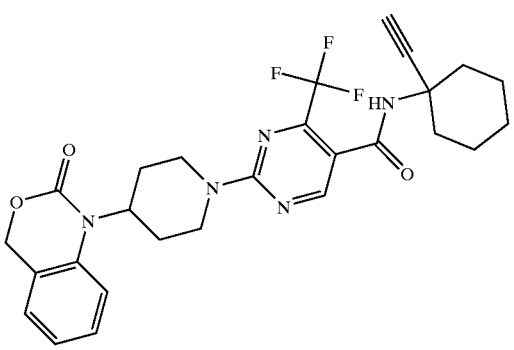

MS: APCI(+ve) 527(M+1)

EXAMPLE 140

N-[(1R)-1-(Hydroxymethyl)-2-methylpropyl]-2-[4-(2-oxo-2H-3,1-benzoxazin-1(4H)-yl)piperidin-1-yl]-4-(trifluoromethyl)pyrimidine-5-carboxamide

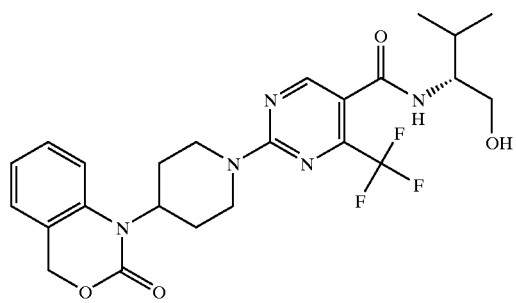

MS: APCI(+ve) 507(M+1)

EXAMPLE 141

N-(2-Hydroxy-1,1-dimethylethyl)-2-[4-(2-oxo-2H-3,1-benzoxazin-1(4H)-yl)piperidin-1-yl]-4-(trifluoromethyl)pyrimidine-5-carboxamide

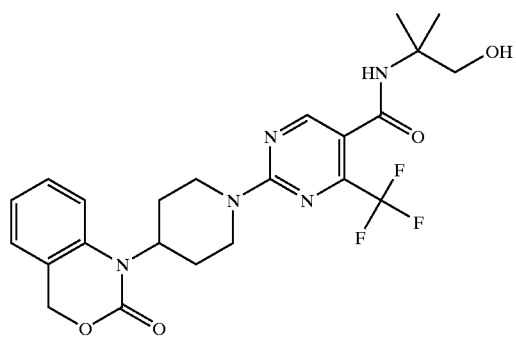

MS: APCI(+ve) 493(M+1)

EXAMPLE 142

N-(1,1-Diethylprop-2-ynyl)-2-[4-(2-oxo-2H-3,1-benzoxazin-1(4H)-yl)piperidin-1-yl]-4-(trifluoromethyl)pyrimidine-5-carboxamide

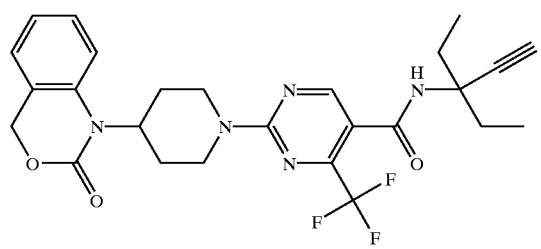

MS: APCI(+ve) 515(M+1)

EXAMPLE 143

N-(2-Hydroxy-1-methylethyl)-2-[4-(2-oxo-2H-3,1-benzoxazin-1(4H)-yl)piperidin-1-yl]-4-(trifluoromethyl)pyrimidine-5-carboxamide

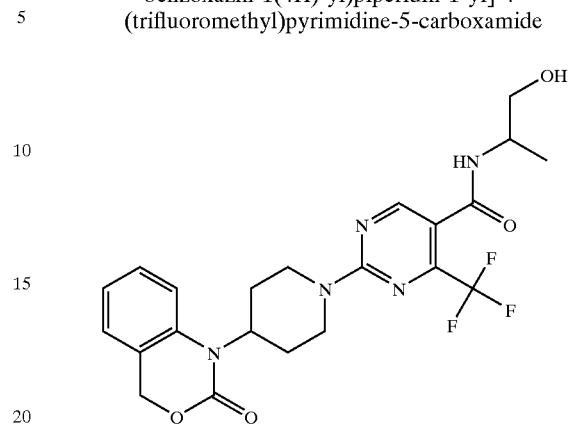

MS: APCI(+ve) 479(M+1)

EXAMPLE 144

N-[1-Methyl-2-(methyloxy)ethyl]-2-[4-(2-oxo-2H-3,1-benzoxazin-1(4H)-yl)piperidin-1-yl]-4-(trifluoromethyl)pyrimidine-5-carboxamide

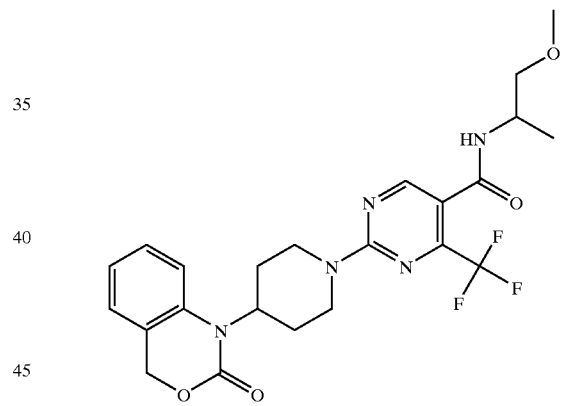

MS: APCI(+ve) 493(M+1)

EXAMPLE 145

N-(1-Methylethyl)-2-[4-(2-oxo-2H-3,1-benzoxazin-1(4H)-yl)piperidin-1-yl]pyrimidine-5-carboxaamide

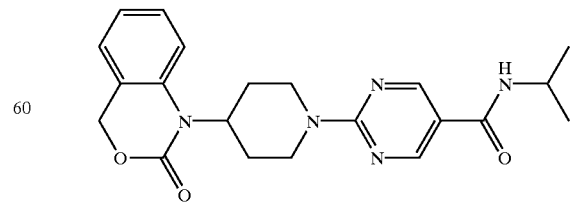

(i) N-(1-Methylethyl)-2-(methylthio)pyrimidine-5-carboxamide

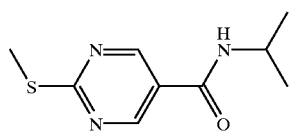

The product was prepared from N-(1-methylethyl)-2-(methylthio)pyrimidine-5-carboxylic acid (Acta Chem Scand., Ser.B (1986), B40(9), 764–767.) (0.78 g), carbonyldiimidazole (0.82 g) and isopropylaniine (0.3 g) using the method of example 115 step (i). Yield 0.66 g.

MS: APCI(+ve) 212 (M+1)

(ii) N-(1-Methylethyl)-2-[4-(2-oxo-2H-3,1-benzoxazin-1(4H)-yl)piperidin-1-yl]pyrimidine-5-carboxamide The product from step (i) (0.66 g) was dissolved in chloroform (50 ml) and to this solution was added 3-chloroperoxybenzoic acid (2.02 g). The mixture was stirred for 1 h at room temperature before being washed with an aqueous solution of sodium metabisulphite followed by aqueous sodium bicarbonate. The organic layer was dried and evaporated under reduced pressure. The residue was dissolved in 1-methyl-2-pyrrolidinone (4 ml) and this solution treated with N,N-diisopropylethylamine (0.5 ml) followed by 1-piperidin-4-yl-1,4-dihydro-2H-3,1-benzoxazin-2-one hydrochloride (0.2 g) before being heated at 60° C. for 2 h. The mixture was partitioned between water and ethyl acetate, the organic layer washed with water, dried and evaporated under reduced pressure. Purification was by chromatography eluting with ethyl acetate/isohexane (2/1). Yield 0.03 g as a solid.

MS: APCI(+ve) 396 (M+1)

1H NMR: δ (DMSO-d6) 8.77(2H, s), 8.07(1H, d), 7.41–7.29(3H, m), 7.12(1H, t), 5.14(2H, s), 4.88(2H, d), 4.28–4.22(1H, m), 4.11–4.02(1H, m), 3.12(2H, t), 2.45–2.3 (2H, m), 1.89(2H, d), 1.16(6H, d)

MP: 236–239° C.

EXAMPLE 146

N-(1-Methylethyl)-2-[4-(2-oxo-2H-3,1-benzoxazin-1(4H)-yl)piperidin-1-yl]-1,3-thiazole4-carboxamide

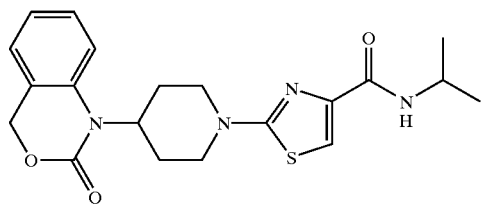

(i) 2-Bromo-N-(1-methylethyl)-1,3-thiazole4-carboxamide

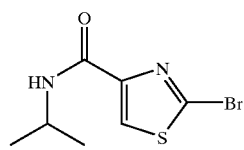

The product was prepared from 2-bromo-N-(1-methylethyl)-1,3-thiazole-4-carboxylic acid (WO 9848799) (0.77 g), carbonyldiimidazole (0.66 g) and isopropylamine (0.24 g) using the method of example 115 step (i). Yield 0.82 g.

1H NMR: δ (DMSO-d6) 8.25(1H, s), 8.24–8.18(1H, m), 4.14–4.02(1H, m), 1.16(6H, d)

(ii) N-(1-Methylethyl)-2-[4-(2-oxo-2H-3,1-benzoxazin-1(4H)-yl)piperidin-1-yl]-1,3-thiazole4-carboxamide The title compound was prepared from the product of step (i) (0.16 g) and 1-piperidin-4-yl-1,4-dihydro-2H-3,1-benzoxazin-2-one hydrochloride (0.15 g) using the method of example 115 step (ii). Yield 0.04 g.

MS: APCI(+ve) 401 (M+1)

1H NMR: δ (DMSO-d6) 7.68(1H, d), 7.43–7.29(4H, m), 7.13(1H, t), 5.16(2H, s), 4.22–3.99(4H, m), 3.29–3.18(2H, m), 2.64–2.49(2H, m), 1.91(2H, d), 1.16(6H, d)

MP: 214–215° C.

EXAMPLE 147

N-(1-Methylethyl)-3-(methylsulfonyl)-4-[4-(2-oxo-2H-3,1-benzoxazin-1(4H)-yl)piperidin-1-yl]benzamide 4-Fluoro-N-(1-methylethyl)-3-(methylsulfonyl)benzoic acid (J.Med.Chem (1997), 40(13), 2017–2034) (0.45 g) was reacted with carbonyldiimidazole (0.37 g) and isopropylamine (0.25 g) using the method of example 115 step (i) to yield the corresponding amide. Yield 0.50 g.

A solution of this amide (0.50 g) in 1-methyl-2-pyrrolidinone (10 ml) was treated with 1-piperidin-4-yl-1,4-dihydro-2H-3,1-benzoxazin-2-one hydrochloride (0.40 g) followed by N,N-diisopropylethylamine (0.73 g) and the resultant mixture heated at 100° C. for 14 h. The mixture was then partitioned between water and ethyl acetate, the organic layer washed with water, dried and evaporated under reduced pressure. The resultant solid was washed with ethyl acetate (10 ml) followed by ethanol (1 ml) to yield the desired product as a solid (0.13 g).

MS: APCI(+ve) 472 (M+1)

1H NMR: δ (DMSO-d6) 8.47(1H, d), 8.38(1H, d), 8.16 (1H, d), 7.63(1H, d), 7.42(1H, t), 7.32–7.29(2H, m), 7.13 (1H, t), 5.16(2H, s), 4.14–4.05(2H, m), 3.49(3H, s), 3.32–3.29(2H, m), 3.03(2H, t), 2.83–2.76(2H, m), 1.91–1.88 (2H, m), 1.17(6H, d)

MP: 240–242° C.

EXAMPLE 148

N-[(1R)-1-(Aminocarbonyl)-2-methylpropyl]-5-chloro-6-[4-(2-oxo-2H-3,1-benzoxazin-1(4H)-yl)piperidin-1-yl]pyridine-3-carboxamide

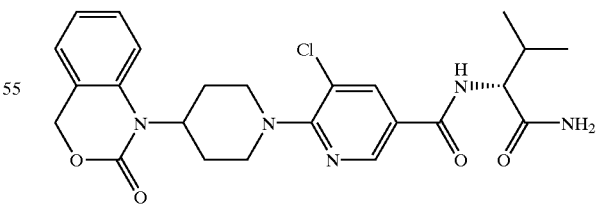

(i) 5-Chloro-6-[4-(2-oxo-2H-3,1-benzoxazin-1(4H)-yl)piperidin-1-yl]pyridine-3-carboxylic acid The title compound was prepared from 5,6-dichloronicotinic acid (2.2 g) and 1-piperidin-4-yl-1,4-dihydro-2H-3,1-benzoxazin-2-one hydrochloride (3.0 g) using the method of example 115 step (ii). Yield 0.037 g MS: APCI(+ve) 388 (M+1)

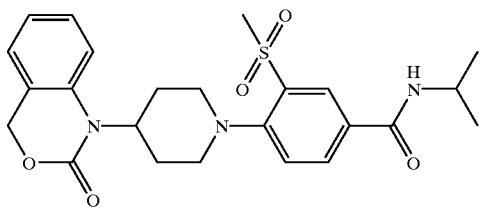

(ii) N-[(1R)-1-(Aminocarbonyl)-2-methylpropyl]-5-chloro-6-[4-(2-oxo-2H-3,1-benzoxazin-1(4H)-yl)piperidin-1-yl]pyridine-3-carboxamide The product of step (i) (0.14 g) was dissolved in 1-methyl-2-pyrrolidinone (4 ml) and to this solution was added carbonyldiimidazole (0.064 g) the mixture was stirred at room temperature for 1 h and then treated with D-valinamide hydrochloride (0.11 g) and N,N-diisopropylethylamine (0.10 g). After stirring for 18 h at room temperature the mixture was partitioned between aqueous sodium bicarbonate and ethyl acetate, the organic layer was washed with water, dried and evaporated under reduced pressure. The resultant solid was washed with ethyl acetate to yield 0.06 g of product.

MS: APCI(+ve) 486 (M+1)

1H NMR: δ (DMSO-d6) 8.68(1H, d), 8.31–8.27(2H, m), 7.46(1H, s), 7.42–7.29(3H, m), 7.13(1H, t), 7.06(1H, s), 5.15(2H, s), 4.26(1H, t), 4.19–4.04(3H, m), 3.07(2H, t), 2.72–2.60(2H, m), 2.14–2.07(1H, m), 1.90(2H, d), 0.94–0.91(6H, m)

MP: 140–143° C.

EXAMPLE 149

5-Chloro-N-(2-hydroxy-1-methylethyl)-6-[4-(2-oxo-2H-3,1-benzoxazin-1(4H)-yl)piperidin-1-yl]pyridine-3-carboxamide

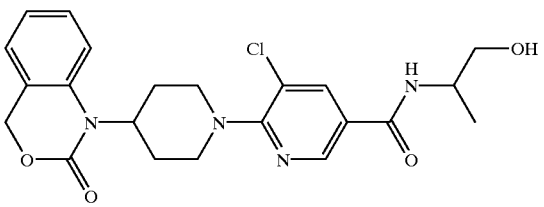

The title compound was prepared from the product of example 148 step (i) (0.14 g), carbonyldiimidazole (0.064 g) and DL-2-amino-1-propanol (0.05 g) using the method of example 115 step (i). Purification was by chromatography eluting with 20% ethyl acetate/isohexane. Yield 0.04 g as a solid.

MS: APCI(+ve) 445 (M+1)

1H NMR: δ (DMSO-d6) 8.64(1H, d), 8.20(1H, d), 8.15 (1H, d), 7.42–7.29(3H, m), 7.12(1H, t), 5.15(2H, s), 4.72 (1H, t), 4.15–3.98(4H, m), 3.48–3.37(2H, m), 3.06(2H, t), 2.73–2.62(2H, m), 1.89(2H, d), 1.13–1.09(3H, m)

MP: 125–128° C.

EXAMPLE 150

5-Chloro-N-(1,1-dimethylprop-2-ynyl)-6-[4-(2-oxo-2H-3,1-benzoxazin-1(4H)-yl)piperidin-1-yl]pyridine-3-carboxamide

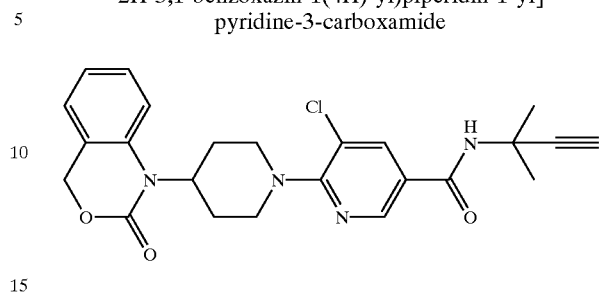

The title compound was prepared from the product of example 148 step (i) (0.14 g), carbonyldiimidazole (0.064 g) and 1,1-dimethylpropargylamine (0.06 g) using the method of example 115 step (i). Purification was by chromatography eluting with ethyl acetate/isohexane (2/3). Yield 0.03 g as a solid.

MS: APCI(+ve) 453 (M+1)

1H NMR: δ (DMSO-d6) 8.62(1H, d), 8.29(1H, s), 8.18 (1H, d), 7.42–7.29(3H, m), 7.12(1H, t), 5.15(2H, s), 4.19–4.07(3H, m), 3.12(1H, s), 3.07(2H, t), 2.72–2.60(2H, m), 1.90(2H, d), 1.60(6H, s)

MP: 135–138° C.

EXAMPLE 151

N-(2-Amino-1-cyano-2-oxoethyl)-5-chloro-6-[4-(2-oxo-2H-3,1-benzoxazin-1(4H)-yl)piperidin-1-yl]pyridine-3-carboxamide

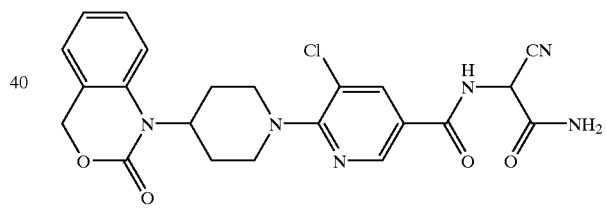

The product of example 148 step (i) (0.14 g) was stirred as a suspension in dichloromethane (4 ml) and to this mixture was added oxalyl chloride (0.05 g) followed by N,N-dimethylformamide (0.01 g). After stirring for 1 h at room temperature the mixture was treated with 2-aminocyanoacetanide (0.14 g) 1-methyl-2-pyrrolidinone (3 ml) and then N,N-diisopropylethylamine (1 ml), stirring was then continued for a further 18 h at room temperature. The reaction mixture was partitioned between aqueous sodium bicarbonate and ethyl acetate, the organic layer was washed with water, dried and evaporated under reduced pressure. Purification was by chromatography eluting with 25% ethyl acetate/isohexane. Yield 0.09 g as a solid.

MS: APCI(+ve) 469 (M+1)

1H NMR: δ (DMSO-d6) 9.63(1H, d), 8.69(1H, d), 8.25 (1H, d), 7.83(1H, s), 7.68(1H, s), 7.40(1H, t), 7.34–7.30(2H, m), 7.13(1H, t), 5.67(1H, d), 5.15(2H, s), 4.17–4.14(3H, m), 3.10(2H, t), 2.69–2.61(2H, m), 1.91(2H, d)

MP: 159–162° C.

EXAMPLE 152

N-[(1R)-1-(Aminocarbonyl)-3-methylbutyl]-5-chloro-6-[4-(2-oxo-2H-3,1-benzoxazin-1(4H)-yl)piperidin-1-yl]pyridine-3-carboxamide

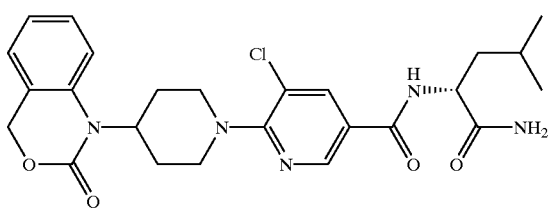

The title compound was prepared from the product of example 148 step (i) (0.15 g) and (R)-leucinamide hydrochloride (0.07 g) according to the method of example 115, step (i). Yield 0.05 g as a solid.

MS: APCI(+ve) 500 (M+1)

1H NMR: δ (DMSO-d6) 8.68(1H, d), 8.45(1H, d), 8.27 (1H, d), 7.42–7.29(4H, m), 7.12(1H, t), 6.98(1H, s), 5.15 (2H, s), 4.44–4.41(1H, m), 4.15–4.07(3H, m), 3.07(2H, t), 2.68–2.64(2H, m), 1.90(2H, d), 1.70–1.54(3H, m), 0.92–0.86(6H, m)

MP: 139–142° C.

EXAMPLE 153

N-[(1S)-1-(Amiocarbonyl)-2-methylpropyl]-5-chloro-6-[4-(2-oxo-2H-3,1-benzoxazin-1(4H)-yl)piperidin-1-yl]pyridine-3-carboxamide

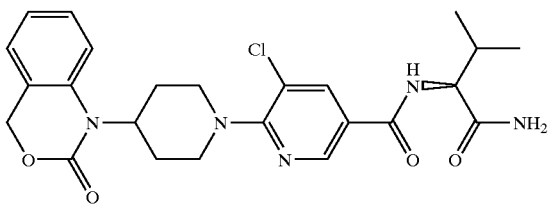

The title compound was prepared from the product of example 148 step (i) (0.15 g) and (S)-valinamide hydrochloride (0.08 g) according to the method of example 115, step (i). Yield 0.03 g as a solid.

MS: APCI(+ve) 486 (M+1)

1H NMR: δ (DMSO-d6) 8.68(1H, t), 8.31–8.28(2H, m), 7.46–7.29(4H, m), 7.13(1H, t), 7.06(1H, s), 5.15(2H, s), 4.24–4.00(4H, m), 3.07(2H, t), 2.73–2.61(2H, m), 2.14–2.05 (1H, m), 1.90(2H, d), 0.94(3H, s), 0.92(3H, s)

EXAMPLE 154

N-[(1S)-1-(Aminocarbonyl)-3-methylbutyl]-5-chloro-6-[4-(2-oxo-2H-3,1-benzoxazin-1(4H)-yl)piperidin-1-yl]pyridine-3-carboxamide

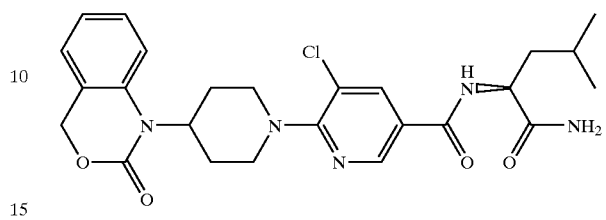

The title compound was prepared from the product of example 148 step (i) (0.15 g) and (S)-leucinamide hydrochloride (0.07 g) according to the method of example 115, step (i). Yield 0.04 g as a solid.

MS: APCI(+ve) 500 (M+1)

1H NMR: δ (DMSO-d6) 8.68(1H, d), 8.45(1H, d), 8.27 (1H, d), 7.42–7.29(4H, m), 7.13(1H, t), 6.98(1H, s), 5.15 (2H, s), 4.44–4.42(1H, m), 4.15–4.04(3H, m), 3.07(2H, t), 2.68–2.64(2H, m), 1.90(2H, d), 1.66–1.54(3H, m), 0.92–0.86(6H, m)

MP: 139–142° C.

EXAMPLE 155

5-Chloro-N-(1-methylethyl)-6-[4-(3-oxo-2,3-dihydro-4H-1,4-benzoxazin-4-yl)piperidin-1-yl]pyridine-3-carboxamide

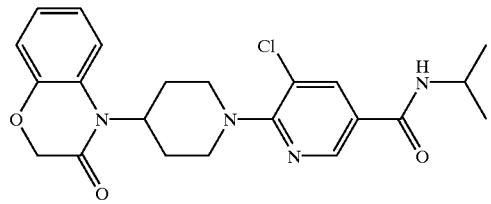

The title compound was prepared from 4-piperidin-4-yl-4H-benzo[1,4]oxazin-3-one hydrochloride (WO 9502405) (0.13 g) and the product from example 117 step (i) (0.13 g) according to the method of example 115 step (ii). Yield 0.04 g as a solid.

MS: APCI(+ve) 429 (M+1)

1H NMR: δ (DMSO-d6) 8.64(1H, d), 8.25(1H, d), 8.18 (1H, d), 7.40(1H, d), 7.12–7.03(3H, m), 4.52(2H, s), 4.37–4.32(1H, m), 4.11–4.04(3H, m), 3.03(2H, t), 2.77–2.6 (2H, m), 1.82(2H, d), 1.16(6H, d)

MP: 85–88° C.

EXAMPLE 156

N-(1-Methylethyl)-3-nitro-4-[4-(2-oxo-2H-3,1-benzoxazin-1(4H)-yl)piperidin-1-yl]benzamide

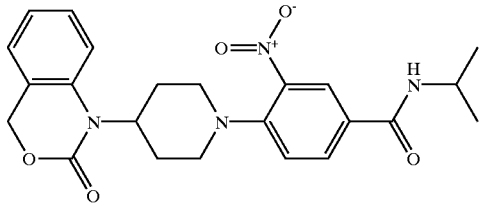

The product from example 8 step (i) (0.05 g) was reacted with isopropylamine (0.02 ml) using the method of example 115 step (i) in N,N-dimethylformamide (2 ml). Purification was by chromatography eluting with (2:1) ethyl acetate/isohexane. Yield 0.035 g as a solid.

MS: APCI(+ve) 439(M+1)

1H NMR: δ (CDCl$_3$) 8.17(1H, m), 7.93–7.90(1H, m), 7.38–7.09(5H, m), 5.92–5.90(1H, d), 5.10(2H, s), 4.32–4.16 (2H, m), 3.53–3.49(2H, m), 3.17–3.10(2H, m), 2.90–2.80 (2H, m), 1.96–1.93(2H, m), 1.28–1.26(6H, d)

MP: 193–195° C.

EXAMPLE 157

N-[(1S)-1-(Aminocarbonyl)-2-methylbutyl]-3-nitro-4-[4-(2-oxo-2H-3,1-benzoxazin-1(4H)-yl)piperidin-1-yl]benzamide

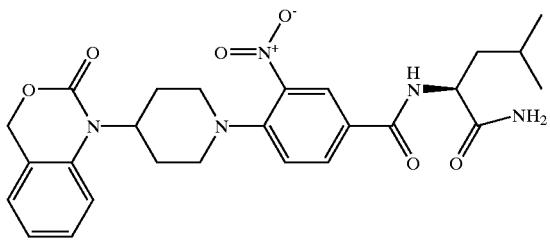

The product from example 8 step (i) (0.05 g) was reacted with (S)-leucinamide hydrochloride (0.025 g) using the method of example 115 step (i) in N,N-dimethylformamide (2 ml). Purification was by chromatography eluting with ethyl acetate. Yield 0.025 g as a solid.

MS: APCI(+ve) 510(M+1)

1H NMR: δ (CDCl$_3$) 8.29–7.09(6H, m), 6.90(1H, d), 6.22(1H, br s), 5.56(1H, br s), 5.10(2H, s), 4.73–4.11(2H, m), 3.50–2.80(6H, m), 1.97–1.70(5H, m), 1.27–1.22(1H, m), 0.99(6H, d)

MP: 146–149° C.

EXAMPLE 158

N-(1-Methylethyl)-2-[4-(2-oxo-2H-3,1-benzoxazin-1(4H)-yl)piperidin-1-yl]-4-(trifluoromethyl)-5-pyrimidine-5-carboxamide.

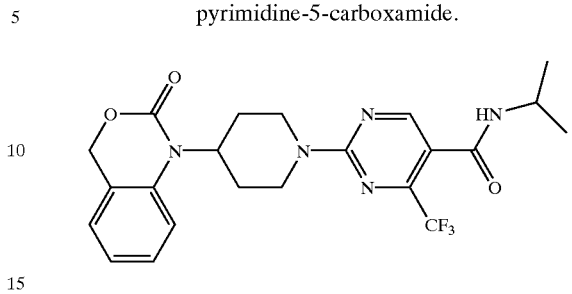

(i) N-(1-Methylethyl)-2-chloro-4-(trifluoromethyl) pyrimidine-5-carboxamide.

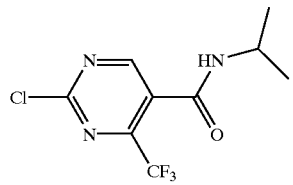

2-Chloro-4-(trifluoromethyl)pyrimidine-5-carbonyl chloride (1.0 g) in dry N,N-dimethylformamide (5 ml) was treated with isopropylamine (0.4 ml) at 0° C. The reaction mixture was stirred at 0° C. for 30 min, diluted with water, extracted with ethyl acetate, dried, and evaporated under reduced pressure. Purification was by chromatography eluting with 50% ethyl acetate/dichloromethane. Yield 0.74 g as a solid.

MS: APCI(+ve) 268(M+1)

(ii) N-(1-Methylethyl)-2-[4-(2-oxo-2H-3,1-benzoxazin-1(4H)-yl]piperidin-1-yl]-4-(trifluoromethyl)-5-pyrimidine-5-carboxamide.

The title compound was prepared from the product from step (i) (0.092 g) and 1-piperidin-4-yl-1,4-dihydro-2H-3,1-benzoxazin-2-one hydrochloride (0.1 g) using the method of example 115 step(ii). Purification was by chromatography eluting with (1:3) ethyl acetate/dichloromethane. Yield 0.110 g as a solid.

MS: APCI(+ve) 464(M+1)

1H NMR: δ (CDCl$_3$) 8.58(1H, s), 7.38–7.08(4H, m), 5.62–5.60(1H, d), 5.10–5.05(4H, m), 4.29–4.15(2H, m), 3.06–2.62(4H, m), 1.99–1.95(2H, d), 1.25–1.24(6H, d)

MP: 217–219° C.

EXAMPLE 159

3-Chloro-N-(1-methylethyl)-4-[4-(2-oxo-2H-3,1-benzoxazin-1(4H)-yl)piperidin-1-yl]benzamide

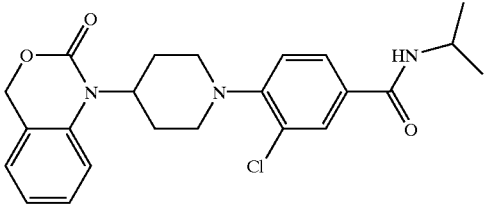

(i) 1,1-Dimethylethyl 3-nitro-4-[4-(2-oxo-2H-3,1-benzoxazin-1(4H)-yl)piperidin-1-yl]benzoate

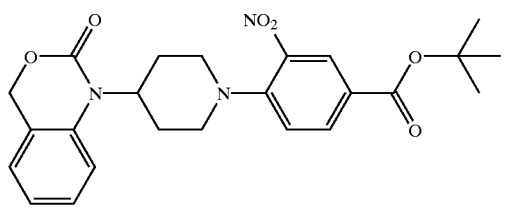

The product was prepared from 3-nitro-4-chloro-t-butylbenzoate (0.96 g) and 1-piperidin-4-yl-1,4-dihydro-2H-3,1-benzoxazin-2-one hydrochloride (1.0 g) using the method of example 115 step (ii). Purification was by chromatography eluting with 50% ethyl acetate/isohexane. Yield 2.1 g as an oil.

MS: APCI(+ve) 454(M+1)

(ii) 3-Amino-1,1-dimethylethyl-4-[4-(2-oxo-2H-3,1-benzoxazin-1(4H)-yl)piperidin-1-yl]benzoate

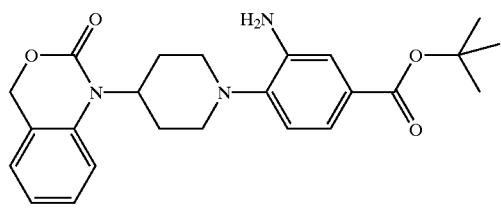

The product from step (i) (1.9 g) was dissolved in glacial acetic acid (20 ml) and treated with reduced iron powder (1.9 g). The mixture was stirred vigorously for 2 h at room temperature. The mixture was filtered through a pad of celite and the filtrate evaporated under reduced pressure. Purification was by chromatography eluting with (1:5) ethyl acetate/dichloromethane. Yield 0.975 g as a solid.

MS: APCI(+ve) 424(M+1)

(iii) 3-Chloro-N-(1-methylethyl)-4-[4-(2-oxo-2H-3,1-benzoxazin-1(4H)-yl)piperidin-1-yl]benzamide Product from step (ii) (0.39 g) was treated with copper(II) chloride (0.148 g), isoamylnitrite (0.25 ml) in acetonitrile (10 ml) and heated to 65° C. for 4 h. The reaction mixture was evaporated under reduced pressure to an oil. The oil was treated with trifluoroacetic acid/dichloromethane (1:1) and stirred at room temperature for 2 h then evaporated under reduced pressure. The residue was dissolved in N,N-dimethylformnamide (5 ml), bromo-tris-pyyrolidino-phosphonium hexafluorophosphate (0.116 g), isopropylamine (0.054 ml) and N,N-diisopropylethylamine (0.06 ml) were added and stirred at room temperature for 16 h. The mixture was evaporated under reduced pressure. Purification was by chromatography eluting with (1:3) ethyl acetate/dichloromethane. Yield 0.017 g as a solid.

MS: APCI(+ve) 428(M+1)

1H NMR: δ (CDCl$_3$) 7.76–7.06(7H, m), 5.82–5.80(1H, d), 5.10(2H, s), 4.31–4.15(2H, m), 3.65–3.62(2H, m), 2.95–2.82(4H, m), 1.98–1.95(2H, d), 1.27–1.25(6H, d).

EXAMPLE 160

3-Amino-N-(1-methylethyl)-4-[4-(2-oxo-2H-3,1-benzoxazin-1(4H)-yl)piperidin-1-yl]benzamide

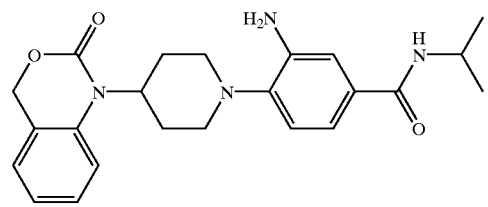

The title compound was prepared from the product of example 156 using the method described in example 159 step (ii). Yield 0.6 g as a solid.

MS: APCI(+ve) 409(M+1)

1H NMR: δ (DMSO-d6) 7.89–7.86(1H, d), 7.39–6.91 (7H, m), 5.15(2H, s), 4.84–4.82(2H, s), 4.08–3.99(2H, m), 3.23–3.21(2H, m), 2.77–2.67(4H, m), 1.88–1.85(2H, m), 1.19–1.12(6H, d)

EXAMPLE 161

N-(1-Methylethyl)-4-[4-(2-oxo-2H-3,1-benzoxazin-1(4H)-yl)piperidin-1-yl]benzamide

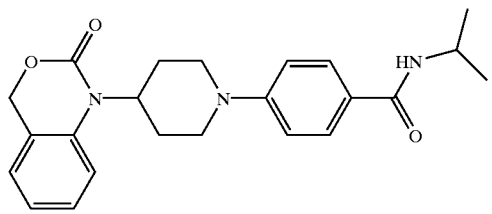

(i) 1,1-Dimethylethyl 4-[4-(2-oxo-2H-3,1-benzoxazin-1(4H)-yl)piperidin-1-yl]benzoate

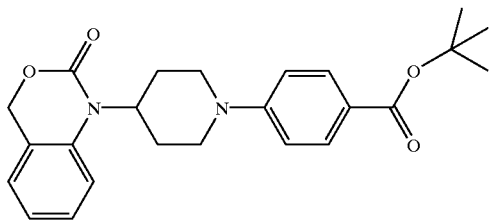

A solution of sodium nitrite (0.11 g) in water (1 ml) was added to a stirred solution of the product from example 159 step (ii) (0.456 g) in acetonitrile (10 ml) at room temperature. After 1 h a solution of iron sulphate (0.3 g) in N,N-dimethylformamide (20 ml) was added and the mixture stirred for a further 30 min. The mixture was partitioned between ethyl acetate and water, the organics dried and evaporated under reduced pressure. Purification was by chromatography eluting with 20% ethyl acetate/isohexane. Yield 0.29 g as an oil.

MS: APCI(+ve) 409(M+1)

(ii) N-(1-Methylethyl)-4-[4-(2-oxo-2H-3,1-benzoxazin-1(4H)-yl)piperidin-1-yl]benzamide A solution of the product from step (i) (0.29 g) in a mixture of trifluoroacetic acid (10 ml) and dichloromethane (10 ml) was stirred at room temperature for 1 h. The solution was evaporated under reduced pressure, the residue dissolved in N,N-dimethylformamide then bromo-tris-pyyrolidino-phosphonium hexafluorophosphate (0.16 g), isopropylamine (0.06 ml) and N,N-diisopropylethylamine (0.06 ml) added. The solution was stirred at room temperature for 16 h then evaporated under reduced pressure. Purification was by chromatography eluting with (1:5) ethyl acetate/dichloromethane. Yield 0.01 g as a solid.

MS: APCI(+ve) 394(M+1)

1H NMR: δ (DMSO-d6) 7.89–6.95(9H, m), 5.13(2H, s), 4.15–3.97(4H, m), 3.01–2.95(2H, m), 2.59–2.49(2H, m), 1.85–1.82(2H, d), 1.13(6H, d)

EXAMPLE 162

N-[(1S)-1-(Aminocarbonyl)-3-methylbutyl]-4-[4-(2-oxo-2H-3,1-benzoxazin-1(4H)-yl)piperidin-1-yl] benzamide

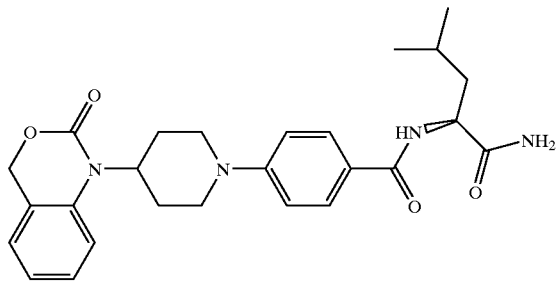

The title compound was prepared from the product of example 161 step (i) (0.06 g) and (S)-leucinamide hydrochloride (0.056 g) using the method of example 161 step (ii). Purification was by chromatography eluting with (5:1) ethyl acetate/dichloromethane. Yield 0.01 g as a solid.

MS: APCI(+ve) 465(M+1)

1H NMR: δ (DMSO-d6) 8.04–6.92(11H, m), 5.13(2H, s), 4.44–3.99(4H, m), 3.03–2.93(2H, m), 2.60–2.49(2H, m), 1.85–1.50(5H, m), 0.88(6H, d)

EXAMPLE 163

3-(Ethylamino)-N-(1-methylethyl)-4-[4-(2-oxo-2H-3,1-benzoxazin-1(4H)-yl)piperidin-1-yl]benzamide

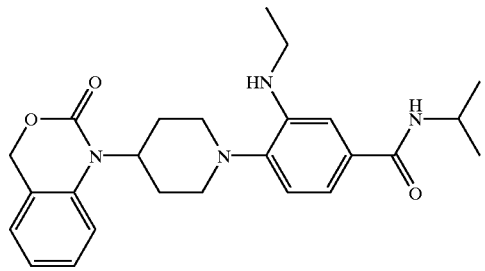

Sodium triacetoxyborohydride (0.1 g) was added to a solution of the product from example 160 (0.1 g), acetaldehyde (0.015 ml), acetic acid (1 drop) in N,N-dimethylformamide (10 ml). The reaction mixture was stirred at room temperature for 16 h. The mixture was diluted with water, extracted with ethyl acetate, dried, and evaporated under reduced pressure. Yield 0.035 g.

MS: APCI(+ve) 437(M+1)

1H NMR: δ (DMSO-d6) 7.96–6.98(8H, m), 5.15(2H, s), 4.73–4.70(1H, t), 4.13–3.99(2H, m), 3.25–3.14(4H, m), 2.81–2.64(4H, m), 1.90–1.88(2H, m), 1.26–1.14(9H, m)

EXAMPLE 164

3-(Diethylamino)-N-(1-methylethyl)-4-[4-(2-oxo-2H-3,1-benzoxazin-1(4H)-yl)piperidin-1-yl] benzamide

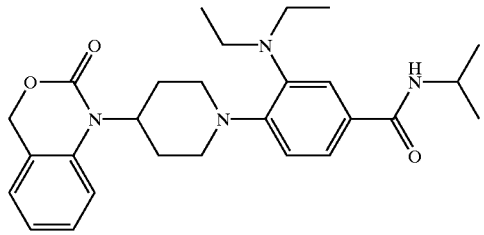

The title compound was obtained from the reaction mixture in example 163. Yield 0.052 g.

MS: APCI(+ve) 465(M+1)

1H NMR: δ (DMSO-d6) 7.97–6.90(8H, m), 5.15(2H, s), 4.11–3.99(2H, m), 3.86–3.83(2H, m), 3.31–3.18(4H, m), 2.72–2.63(4H, m), 1.86(2H, m), 1.19–1.14(6H, d), 1.03–0.95(6H, m)

EXAMPLE 165

N-(1-Methylethyl)-3-[(methylsulfonyl)amino]-4-[4-(2-oxo-2H-3,1-benzoxazin-1(4H)-yl)piperidin-1-yl] benzamide

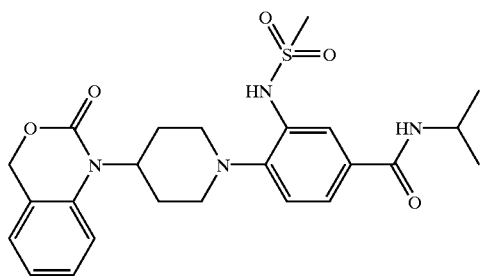

The title compound was prepared from the product of example 160 (0.1 g) and methanesulphonylchloride (0.02 ml) in dichloromethane (10 ml) at 0° C. in the presence of 2,6-lutidine (0.085 ml). The reaction mixture was stirred at room temperature for 16 h. The mixture was evaporated, dissolved in ethyl acetate, washed with water, dried, and evaporated under reduced pressure. Purification was by chromatography eluting with (3:1) ethyl acetate/isohexane. Yield 0.066 g as a solid.

MS: APCI(+ve) 487(M+1)

1H NMR: δ (DMSO-d6) 8.63(1H,s), 8.16–8.13(1H, d), 7.76–7.10(7H, m), 5.16(2H, s), 4.14–3.99(2H, m), 3.27–3.23(2H, m), 3.19(3H, s), 2.93–2.70(4H, m), 1.89–1.86(2H, m), 1.17–1.14(6H, d)

EXAMPLE 166

5-Chloro-N-(1-methylethyl)-6-[4-(2-oxo-1,3-benzoxazol-3(2H)-yl)piperidin-1-yl]pyridine-3-carboxamide

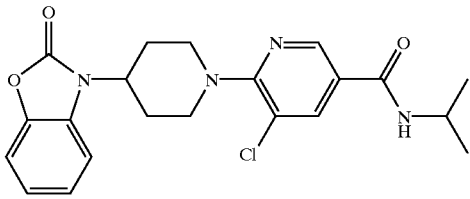

(i) 1,1-Dimethylethyl 4-(2-oxo-1,3-benzoxazol-3(2H)-yl)piperidine-1-carboxylate

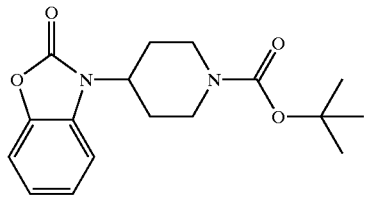

2-Benzoxazolinone (1 g) was added to a cooled solution of triphenylphoshine (2.13 g) and diethylazodicarboxylate (1.28 ml) in dry tetrahydrofuran (20 ml). After 10 min at 0° C., N-(t-butoxy)-4-hydroxypiperidine (1.63 g) (Tetrahedron Letters, 1996, 6439–6442) was added portionwise. The reaction mixture was stirred at room temperature for 16 h. The solution was diluted with water, extracted with ethyl acetate, dried and evaporated under reduced pressure. Purification was by chromatography eluting with (1:2) diethylether/isohexane. Yield 0.5 g as an oil.

MS: APCI(+ve) 219(M+1)-BOC (ii) 3-Piperidin-4-yl-1,3-benzoxazol-2(3H)-one, trifluoroacetic acid salt

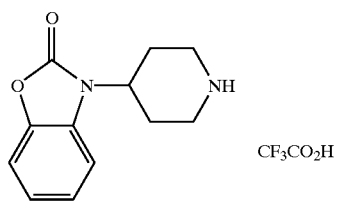

The product from step (i) (0.5 g) was stirred at room temperature in (1:1) trifluoroacetic acid/dichloromethane (10 ml) for 30 min. The reaction mixture was evaporated under reduced pressure to give an oil. Used crude.

MS: APCI(+ve) 219(M+1)

(iii) 5-Chloro-N-(1-methylethyl)-6-[4-(2-oxo-1,3-benzoxazol-3(2H)-yl)piperidin-1-yl]pyridine-3-carboxamide The title compound was prepared from the product of example 117 step(i) (0.53 g) and the product from step (ii) by the method described in example 115 step (ii). Purification was by chromatography eluting with 50% ethyl acetate/isohexane. Yield 0.28 g as a solid.

MS: APCI(+ve) 415(M+1)

1H NMR: δ (DMSO-d6) 8.66–7.12(7H, m), 4.44–4.38 (1H, m), 4.10–4.05(3H, m), 3.09–3.03(2H, t), 2.45–2.35(2H, m), 1.95–1.92(2H, m), 1.17–1.15(6H, d)

MP: 162–168° C.

EXAMPLES 167–169

(i) 4-Chloro-N-(1-methylethyl)-3-nitrobenzamide

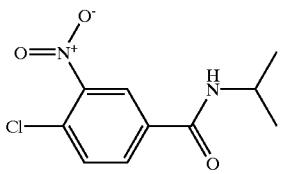

Isopropylamine (1.28 ml) was added dropwise to a stirred solution of 4-chloro-3-nitrobenzoylchloride (3.0 g) and triethylamine (2.8 ml) in dichloromethane (30 ml) at room temperature. After 2 h the mixture was partitioned between ethyl acetate and water, the organics dried and evaporated under reduced pressure. Yield 2.87 g.

1H NMR: δ (DMSO-d6) 8.58(1H, d), 8.51(1H, d), 8.15 (1H, dd), 7.89(1H, d), 4.14–4.06(1H, m), 1.18(6H, d)

(ii) Examples 167–169

A solution of the product from step (i) (1 mg), N,N-diisopropylethylamine (3 equiv.), the appropriate amine (1.5 equiv.) in 1-methyl-2-pyrrolidinone (0.16 ml) were heated at 65° C. for 30 h. The reaction mixture was evaporated to dryness and the residue dissolved in dimethylsulphoxide (0.4 ml).

EXAMPLE 167

N-(1-Methylethyl)-3-nitro-4-[4-(2-oxo-3,4-dihydroquinolin-1(2H)-yl)piperidin-1-yl]benzamide

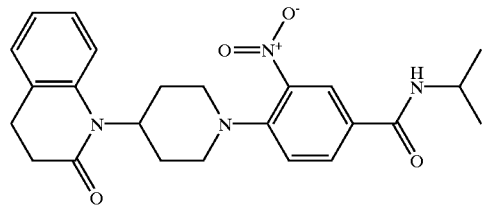

MS: APCI(+ve) 436(M+1)

EXAMPLE 168

4-[4-(7-Chloro-2-oxo-2H-3,1-benzoxazin-1(4H)-yl)piperidin-1-yl]-N-(1-methylethyl-3-nitrobenzamide

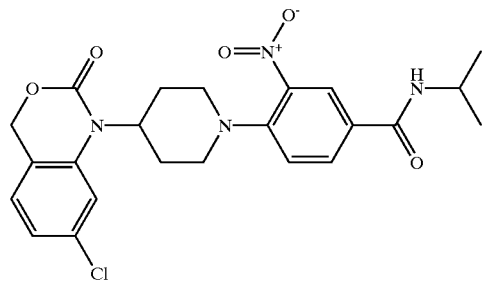

MS: APCI(+ve) 472(M+1)

EXAMPLE 169

5-Chloro-N-(1-methylethyl)-6-[4-(2-oxo-3,4-dihydroquinolin-1(2H)-yl)piperidin-1-yl]pyridine-3-arboxamide

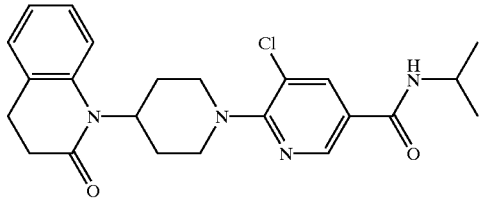

The title compound was prepared from 1-piperidin-4-yl-3,4-dihydro-1H-quinolin-2-one (0.03 g) and the product from example 117 step (i) (0.03 g) by the method of example 115 step (ii). Purification was by chromatography eluting with 50% ethyl acetate/I-hexane. Yield 0.017 g as a white solid.

MS: APCI(+ve) 427 (M+1)

1H NMR: δ (DMSO-d6) 8.49(1H, d), 7.98(1H, d), 7.20 (3H, m), 7.02(1H, t), 5.83(1H, d), 4.50(1H, m), 4.20(3H, m), 2.98(2H, t), 2.80(4H, m), 2.60(2H, t) 1.83(2H, m), 1.25(6H, d)

EXAMPLE 170

4-[4-(2,2-Dioxido-3,4-dihydro-1H-2,1,3-benzothiadiazin-1-yl)piperidin-1-yl]-N-(1-methylethyl)-3-nitrobenzamide

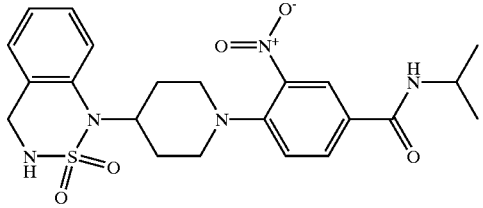

The title compound was prepared from 1-Piperidin-4-yl-3,4-dihydro-1H-benzo[1,2,6]thiadiazine 2,2-dioxide (Chem. Pharm. Bull. (1985), 33(3), 1104–15) (0.05 g) and the product from example 167 step (i) (0.05 g) by the method of example 115 step (ii). Purification was by chromatography eluting with ethyl acetate. Yield 0.03 g as a white solid.

MS: APCI(+ve) 474 (M+1)

1H NMR: δ (DMSO-d6) 8.32 (2H, m), 8.00 (1H, d), 7.72 (1H, t), 7.30 (2H, m), 7.20 (2H, d), 7.10 (1H, t), 4.41(2H, d), 4.10 (3H, m), 3.40 (1H, m), 3.04 (2H, t), 2.00 (4H, m), 1.15 (6H,d).

EXAMPLE 171

1-(1-{2-Chloro-4-[(1H-imidazol-2-ylmethyl)amino]phenyl}piperidin-4-yl)-1,4-dihydro-2H-3,1-benzoxazin-2-one

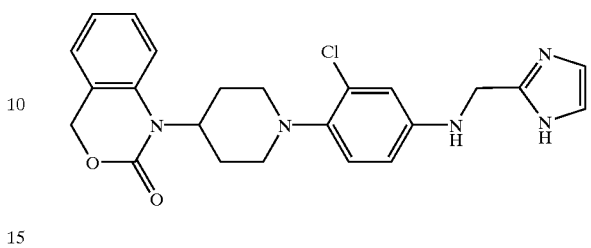

The product of example 120 step (ii) (0.25 g) was dissolved in 1-methyl-2-pyrrolidinone (6 ml) and this solution was treated with 2-imidazolecarboxaldehyde (0.1 g) followed by acetic acid (0.13 g) and then sodium triacetoxyborohydride (0.37 g). the reaction mixture was stirred at room temperature for three days. At the end of this time the mixture was poured in to excess aqueous dilute hydrochloric acid, this solution was allowed to stand for 10 minutes before being basified by addition of excess aqueous sodium bicarbonate. The mixture was extracted with ethyl acetate, the organic layer was washed with water, dried and evaporated under reduced pressure. Purification was by chromatography eluting with methanol/chloroform (7/93). Yield 0.05 g as a solid.

MS: APCl (=ve) 438 (M+1)

1H NMR: δ (DMSO-d6) 11.84 (1H, s), 7.41 (1H, t), 7.31–7.27(2H, m), 7.11(1H, t), 6.97(1H, d), 6.92(2H, s), 6.73(1H, d), 6.57(1H, q), 6.06(1H, t), 5.14(2H, s), 4.19(2H, d), 3.98–3.93(1H, m), 3.15(2H, d), 2.78–2.63(4H, m) 1.83 (2H, d)

MP: 222–224° C.

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds was tested for antagonist activity at the P2X$_7$ receptor. Thus, the test was performed in 96-well flat bottomed microtitre plates, the wells being filled with 100 μl of test solution comprising 80 μl of a suspension of THP-1 cells (2.5×10$^6$ cells/ml) containing 10$^{-4}$M ethidium bromide, 10 μl of a high potassium buffer solution containing 10$^{-5}$M bbATP, and 10 μl of the high potassium buffer solution containing 1×10$^{-4}$M test compound (in 10% v/v DMSO). The plate was covered with a plastic lid and incubated at 37° C. for one hour. The plate was then read in a Spectromax Gemini Fluorescent plate reader excitation 525 nm, emission 610 nm, slit widths: Ex 15 nm, Em 20 nm. For the purposes of comparison, bbATP (a P2X$_7$ receptor agonist) and N-(5-methoxy-2-methylphenyl)-tricyclo[3.3.1.1$^{3,7}$]decane-1-acetamide (WO99/29660, a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. The $pIC_{50}$ was then corrected using a modified Cheng Prusoff calculation based on agonist $A_{50}$ (Trends in Pharmacological Sciences (1993), 14(4), 110–2). Each of the compounds of the Examples demonstrated antagonist activity, having a $pIC_{50}$ figure>5.00.

What is claimed is:

1. A compound of formula (I):

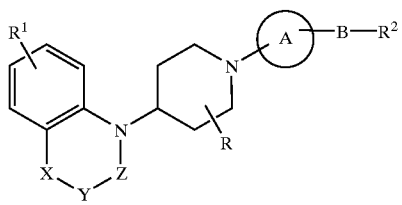

where
- A is phenyl or a 5- or 6-membered heterocyclic ring having one or two heteroatoms selected from O, N or S; and optionally substituted by $C_{1-6}$alkyl, halogen, nitro, amino, alkylamino, $CF_3$, $SO_2Me$, $NHSO_2Me$ or cyano;
- B is C=O, NH or $SO_2$;
- X is O, $(CH_2)p$ where p is 1;
- Y is O, or $CH_2$, provided that X and Y connot both be O or $CH_2$;
- Z is C=O;
- R is hydrogen or $C_{1-6}$alkyl;
- $R^1$ is hydrogen, halogen;
- $R^2$ is phenyl optionally substituted by $CO_2H$, $CO_2$alkyl, $CONH_2$ or $R^2$ is OH, $NHR^3$, $NHCH(R^4)(CHR^5)_nR^6$, $NH-R^7-R^8$, $SO_2NHalkyl$, $NHCOalkyl$, $NHSO_2alkyl$, morpholine, $NR^9R^{10}$, piperazine substituted by phenyl, alkoxyphenyl, pyridyl or fluorophenyl;
- n is 0, 1 or 2;
- $R^3$ is hydrogen, a bi- or tricyclic saturated ring system optionally having a nitrogen atom, piperidinyl, alkylpyrollidine, ethynylcyclohexyl, a 5-membered aromatic ring having 2 or 3 heteroatoms selected from N or S, $C_{4-6}$ cycloalkyl optionally substituted by alkyl, cyano or hydroxy, or $C_{1-8}$ alkyl optionally having an oxygen atom in the alkyl chain and being optionally substituted by one or more substituents selected from ethynyl, cyano, fluoro, di-alkylamino, hydroxy, thioalkyl, $CO_2R^{11}$ or $CONH_2$;
- $R^4$ is hydrogen or alkyl optionally substituted by hydroxy or alkoxy;
- $R^5$ is hydrogen or hydroxy;
- $R^6$ is alkyl, $CO_2R^{11}$, $NHCO_2R^{12}$, $CONH_2$ or a 5 or 6-membered saturated ring having an oxygen atom, a 5-membered heterocyclic ring having one or two heteroatoms selected from O, N or S, or phenyl optionally substituted by one or more groups selected from alkyl, hydroxy, amino, alkoxy, or nitro;
- $R^7$ is a cyclopentane ring;
- $R^8$ is phenyl;
- $R^9$ and $R^{10}$ are independently hydrogen, benzyl, alkenyl, cycloalkyl, alkyl optionally substituted by hydroxy, alkoxy, cyano, dialkylamino, phenyl, pyridyl or $CO_2R^{11}$ or $R^9$ and $R^{10}$ together form a 5- to 7-membered saturated or partially saturated ring optionally having a further heteroaton selected from O, N or S and optionally substituted by one or more groups selected from alkyl (optionally having an oxygen atom in the chain and optionally substituted by hydroxy), COalkyl, $CO_2R^{11}$, $COR^{13}R^{14}$, CHO or piperidine,
- $R^{11}$ is hydrogen or alkyl;
- $R^{12}$ is alkyl; and
- $R^{13}$ and $R^{14}$ are independently hydrogen or alkyl, or a pharmaceutically acceptable salt or solvate thereof.

2. A compound according to claim 1 in which A is phenyl optionally substituted by $C_{1-6}$alkyl, halogen, nitro, amino, alkylamino, $CF_3$, $SO_2Me$, $NHSO_2Me$ or cyano.

3. A compound according to claim 1 in which B is C=O.

4. A compound according to claim 1 in which X is $CH_2$, Y is O and Z is C=O.

5. A compound according to claim 1 in which R is hydrogen.

6. A compound according to claim 1 in which $R^1$ is hydrogen.

7. A compound according to claim 1 in which $R^2$ is $NR^9R^{10}$ where one of $R^9$ or $R^{10}$ is hydrogen and the other is alkyl.

8. A compound according to claim 1 which is:
- 2-({3-Nitro-4-[4-(2-oxo-2H-3,1-benzoxazin-1(4H)-yl) piperidin-1-yl]phenyl}carbonyl)benzoic acid,
- 1-{1-[2-Nitro-4-(phenylcarbonyl)phenyl]piperidin-4-yl}-1,4-dihydro-2H-3,1-benzoxazin-2-one,
- Methyl 2-({3-nitro-4-[4-(2-oxo-2H-3,1-benzoxazin-1 (4H)-yl)piperidin-1-yl]phenyl}carbonyl)benzoate,
- 2-({3-Nitro-4-[4-(2-oxo-2H-3,1-benzoxazin-1(4H)-yl) piperidin-1-yl]phenyl}carbonyl)benzamide,
- Methyl 2-({4-[4-(7-chloro-2-oxo-2H-3,1-benzoxazin-1 (4H)-yl)piperidin-1-yl]-3-nitrophenyl}carbonyl) benzoate,
- N-(1,1-Dimethylethyl)-3-nitro-4-[4-(2-oxo-2H-3,1-benzoxazin-1(4H)-yl)piperidin-1-yl]benzamide,
- N-[(1R)-2-Hydroxy-1-(phenylmethyl)ethyl]-3-nitro-4-[4-(2-oxo-2H-3,1-benzoxazin-1(4H)-yl)piperidin-1-yl] benzamide,
- Methyl 2-[({3-nitro-4-[4-(2-oxo-2H-3,1-benzoxazin-1 (4H)-yl)piperidin-1-yl]phenyl}carbonyl)amino] propanoate,
- 3-Nitro-4-[4-(2-oxo-2H-3,1-benzoxazin-1(4H)-yl) piperidin-1-yl]-N-(tetrahydrofuran-2-ylmethyl) benzamide,
- N-[2-(4-Aminophenyl)ethyl]-3-nitro-4-[4-(2-oxo-2H-3, 1-benzoxazin-1(4H)-yl)piperidin-1-yl]benzamide,
- 3-Nitro-4-[4-(2-oxo-2H-3,1-benzoxazin-1(4H)-yl) piperidin-1-yl]-N-(2,2,2-trifluoroethyl)benzamide,
- Ethyl (2S)-3-methyl-2-[({3-nitro-4-[4-(2-oxo-2H-3,1-benzoxazin-1(4H)-yl)piperidin-1-yl]phenyl}carbonyl) amino]butanoate,
- Methyl 3-hydroxy-2-[({3-nitro-4-[4-(2-oxo-2H-3,1-benzoxazin-1(4H)-yl)piperidin-1-yl]phenyl}carbonyl) amino]propanoate,
- N-[2-(3,4-Dihydroxyphenyl)ethyl]-3-nitro-4-[4-(2-oxo-2H-3,1-benzoxazin-1(4H)-yl)piperidin-1-yl] benzamide,
- 3-Nitro-4-[4-(2-oxo-2H-3,1-benzoxazin-1(4H)-yl) piperidin-1-yl]-N-(2-phenylethyl)benzamide,
- N-[(4-Aminophenyl)methyl]-3-nitro-4-[4-(2-oxo-2H-3, 1-benzoxazin-1(4H)-yl)piperidin-1-yl]benzamide,
- 3-Nitro-4-[4-(2-oxo-2H-3,1-benzoxazin-1(4H)-yl) piperidin-1-yl]-N-(2-thien-2-ylethyl)benzamide, N-[3-(Dimethylamino)-2,2-dimethylpropyl]-3-nitro-4-[4-(2-oxo-2H-3,1-benzoxazin-1(4H)-yl)piperidin-1-yl]benzamide, N-{[2,4-Bis(methyloxy)phenyl]methyl}-3-nitro-4-[4-(2-oxo-2H-3,1-benzoxazin-1(4H)-yl)piperidin-1-yl]benzamide, N-Bicyclo[2.2.1]hept-2-yl-3-nitro-4-[4-(2-oxo-2H-3,1-benzoxazin-1(4H)-yl)piperidin-1-yl]benzamide, N-(2-Fluoroethyl)-3-nitro-4-[4-(2-oxo-2H-3,1-benzoxazin-1(4H)-yl)piperidin-1-yl]benzamide, 3-Nitro-N-[(3-nitrophenyl)methyl]-4-[4-(2-oxo-2H-3,1-benzoxazin-1(4H)-yl)piperidin-1-yl]benzamide, N-[(1S,2R)-2-Hydroxy-1-methyl-2-phenylethyl]-3-nitro-4-[4-(2-oxo-2H-3,1-benzoxazin-1(4H)-yl)piperidin-1-yl]benzamide, 3-Nitro-4-[4-(2-oxo-2H-3,1-benzoxazin-1(4H)-yl)piperidin-1-yl]-N-{[3,4,5-tris(methyloxy)phenyl]methyl}benzamide, 3-Nitro-4-[4-(2-oxo-2H-3,1-benzoxazin-1(4H)-yl)piperidin-1-yl]-N-(2-phenylcyclopropyl)benzamide, N-[2-Hydroxy-1-(hydroxymethyl)-1-methylethyl]-3-nitro-4-[4-(2-oxo-2H-3,1-benzoxazin-1(4H)-yl)piperidin-1-yl]benzamide, N-(1-Azabicyclo[2.2.2]oct-3-yl)-3-nitro-4-[4-(2-oxo-2H-3,1-benzoxazin-1(4H)-yl)piperidin-1-yl]benzamide, 3-Nitro-4-[4-(2-oxo-2H-3,1-benzoxazin-1(4H)-yl)piperidin-1-yl]-N-(2-piperidin-1-ylethyl)benzamide, N-(1,3-Dimethylbutyl)-3-nitro-4-[4-(2-oxo-2H-3,1-benzoxazin-1(4H)-yl)piperidin-1-yl]benzamide, N-(1-Methylbutyl)-3-nitro-4-[4-(2-oxo-2H-3,1-benzoxazin-1(4H)-yl)piperidin-1-yl]benzamide, N-(1-Methylhexyl)-3-nitro-4-[4-(2-oxo-2H-3,1-benzoxazin-1(4H)-yl)piperidin-1-yl]benzamide, N-(3-Methylbutyl)-3-nitro-4-[4-(2-oxo-2H-3,1-benzoxazin-1(4H)-yl)piperidin-1-yl]benzamide, N-[(2-Aminophenyl)methyl]-3-nitro-4-[4-(2-oxo-2H-3,1-benzoxazin-1(4H)-yl)piperidin-1-yl]benzamide, N-[2-Hydroxy-1-(hydroxymethyl)ethyl]-3-nitro-4-[4-(2-oxo-2H-3,1-benzoxazin-1(4H)-yl)piperidin-1-yl]benzamide, N-[2-(Ethylthio)ethyl]-3-nitro-4-[4-(2-oxo-2H-3,1-benzoxazin-1(4H)-yl)piperidin-1-yl]benzamide, N-[(1S)-1-(Hydroxymethyl)-2,2-dimethylpropyl]-3-nitro-4-[4-(2-oxo-2H-3,1-benzoxazin-1(4H)-yl)piperidin-1-yl]benzamide, N-(4-Methylcyclohexyl)-3-nitro-4-[4-(2-oxo-2H-3,1-benzoxazin-1(4H)-yl)piperidin-1-yl]benzamide, N-{2-Hydroxy-1-[(methyloxy)methyl]-2-phenylethyl}-3-nitro-4-[4-(2-oxo-2H-3,1-benzoxazin-1(4H)-yl)piperidin-1-yl]benzamide, N-Ethyl-3-nitro-4-[4-(2-oxo-2H-3,1-benzoxazin-1(4H)-yl)piperidin-1-yl]benzamide, N-Cyclopropyl-3-nitro-4-[4-(2-oxo-2H-3,1-benzoxazin-1(4H)-yl)piperidin-1-yl]benzamide, 3-Nitro-4-[4-(2-oxo-2H-3,1-benzoxazin-1(4H)-yl)piperidin-1-yl]-N-(phenylmethyl)benzamide, N-(1-Methylpropyl)-3-nitro-4-[4-(2-oxo-2H-3,1-benzoxazin-1(4H)-yl)piperidin-1-yl]benzamide, 1,1-Dimethylethyl 2-[({3-nitro-4-[4-(2-oxo-2H-3,1-benzoxazin-1(4H)-yl)piperidin-1-yl]phenyl}carbonyl)amino]ethylcarbamate, N-[2-(3,4-Dihydroxyphenyl)ethyl]-3-nitro-4-[4-(2-oxo-2H-3,1-benzoxazin-1(4H)-yl)piperidin-1-yl]benzamide, N-{[4-(Methyloxy)phenyl]methyl}-3-nitro-4-[4-(2-oxo-2H-3,1-benzoxazin-1(4H)-yl)piperidin-1-yl]benzamide, N-[2-(1H-Imidazol-4-yl)ethyl]-3-nitro-4-[4-(2-oxo-2H-3,1-benzoxazin-1(4H)-yl)piperidin-1-yl]benzamide, N-[(1S)-1-(Hydroxymethyl)propyl]-3-nitro-4-[4-(2-oxo-2H-3,1-benzoxazin-1(4H)-yl)piperidin-1-yl]benzamide, 3-Nitro-4-[4-(2-oxo-2H-3,1-benzoxazin-1(4H)-yl)piperidin-1-yl]-N-[1-(phenylmethyl)piperidin-4-yl]benzamide, N-[(1R)-1-(Hydroxymethyl)propyl]-3-nitro-4-[4-(2-oxo-2H-3,1-benzoxazin-1(4H)-yl)piperidin-1-yl]benzamide, N-(4-Hydroxybutyl)-3-nitro-4-[4-(2-oxo-2H-3,1-benzoxazin-1(4H)-yl)piperidin-1-yl]benzamide, 3-Nitro-4-[4-(2-oxo-2H-3,1-benzoxazin-1(4H)-yl)piperidin-1-yl]-N-tricyclo[3.3.1.1~3,7~]dec-1-ylbenzamide, N-[(1S,2S)-2-Hydroxycyclohexyl]-3-nitro-4-[4-(2-oxo-2H-3,1-benzoxazin-1(4H)-yl)piperidin-1-yl]benzamide, N-(2-Hydroxy-1-methylethyl)-3-nitro-4-[4-(2-oxo-2H-3,1-benzoxazin-1(4H)-yl)piperidin-1-yl]benzamide, N-{2-[(2-Hydroxyethyl)oxy]ethyl}-3-nitro-4-[4-(2-oxo-2H-3,1-benzoxazin-1(4H)-yl)piperidin-1-yl]benzamide, N-[1-(Hydroxymethyl)butyl]-3-nitro-4-[4-(2-oxo-2H-3,1-benzoxazin-1(4H)-yl)piperidin-1-yl]benzamide, N-(2-Amino-2-oxoethyl)-3-nitro-4-[4-(2-oxo-2H-3,1-benzoxazin-1(4H)-yl)piperidin-1-yl]benzamide, N-[1-(4-Fluorophenyl)ethyl]-3-nitro-4-[4-(2-oxo-2H-3,1-benzoxazin-1(4H)-yl)piperidin-1-yl]benzamide, 3-Nitro-4-[4-(2-oxo-2H-3,1-benzoxazin-1(4H)-yl)piperidin-1-yl]-N-(3-phenylpropyl)benzamide, N-[(1S,2R)-2-Hydroxycyclohexyl]-3-nitro-4-[4-(2-oxo-2H-3,1-benzoxazin-1(4H)-yl)piperidin-1-yl]benzamide, Ethyl 3-hydroxy-2-[({3-nitro-4-[4-(2-oxo-2H-3,1-benzoxazin-1(4H)-yl)piperidin-1-yl]phenyl}carbonyl)amino]propanoate, N-[(1R,2S)-2-Hydroxy-1-methyl-2-phenylethyl]-3-nitro-4-[4-(2-oxo-2H-3,1-benzoxazin-1(4H)-yl)piperidin-1-yl]benzamide, 1-{1-[4-(Morpholin-4-ylcarbonyl)-2-nitrophenyl]piperidin-4-yl}-1,4-dihydro-2H-3,1-benzoxazin-2-one, N,N-Dimethyl-3-nitro-4-[4-(2-oxo-2H-3,1-benzoxazin-1(4H)-yl)piperidin-1-yl]benzamide, N,N-Bis(2-hydroxyethyl)-3-nitro-4-[4-(2-oxo-2H-3,1-benzoxazin-1(4H)-yl)piperidin-1-yl]benzamide, N-(2-Hydroxyethyl)-N-methyl-3-nitro-4-[4-(2-oxo-2H-3,1-benzoxazin-1(4H)-yl)piperidin-1-yl]benzamide, N-(2-Hydroxyethyl)-3-nitro-4-[4-(2-oxo-2H-3,1-benzoxazin-1(4H)-yl)piperidin-1-yl]-N-(phenylmethyl)benzamide, 1-(1-{2-Nitro-4-[(4-phenylpiperazin-1-yl)carbonyl]phenyl}piperidin-4-yl)-1,4-dihydro-2H-3,1-benzoxazin-2-one, N-[(1S,2R)-2-hydroxy-1-methyl-2-phenylethyl]-N-methyl-3-nitro-4-[4-(2-oxo-2H-3,1-benzoxazin-1(4H)-yl)piperidin-1-yl]benzamide, N-Ethyl-N-(2-hydroxyethyl)-3-nitro-4-[4-(2-oxo-2H-3,1-benzoxazin-1(4H)-yl)piperidin-1-yl]benzamide, 1-[1-(4-{[4-(4-Fluorophenyl)piperazin-1-yl]carbonyl}-2-nitrophenyl)piperidin-4-yl]-1,4-dihydro-2H-3,1-benzoxazin-2-one,
1-{1-[4-(Azepan-1-ylcarbonyl)-2-nitrophenyl]piperidin-4-yl}-1,4-dihydro-2H-3,1-benzoxazin-2-one,
N,N-Diethyl-3-nitro-4-[4-(2-oxo-2H-3,1-benzoxazin-1(4H)-yl)piperidin-1-yl]benzamide,
N-[2-(Dimethylamino)ethyl]-3-nitro-4-[4-(2-oxo-2H-3,1-benzoxazin-1(4H)-yl)piperidin-1-yl]-N-(phenylmethyl)benzamide,
N-Ethyl-3-nitro-4-[4-(2-oxo-2H-3,1-benzoxazin-1(4H)-yl)piperidin-1-yl]-N-(phenylmethyl)benzamide,
N-Butyl-3-nitro-4-[4-(2-oxo-2H-3,1-benzoxazin-1(4H)-yl)piperidin-1-yl]-N-(phenylnethyl)benzamide,
1-{1-[2-Nitro-4-(piperidin-1-ylcarbonyl)phenyl]piperidin-4-yl}-1,4-dihydro-2H-3,1-benzoxazin-2-one,
Ethyl [({3-nitro-4-[4-(2-oxo-2H-3,1-benzoxazin-1(4H)-yl)piperidin-1-yl]phenyl}carbonyl)(phenylmethyl)amino]acetate,
N-(2-Hydroxyethyl)-N-(1-methylethyl)-3-nitro-4-[4-(2-oxo-2H-3,1-benzoxazin-1(4H)-yl)piperidin-1-yl]benzamide,
1-(1-{2-Nitro-4-[(4-pyridin-2-ylpiperazin-1-yl)carbonyl]phenyl}piperidin-4-yl)-1,4-dihydro-2H-3,1-benzoxazin-2-one,
1-{1-[2-Nitro-4-(pyrrolidin-1-ylcarbonyl)phenyl]piperidin-4-yl}-1,4-dihydro-2H-3,1-benzoxazin-2-one,
N-(2-Hydroxyethyl)-3-nitro-4-[4-(2-oxo-2H-3,1-benzoxazin-1(4H)-yl)piperidin-1-yl]-N-pentylbenzamide,
N-[2-(Diethylamino)ethyl]-N-ethyl-3-nitro-4-[4-(2-oxo-2H-3,1-benzoxazin-1(4H)-yl)piperidin-1-yl]benzamide,
N-Ethyl-N-methyl-3-nitro-4-[4-(2-oxo-2H-3,1-benzoxazin-1(4H)-yl)piperidin-1-yl]benzamide,
(2S)-1-({3-Nitro-4-[4-(2-oxo-2H-3,1-benzoxazin-1(4H)-yl)piperidin-1-yl]phenyl}carbonyl)pyrrolidine-2-carboxamide,
N-(2-Cyanoethyl)-3-nitro-4-[4-(2-oxo-2H-3,1-benzoxazin-1(4H)-yl)piperidin-1-yl]-N-(phenylmethyl)benzamide,
1-(1-{4-[(3,5-Dimethylpiperidin-1-yl)carbonyl]-2-nitrophenyl}piperidin-4-yl)-1,4-dihydro-2H-3,1-benzoxazin-2-one,
1-[1-(4-{[(2R,6S)-2,6-Dimethylmorpholin-4-yl]carbonyl}-2-nitrophenyl)piperidin-4-yl]-1,4-dihydro-2H-3,1-benzoxazin-2-one,
1-{1-[4-({4-[2-(Methyloxy)phenyl]piperazin-1-yl}carbonyl)-2-nitrophenyl]piperidin-4-yl}-1,4-dihydro-2H-3,1-benzoxazin-2-one,
1-{1-[2-Nitro-4-(thiomorpholin-4-ylcarbonyl)phenyl]piperidin-4yl}-1,4-dihydro-2H-3,1-benzoxazin-2-one,
1-(1-{4-[(4-{2-[(2-Hydroxyethyl)oxy]ethyl}piperazin-1-yl)carbonyl]-2-nitrophenyl}piperidin-4-yl)-1,4-dihydro-2H-3,1-benzoxazin-2-one,
N-Ethyl-3-nitro-4-[4-(2-oxo-2H-3,1-benzoxazin-1(4H)-yl)piperidin-1-yl]-N-(pyridin-4-ylmethyl)benzamide,
N-Methyl-3-nitro-4-[4-(2-oxo-2H-3,1-benzoxazin-1(4H)-yl)piperidin-1-yl]-N-prop-2-ynylbenzamide,
1-(1-{4-[(4-Acetylpiperazin-1-yl)carbonyl]-2-nitropheny}piperidin-4-yl)-1,4-dihydro-2H-3,1-benzoxazin-2-one,
1-[1-(4-{[2-(Hydroxymethyl)piperidin-1-yl]carbonyl}-2-nitrophenyl)piperidin-4-yl]-1,4-dihydro-2H-3,1-benzoxazin-2-one,
4-({3-Nitro-4-[4-(2-oxo-2H-3,1-benzoxazin-1(4H)-yl)piperidin-1-yl]phenyl}carbonyl)piperazine-1-carbaldehyde,
N-Methyl-3-nitro-4-[4-(2-oxo-2H-3,1-benzoxazin-1(4H)-yl)piperidin-1-yl]-N-(phenylmethyl)benzamide,
Ethyl 4-({3-nitro-4-[4-(2-oxo-2H-3,1-benzoxazin-1(4H)-yl)piperidin-1-yl]phenyl}carbonyl)piperazine-1-carboxylate,
Ethyl 1-({3-nitro-4-[4-(2-oxo-2H-3,1-benzoxazin-1(4H)-yl)piperidin-1-yl]phenyl}carbonyl)piperidine-4-carboxylate,
1-({3-Nitro-4-[4-(2-oxo-2H-3,1-benzoxazin-1(4H)-yl)piperidin-1-yl]phenyl}carbonyl)piperidine-3-carboxamide,
1-(1-{4-[(4-Methylpiperazin-1-yl)carbonyl]-2-nitrophenyl}piperidin-4-yl)-1,4-dihydro-2H-3,1-benzoxazin-2-one,
1-{1-[4-(2,5-Dihydro-1H-pyrrol-1-ylcarbonyl)-2-nitrophenyl]piperidin-4-yl}-1,4-dihydro-2H-3,1-benzoxazin-2-one,
N-Ethyl-N-(2-methylprop-2-enyl)-3-nitro-4-[4-(2-oxo-2H-3,1-benzoxazin-1(4H)-yl)piperidin-1-yl]benzamide,
N,N-Bis(cyanomethyl)-3-nitro-4-[4-(2-oxo-2H-3,1-benzoxazin-1(4H)-yl)piperidin-1-yl]benzamide,
N-Butyl-N-(cyanomethyl)-3-nitro-4-[4-(2-oxo-2H-3,1-benzoxazin-1(4H)-yl)piperidin-1-yl]benzamide,
N,N-Bis(2-hydroxypropyl)-3-nitro-4-[4-(2-oxo-2H-3,1-benzoxazin-1(4H)-yl)piperidin-1-yl]benzamide,
1-(1-{4-[(4-Hydroxypiperidin-1-yl)carbonyl]-2-nitrophenyl}piperidin-4-yl)-1,4-dihydro-2H-3,1-benzoxazin-2-one,
1-(1-{4-[(2,5-Dimethyl-2,5-dihydro-1H-pyrrol-1-yl)carbonyl]-2-nitrophenyl}piperidin-4-yl)-1,4-dihydro-2H-3,1-benzoxazin-2-one,
N-Methyl-3-nitro-4-[4-(2-oxo-2H-3,1-benzoxazin-1(4H)-yl)piperidin-1-yl]-N-propylbenzamide,
N-(2-Amino-2-oxoethyl)-N-methyl-3-nitro-4-[4-(2-oxo-2H-3,1-benzoxazin-1(4H)-yl)piperidin-1-yl]benzamide,
N,N-Diethyl-1-({3-nitro-4-[4-(2-oxo-2H-3,1-benzoxazin-1(4H)-yl)piperidin-1-yl]phenyl}carbonyl)piperidine-3-carboxamide,
N-Cyclohexyl-N-methyl-3-nitro-4-[4-(2-oxo-2H-3,1-benzoxazin-1(4H)-yl)piperidin-1-yl]benzamide,
N-[2-(Methyloxy)ethyl]-3-nitro-4-[4-(2-oxo-2H-3,1-benzoxazin-1(4H)-yl)piperidin-1-yl]benzamide,
N-(1-Methylethyl)-6-[4-(2-oxo-2H-3,1-benzoxazin-1(4H)-yl)piperidin-1-yl]pyridine-3-carboxamide,
5-Chloro-N-(1-methylethyl)-6-[4-(2-oxo-2H-3,1-benzoxazin-1(4H)-yl)piperidin-1-yl]pyridine-3-carboxamide,
N-(1-Methylethyl)-3-nitro-4-[4-(2-oxo-2H-3,1-benzoxazin-1(4H)-yl)piperidin-1-yl]benzenesulfonamide,
1-[1-(4-Amino-2-chlorophenyl)piperidin-4-yl]-1,4-dihydro-2H-3,1-benzoxazin-2-one,
3-Cyano-N-(1-methylethyl)-4-[4-(2-oxo-2H-3,1-benzoxazin-1(4H)-yl)piperidin-1-yl]benzamide,
N-{3-Chloro-4-[4-(2-oxo-2H-3,1-benzoxazin-1(4H)-yl)piperidin-1-yl]phenyl}-2-methylpropanamide,
N-{3-Chloro-4-[4-(2-oxo-2H-3,1-benzoxazin-1(4H)-yl)piperidin-1-yl]phenyl}propane-2-sulfonamide, N-{3-Chloro-4-[4-(2-oxo-2H-3,1-benzoxazin-1(4H)-yl) piperidin-1-yl]phenyl}-1-cyanocyclopropanecarboxamide, (2S)-N-{3-Chloro-4-[4-(2-oxo-2H-3,1-benzoxazin-1 (4H)-yl)piperidin-1-yl]phenyl}-1-methylpyrrolidine-2-carboxamide, 5-Chloro-N-(1-methylethyl)-6-[4-(4-methyl-2-oxo-2H-3, 1-benzoxazin-1(4H)-yl)piperidin-1-yl]pyridine-3-carboxamide, ±-5-Chloro-N-(1-methylethyl)-6-[(cis)-3-methyl-4-(2-oxo-2H-3,1-benzoxazin-1(4H)-yl)piperidin-1-yl] pyridine-3-carboxamide, ±-5-Chloro-N-(1-methylethyl)-6-[(trans)-3-methyl-4-(2-oxo-2H-3,1-benzoxazin-1(4H)-yl)piperidin-1-yl] pyridine-3-carboxamide, 2-[4-(2-Oxo-2H-3,1-benzoxazin-1(4H)-yl)piperidin-1-yl]-N-(1,3,4-thiadiazol-2-yl)-4-(trifluoromethyl) pyrimidine-5-carboxamide, 2-[4-(2-Oxo-2H-3,1-benzoxazin-1(4H)-yl)piperidin-1-yl]-N-(1H-1,2,4-triazol-3-yl)-4-(trifluoromethyl) pyrimidine-5-carboxamide, 2-[4-(2-Oxo-2H-3,1-benzoxazin-1(4H)-yl)piperidin-1-yl]-N-(1H-pyrazol-3-yl)-4-(trifluoromethyl) pyrimidine-5-carboxamide, N-(4-Hydroxycyclohexyl)-2-[4-(2-oxo-2H-3,1-benzoxazin-1(4H)-yl)piperidin-1-yl]-4-(trifluoromethyl)pyrimidine-5-carboxamide, N-[1-(Hydroxymethyl)propyl]-2-[4-(2-oxo-2H-3,1-benzoxazin-1(4H)-yl)piperidin-1-yl]-4-(trifluoromethyl)pyrimidine-5-carboxamide, N-(3-Hydroxy-2,2-dimethylpropyl)-2-[4-(2-oxo-2H-3,1-benzoxazin-1(4H)-yl)piperidin-1-yl]-4-(trifluoromethyl)pyrimidine-5-carboxamide, 2-[4-(2-Oxo-2H-3,1-benzoxazin-1(4H)-yl)piperidin-1-yl]-N-(tetrahydrofuran-2-ylmethyl)-4-(trifluoromethyl)pyrimidine-5-carboxamide, N-Cyclobutyl-2-[4-(2-oxo-2H-3,1-benzoxazin-1(4H)-yl) piperidin-1-yl]-4-(trifluoromethyl)pyrimidine-5-carboxamide, N-Cyclopentyl-2-[4-(2-oxo-2H-3,1-benzoxazin-1(4H)-yl)piperidin-1-yl]-4-(trifluoromethyl)pyrimidine-5-carboxamide, N-[2-(1H-Imidazol-4-yl)ethyl]-2-[4-(2-oxo-2H-3,1-benzoxazin-1(4H)-yl)piperidin-1-yl]-4-(trifluoromethyl)pyrimidine-5-carboxamide, N-(1-Ethynylcyclohexyl)-2-[4-(2-oxo-2H-3,1-benzoxazin-1(4H)-yl)piperidin-1-yl]-4-(trifluoromethyl)pyrimidine-5-carboxamide, N-[(1R)-1-(Hydroxymethyl)-2-methylpropyl]-2-[4-(2-oxo-2H-3,1-benzoxazin-1(4H)-yl)piperidin-1-yl]-4-(trifluoromethyl)pyrimidine-5-carboxamide, N-(2-Hydroxy-1,1-dimethylethyl)-2-[4-(2-oxo-2H-3,1-benzoxazin-1(4H)-yl)piperidin-1-yl]-4-(trifluoromethyl)pyrimidine-5-carboxamnide, N-(1,1-Diethylprop-2-ynyl)-2-[4-(2-oxo-2H-3,1-benzoxazin-1(4H)-yl)piperidin-1-yl]-4-(trifluoromethyl)pyrimidine-5-carboxamide, N-(2-Hydroxy-1-methylethyl)-2-[4-(2-oxo-2H-3,1-benzoxazin-1(4H)-yl)piperidin-1-yl]-4-(trifluoromethyl)pyrimidine-5-carboxamide, N-[1-Methyl-2-(methyloxy)ethyl]-2-[4-(2-oxo-2H-3,1-benzoxazin-1(4H)-yl)piperidin-1-yl]-4-(trifluoromethyl)pyrimidine-5-carboxamide, N-(1-Methylethyl)-2-[4-(2-oxo-2H-3,1-benzoxazin-1 (4H)-yl)piperidin-1-yl]pyrimidine-5-carboxamide, N-(1-Methylethyl)-2-[4-(2-oxo-2H-3,1-benzoxazin-1 (4H)-yl)piperidin-1-yl]-1,3-thiazole-4-carboxamide, N-(1-Methylethyl)-3-(methylsulfonyl)-4-[4-(2-oxo-2H-3, 1-benzoxazin-1(4H)-yl)piperidin-1-yl]benzamide, N-[(1R)-1-(Aminocarbonyl)-2-methylpropyl]-5-chloro-6-[4-(2-oxo-2H-3,1-benzoxzin-1(4H)-yl)piperidin-1-yl]pyridine-3-carboxamide, 5-Chloro-N-(2-hydroxy-1-methylethyl)-6-[4-(2-oxo-2H-3,1-benzoxazin-1(4H)-yl)piperidin-1-yl]pyridine-3-carboxamide, 5-Chloro-N-(1,1-dimethylprop-2-ynyl)-6-[4-(2-oxo-2H-3,1-benzoxazin-1(4H)-yl)piperidin-1-yl]pyridine-3-carboxamide, N-(2-Amino-1-cyano-2-oxoethyl)-5-chloro-6-[4-(2-oxo-2H-3,1-benzoxazin-1(4H)-yl)piperidin-1-yl]pyridine-3-carboxamide, N-[(1R)-1-(Aminocarbonyl)-3-methylbutyl]-5-chloro-6-[4-(2-oxo-2H-3,1-benzoxazin-1(4H)-yl)piperidin-1-yl] pyridine-3-carboxamide, N-[(1S)-1-(Aminocarbonyl)-2-methylpropyl]-5-chloro-6-[4-(2-oxo-2H-3,1-benzoxazin-1(4H)-yl)piperidin-1-yl] pyridine-3-carboxamide, N-[(1S)-1-(Aminocarbonyl)-3-methylbutyl]-5-chloro-6-[4-(2-oxo-2H-3,1-benzoxazin-1(4H)-yl)piperidin-1-yl] pyridine-3-carboxamide, 5-Chloro-N-(1-methylethyl)-6-[4-(3-oxo-2,3-dihydro-4H-1,4-benzoxazin-4-yl)piperidin-1-yl]pyridine-3-carboxamide, N-(1-Methylethyl)-3-nitro-4-[4-(2-oxo-2H-3,1-benzoxazin-1(4H)-yl)piperidin-1-yl]benzamide, N-[(1S)-1-(Aminocarbonyl)-2-methylbutyl]-3-nitro-4-[4-(2-oxo-2H-3,1-benzoxazin-1-yl)piperidin-1-yl] benzamide, N-(1-Methylethyl)-2-[4-(2-oxo-2H-3,1-benzoxazin-1 (4H)-yl)piperidin-1-yl]-4-(trifluoromethyl)-5-pyrimidine-5-carboxamide, 3-Chloro-N-(1-methylethyl)-4-[4-(2-oxo-2H-3,1-benzoxazin-1(4H)-yl)piperidin-1-yl]benzamide, 3-Amino-N-(1-methylethyl)-4-[4-(2-oxo-2H-3,1-benzoxazin-1(4H)-yl)piperidin-1-yl]benzamide, N-(1-Methylethyl)-4-[4-(2-oxo-2H-3,1-benzoxazin-1 (4H)-yl)piperidin-1-yl]benzamide, N-[(1S)-1-(Aminocarbonyl)-3-methylbutyl]-4-[4-(2-oxo-2H-3,1-benzoxazin-1(4H)-yl)piperidin-1-yl] benzamide, 3-(Ethylamino)-N-(1-methylethyl)-4-[4-(2-oxo-2H-3,1-benzoxazin-1(4H)-yl)piperidin-1-yl]benzamide, 3-(Diethylamino)-N-(1-methylethyl)-4-[4-(2-oxo-2H-3, 1-benzoxazin-1(4H)-yl)piperidin-1-yl]benzamide, N-(1-Methylethyl)-3-[(methylsulfonyl)amino]-4-[4-(2-oxo-2H-3,1-benzoxazin-1(4H)-yl)piperidin-1-yl] benzamide, 4-[4-(7-Chloro-2-oxo-2H-3,1-benzoxazin-1(4H)-yl) piperidin-1-yl]-N-(1-methylethyl)-3-nitrobenzamide, or a pharmaceutically acceptable salt or solvate thereof.

9. A pharmaceutical composition comprising a compound according to claim 1 in combination with a pharmaceutically acceptable diluent, adjuvent or carrier.

10. A process for the preparation of a compound of formula (I) which comprises reaction of a compound of formula (II):

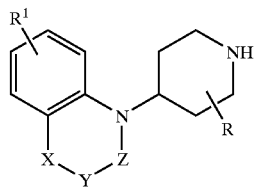

(II)

where R, $R^1$, X, Y and Z are as defined in claim 1 or a protected derivative thereof, with a compound of formula (III):

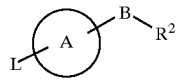

(III)

where B and $R^2$ are as defined in claim 1 or a protected derivative thereof, and L is a leaving group, and optionally thereafter in any order:

converting one or more functional groups into further functional groups removing any protecting groups forming a pharmaceutically acceptable salt or solvate.

11. A method of treating rheumatoid arthritis in a warm blooded animal in need thereof which comprises administering to said animal a therapeutically effective amount of a compound according to any one of claims 1 to 8.

12. A method of treating chronic obstructive pulmonary disease in a warm blooded animal in need thereof which comprises administering to said animal a therapeutically effective amount of a compound according to any one of claims 1 to 8.

13. A method of treating osteoarthritis in a warm blooded animal in need thereof which comprises administering to said animal a therapeutically effective amount of a compound according to any one of claims 1 to 8.

14. A method of treating asthma in a warm blooded animal in need thereof which comprises administering to said animal a therapeutically effective amount of a compound according to any one of claims 1 to 8.

* * * * *